US011340227B2

(12) United States Patent
Francklyn et al.

(10) Patent No.: US 11,340,227 B2
(45) Date of Patent: May 24, 2022

(54) METHODS AND COMPOUNDS FOR DIAGNOSING THREONYL-TRNA SYNTHETASE-ASSOCIATED DISEASES AND CONDITIONS

(71) Applicant: The University of Vermont and State Agricultural College, Burlington, VT (US)

(72) Inventors: Christopher Francklyn, Burlington, VT (US); Karen M. Lounsbury, Essex Junction, VT (US); Tamara Williams, South Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 55 days.

(21) Appl. No.: 16/202,884

(22) Filed: Nov. 28, 2018

(65) Prior Publication Data

US 2019/0120842 A1    Apr. 25, 2019

Related U.S. Application Data

(62) Division of application No. 14/416,347, filed as application No. PCT/US2013/051806 on Jul. 24, 2013, now Pat. No. 10,175,237.

(60) Provisional application No. 61/675,652, filed on Jul. 25, 2012.

(51) Int. Cl.
| *G01N 33/573* | (2006.01) |
| *C12Q 1/25* | (2006.01) |
| *C12Q 1/6883* | (2018.01) |
| *C12Q 1/6886* | (2018.01) |
| *G01N 33/574* | (2006.01) |

(52) U.S. Cl.
CPC ............. *G01N 33/573* (2013.01); *C12Q 1/25* (2013.01); *C12Q 1/6883* (2013.01); *C12Q 1/6886* (2013.01); *G01N 33/57496* (2013.01); *C12Q 2600/118* (2013.01); *C12Q 2600/158* (2013.01); *G01N 2333/9015* (2013.01); *G01N 2800/52* (2013.01); *G01N 2800/7014* (2013.01)

(58) Field of Classification Search
None
See application file for complete search history.

(56) References Cited

U.S. PATENT DOCUMENTS

| 5,795,757 | A | 8/1998 | Hodgson et al. |
| 2012/0058133 | A1 | 3/2012 | Whitman et al. |
| 2013/0129704 | A1 | 5/2013 | Greene et al. |
| 2015/0166976 | A1 | 6/2015 | Francklyn et al. |
| 2015/0210997 | A1 | 7/2015 | Francklyn et al. |

FOREIGN PATENT DOCUMENTS

| EP | 1576160 B1 | 5/2007 |
| WO | 2011097031 A2 | 8/2011 |
| WO | 2011139801 A3 | 11/2011 |

OTHER PUBLICATIONS

Ahmed et al., "A new rapid and simple non-radioactive assay to monitor and determine the proliferation of lymphocytes: an alternative to [3H]thymidine incorporation assay." J Immunol. Methods, 1994, vol. 170, pp. 211-224.
Altundag et al.,"CA125 Nadir values as a prognostic factor in epithelial ovarian cancer." J Clin. Oneal., 2005, vol. 23, pp. 2435-2436.
Arnaoutova, I. and H. K. Kleinman, "In vitro angiogenesis: endothelial cell tube formation on gelled basement membrane extract." Nat Protoc, 2010, vol. 5, pp. 628-635.
Bikfalvi, A. and Bicknell, R., "Recent advances in angiogenesis, anti-angiogenesis and vascular targeting", Trends in Pharmacological Sciences, Dec. 2002, vol. 23, pp. 576-582.
Bonfils, G.M. et al., "Leucyl-tRNA synthetase controls TORC1 via the EGO complex", Molecular Cell, 2012, vol. t6, pp. 105-110.
Brown, MV et al., "Mammalian aminoacyl-tRNA synthetases: cell signaling functions of the protein translation machinery", Vascul. Pharmacol, 2010, vol. 52, pp. 21-26.
Cassavaugh, J . M., et al., "Negative regulation of HIF-1alpha by an FBW7-mediated degradation pathway during hypoxia." J Cell Biochem, 2011, vol. 112, pp. 3882-3890.
Chandran, U.R. et al., "Gene expression profiles of prostate cancer reveal involvement of multiple molecular pathways in the metastatic process." BMC Cancer, Apr. 12, 2007, vol. 7, pp. 1-21.
Chang, H., et al., "Agonist and antagonist effects of diadenosine tetraphosphate, a platelet dense granule constituent on platelet P2Y1, P2Y12 and P2X1 receptors." Thromb. Res, 2010, vol. 125, pp. 159-165.
Conant, JL. et al., "Sarcomatiod renal cell carcinoma is an examples fa epithelial-mesenchymal transition." J. Clin. Pat, 2011, vol. 64, pp. 1088-1092.
Delicado, E.G. et al., "Dinucleoside polyphosphates and their interaction with other nucleotide signaling pathways." Pfluger Arch, 2006, vol. 452, pp. 563-572.
Dieterich, D.C. et al., "Labeling, detection and identification of newly synthesized proteomes with bioorthogonal non-canonical amino-acid tagging." Nat. Protoc. 2007, vol. 2, pp. 532-540.
Eastwood, E.L. and S.E. Schaus, "Borrelidin induces the transcription of amino acid biosynthetic enzymes via a GCN4-dependent pathway_" Bioorg. Med. Chem. Lett, Jul. 2003, vol. 13, pp. 2235-2237.

(Continued)

*Primary Examiner* — Kagnew H Gebreyesus
(74) *Attorney, Agent, or Firm* — Pierce Atwood LLP

(57) ABSTRACT

The invention includes, in part, methods and compounds for diagnosing diseases and conditions characterized by altered threonyl-tRNA synthetase (TARS) activity, which include, but are not limited to diseases and conditions in which angiogenesis is altered. In some embodiments of the invention, a level of a TARS molecule is determined and compared to a control level of TARS to assess onset, progression, and/or regression of a disease or condition associated with altered TARS activity.

16 Claims, 18 Drawing Sheets

Specification includes a Sequence Listing.

(56) References Cited

OTHER PUBLICATIONS

Even-Zohar, N. et al., "Nutrition-induced catch-up growth increases hypoxia inducible factor 1 a RNA levels in the Growth plate." Bone, 2008, vol. 42, pp. 505-515.
Ewing, R. M., et al. "Large-scale mapping of human protein-protein interactions by mass spectrometry." Mol. Syst. Biol. 2007, vol. 3, p. 89.
Folkman, J., "Angiogenesis-dependent diseases." Semin. Oncol, Dec. 2001, vol. 28, pp. 536-452.
Fox, P.L. et al., "Noncanonical Functions of Aminoacyl-tRNA Synthetases in Translational Control." Translational Control in Biology and Medicine, 2007, vol. 29, pp. 829-854.
Francklyn, C. S., et al., "Methods for kinetic and thermodynamic analysis of aminoacyl-tRNA synthetases." Methods, 2008, vol. 44, pp. 100-118.
Funahashi, Y. et al., "Establishment of a quantitative mouse dorsal air sac model and its application to evaluate a new angiogenesis inhibitor." Oncol. Res., 1999, vol. 11, pp. 319-329.
Gantt, J.S. et al., "Increased levels of threonyl-tRNA synthetase in a borrelidin resistant Chinese hamster ovary cell ine." PNAS, Sep. 1981, vol. 78, pp. 5367-5370.
Ghanipour, A. et al., "The Prognostic Significance of Tryptophanyl-tRNA Synthetase in Colorectal Cancer." Cancer Epidemiol Biomarkers, Nov. 2009, vol. 18, pp. 2949-2956.
Greenberg, Y. et al., "The novel fragment of tyrosyl tRNA synthetase, mini-TyrRS, is secreted to induce an angiogenic response in endothelial cells." The FASEB Journal, May 2008, vol. 22, pp. 1597-1605.
Guo, M. et al., "New functions of aminoacyl-tRNA synthetases beyond translation." Nature Reviews, Sep. 2010, vol. 11, pp. 668-674.
Guo, RT. et al., "Crystal structures and biochemical analyses suggest a unique mechanism and role for human Jlycyl-tRNA synthetase in Ap4A homeostasis." J. Biol. Chem., 2009, vol. 284, pp. 28968-28976.
Habibi, D.et al., "Borrelidin, a small molecule nitrile-containing macrolide inhibitor of threonyl-tRNA synthetase, is a potent inducer of apoptosis in acute lymphoblastic leukemia." Springer, Jun. 17, 2011, pp. 1-10.
Han, J.M. et al., "Leucyl-tRNA synthetase is an intracellular leucine sensor for the mTORC1-signaling pathway", Cell, 2012, vol. 149, pp. 410-424.
Harisi, R. et al., "Differential Inhibition of Single and Cluster Type Tumor Cell Migration." Anticancer Research, 2009, vol. 29, pages.
Herzog, W. et al., "Genetic evidence for a non-canonical function of seryl-tRNA synthetase in vascular development", Circulation Research, Jun. 5, 2009, vol. 104, pp. 1260-1266.
Howard, O.M. Z. et al., "Histidyl-tRNA Synthetase and Asparaginyl-tRNA Synthetase, Autoantigens in Myositis, Activate Chemokine Receptors on T Lymphocytes and Immature Dendritic Cells." The Journal of Experimental Medicine, Sep. 16, 2002, vol. 196, pp. 781-791.
International Preliminary Report on Patentability dated Feb. 5, 2015 for the International Patent Application No. PCT/US2013/051807, 12 pages.
International Preliminary Report on Patentability dated Jan. 27, 2015 for the International Patent Application No. PCT/US2013/051806, 5 pages.
International Preliminary Report on Patentability dated Feb. 5, 2015 for the International Patent Application No. PCT/US2013/051808, 10 pages.
International Search Report and the Written Opinion of the International Searching Authority dated Oct. 10, 2013 for International Patent Application No. PCT/US2013/051806, 15 pages.
International Search Report and the Written Opinion of the International Searching Authority dated Oct. 24, 2013 for International Patent Application No. PCT/US2013/051808, 17 pages.
International Search Report and the Written Opinion of the International Searching Authority dated Oct. 22, 2013 for International Patent Application No. PCT/US2013/051807, 15 pages.
Kawamura, T. et al., "Anti-angiogenesis Effects of Borrelidin are Mediated through Distinct Pathways: Threonyl-tRNA Synthetase and Caspases are Independently Involved in Suppression of Proliferation and Induction of Apoptosis in Endothelial Cells." The Journal of Antibiotics, Aug. 2003, vol. 56, pp. 709-715.
Kim, s. et al., "Aminoacyl-tRNA synthetases and tumorigenesis: more than housekeeping." Nature, Oct. 2011, vol. 11, pp. 708-719.
Ko, Y.G. et al., "Glutamine-dependent Antiapoptotic Interaction of Human Glutaminyl-tRNA Synthetase with Apoptosis Signal-regulating Kinase 1*", The Journal of Biological Chemistry, Feb. 2001, vol. 276, pp. 6030-6036.
Kontis, K. and S. Arfin, "Isolation of a cDNA clone for human threonyl-tRNA synthetase: amplification of the structural gene in borrelidin-resistant cell lines." Molecular and Cellular Biology, May 1989, vol. 9, pp. 1832-1838.
Lee, Y.N. et al., "The function of lysyl-tRNA synthetase and Ap4A as signaling regulators of MITF activity in FcepsilonRI-activated mast cells." Immunity, 2004, vol. 20, pp. 145-151.
Liao, D. and Johnson, R.S,"Hypoxia" a key regulator of angiogenesis in cancer, Cancer and Metastasis Reviews, 2007, vol. 26, pp. 281-290.
Longair, M. H., et al., "Simple Neurite Tracer: open source software for reconstruction, visualization and analysis of neuronal processes." Bioinformatics, 2011, vol. 27, pp. 2453-2454.
Lounsbury, K.M., et al., "A family of proteins that stabilize the Ran/TC4 GTPase in its GTP-bound conformation." J. Biol. Chem, 1994, vol. 269, pp. 11285-11290.
Mathews et al., "Anti-Threonyl-tRNA Synthetase, A Second Myositis-Related Autoantibody", J _ ExP. Med, Aug. 1984, vol. 160, pp. 420-434.
McLennan, A.G. "Dinucleoside ployphosphates-friend or foe?" Pharmacol. Ther., 2000, vol. 87, pp. 73-89.
Mehta, R et al "Proteosomal Regulation of the Hypoxic Response modulates aging in C. elegans." Science, May 2009, vol. 324, pp. 1196-1198.
Mor, G., et al., "Serum protein markers for early detection of ovarian cancer." Proc. Natl. Acad. Sci. U S A, 2005, vol. 102, pp. 7677-7682.
Moss, S.J. et al., "Biosynthesis of the angiogenesis inhibitor borrelidin: directed biosynthesis of novel analogues." Chem. Communications, Jun. 14, 2006, vol. 22, pp. 2341-2343.
Nagamitsu, T. et al., "Total Synthesis of Borrelidin" J. Org. Chem., 2007, vol. 72, pp. 2744-2756.
Nass, G. and K. Poralla, "Genetics of borrelidin resistant mutants of *Saccharomyces cerivisiae* and properties of heir threonyl-tRNA-synthetase." Mol. Gen. Genet, Aug. 1976, vol. 10, pp. 39-43.
NCBI, GenBank Accession No. NM-152295.4, Jun. 27, 2012.
Ofir-Birin, Y. et al., "Structural Switch of Lysyl-tRNA Synthetase between Translation and Transcription." Mol Cell, 2013, vol. 49, pp. 30-42.
Olano,C. et al., "Biosynthesis of the Angiogenesis Inhibitor Borrelidin by Streptomyces parvulus Tu4055: Cluster Analysis and Assignment of Functions." Chemistry & Biology, Jan. 2004, vol. 11, pp. 87-97.
Olsson, A.K. et al., "VEGF receptor signaling—in control of vascular function." Nat. Rev. Mol. Cell Biol, 2006, vol. 7, pp. 359-371.
Park, S. et al., "Aminoacyl tRNA systhetases and their connections to disease." PNAS, Aug. 12, 2008, vol_ 105, pp. 11043-11049.
Ribatti, D., et al., "The gelatin sponge-chorioallantoic membrane assay." Nat. Protoc. 2006, vol. 1, pp. 85-91.
Roedersheimer, M. et al., "Complementary effects of extracellular nucleotides and platelet-derived extracts on ngiogenesis of vasa vasorum endothelial cells in vitro and subcutaneous Matrigel plugs in vivo." Vase Cell, 2011, vol. 3, p. 4.
Ruan, B. et al., "A Unique Hydrophobic Cluster Near the Active Site Contributes to Differences in Borrelidin Inhibition mong Threonyl-tRNA Sythetases." The Journal of Biological Chemistry, Jan. 7, 2005, vol. 280, pp. 571-577.
Seibold, M. et al., "Homoserine and threonine pools of borrelidin resistant *Saccharomyces cerevisiae* mutants with an altered aspartokinase" Arch. Microbial., Jul. 1981, vol. 129, pp. 368-370.

(56) References Cited

OTHER PUBLICATIONS

Simirnova, EV. et al., "Noncanonical Functions of AminoacyltRNA Synthetases" Biochemisty {Moscow), 2012, vol. 17, pp. 15-25.
Strausberg, R. L, "The Cancer Genome Anatomy Project: new resources for reading the molecular signatures of cancer." J. Pathol. 2001, vol. 195, pp. 31-40.
Svensson, K. J., et al., "Hypoxia triggers a proangiogenic pathway involving cancer cell microvesicles and PAR-2-mediated heparin-binding EGF signaling in endothelial cells." Proc. Natl. Acad. Sci. USA, 2011, vol. 108, pp. 13147-13152.
Tomlins, S. A, et al., "Integrative molecular concept modeling of prostate cancer progression." Nat. Genet, 2007, vol. 39, pp. 41-51.
Tsuchiya, E et al., "Borrelidin inhibits a Cyclin-dependent kinase {CDK), Cdc28/Cln2 of *Saccharomyces cerevisiae*." J of Antibiotics, Jan. 2001, vol. 54. pp. 84-90.
Uhlen, M., et al., "Towards a knowledge-based Human Protein Atlas." Nat. Biotechnol, 2010, vol. 28, pp. 1248-1250.
Vazquez-Mena et al., "Amplified Genes May Be Overexpressed, Unchanged, or Downregulated in Cervical Cancer Cell Lines", PLoS ONE, Mar. 2012, vol. 7, pp. 1-17.
Vellaichamy, A. et al., "Proteomic Interrogation of Androgen Action in Prostate Cancer Cells Reveals Roles of Aminoacyl tRNA Synthetases." Plos ONE, Sep. 2009, vol. 4, pp. 1-12.
Vong, B.G. et al., "Stereoselective Total Syntheis of (-)-Borrelidin." Angew. Chem. Int. Ed., 2004, vol. 43, pp. 3947-3951.
Wakabayashi, T et al., "Borreldin is an angiogenesis inhibitor; disruption of angiogenic capillary vessels in rat aorta matrix culture model." J. Antibiotics, Aug. 1997, vol. 50, pp. 671-676.
Wakasugi, K. and P. Sshimmel, "Two distinct cytokines released from a human aminoacyl-tRNA synthetase." Science, 1999, vol. 284, pp. 147-151.
Wilkinson, B., et al., "Separation of anti-angiogenic and cytotoxic activities of borrelidin by modification at the C17 side chain." Bioorg. Med. Chem. Lett, 2006, vol. 16, pp. 5814-5817.
Williams, T. et al., "Secreted Threonyl-tRNA synthetase stimulates endothelial cell migration and angiogenesis." Scientific Reports, Feb. 21, 2013, vol. 3:1317, pp. 1-7.
Wong, C., et al., "VEGF and HIF-1alpha expression are increased in advanced stages of epithelial ovarian cancer." Gynecol. Oncol, 2003, vol. 91, pp. 513-517.
Woolard, J. et al., "Borrelidin modulates the alternative splicing of VEGF in favour of anti-angiogenic isoforms." Chemical Science, 2011, vol. 2, pp. 273-278.
Zampieri, S. et al., "Polymyositis, dermatomyositis and malignancy: A further intriguing link." Autoimmunity Reviews, 2010, vol. 9, pp. 449-453.
Castranova, et al., "Aminoacyl-Transfer RNA Synthetase Deficiency Promotes Angiogenesis via the Unfolded Protein Response Pathway." Arterioscler Thromb Vasc Biol is available at http://atvb.ahajournals.org, pp. 655-662, 2016.
Fang, et al., "Structural basis for full-spectrum inhibition of translational functions on a tRNA synthetase." Nature Communications, 6:6402 , pp. 1-11, 2015.
Mirando, et al., "Aminoacyl-tRNA synthetase dependent angiogenesis revealed by a bioengineered macrolide inhibitor." Scientific Reports, 5:13160., pp. 1-17. 2015.
Sidhu, et al., "Borrelidin Induces the Unfolded Protein Response in Oral Cancer Cells and Chop-Dependent Apoptosis." ACS Med. Chem. Lett. 2015, 6, 1122-1127, 2015.
Agarwal, Sunita, "Treatment of Oral Hemangioma with 3% Tetradecyl Sulfate Study of 20 Cases" Indian J Otolaryngol Head Neck Surg. Sep. 2012;64(3):205-7.
Butryn, M. L. et al., "Behavioral Treatment of Obesity" Psychiatr Clin North Am. Dec. 2011;34(4):841-59.
Cha, E. & Fong, L. "Immunotherapy for Prostate Cancer: Biology and Therapeutic Approaches" J Clin Oncol. Sep. 20, 2011;29(27):3677-85.
Temkin, S.M. & Fleming, G. "Current Treatment of Metastatic Endometrial Cancer" Cancer Control Jan. 2009;16(1):38-45.
Yoo, Stephen "GI-Associated Hemangiomas and Vascular Malformations" Clin Colon Rectal Surg. Sep. 2011;24(3):193-200.

Control 10 nM BC194

1000 nM BC194

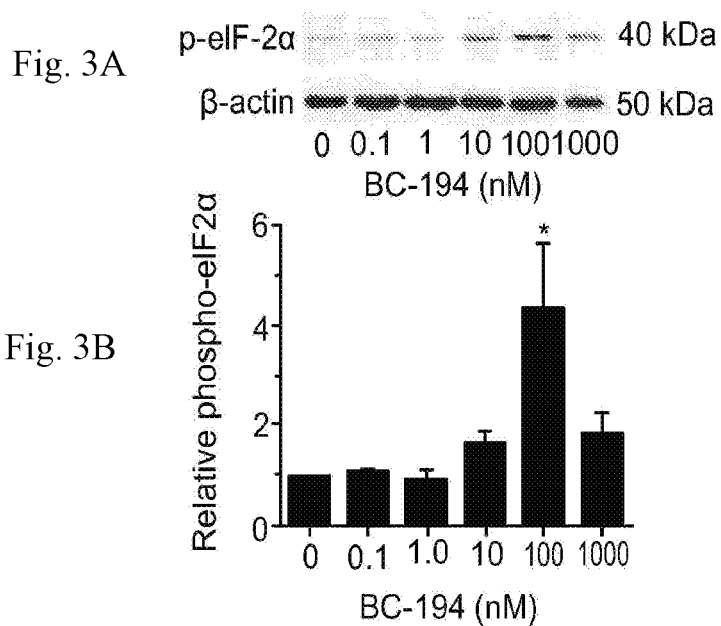
Fig. 3A
Fig. 3B
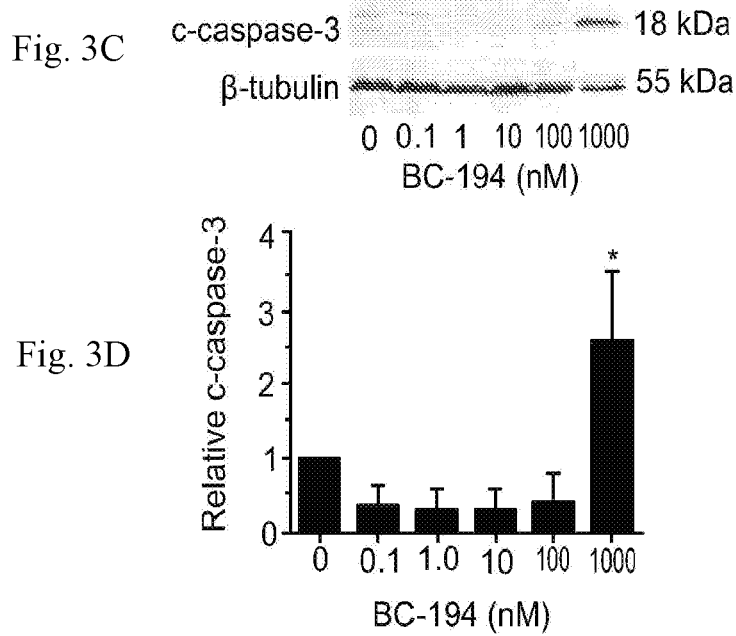
Fig. 3C
Fig. 3D

Low serum

Full serum

Low serum + TARS

Full serum + BC194

Fig. 7C     TARS                      TARS+BC194
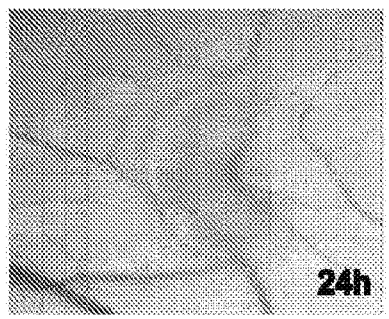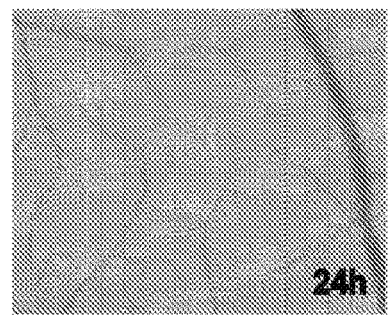
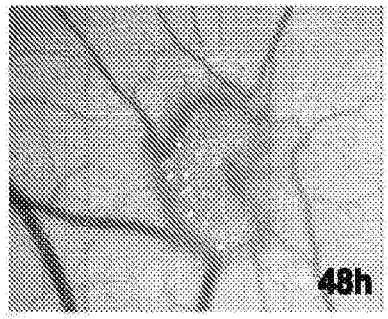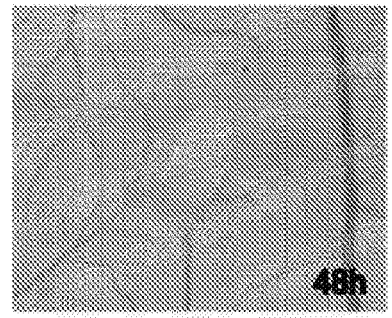
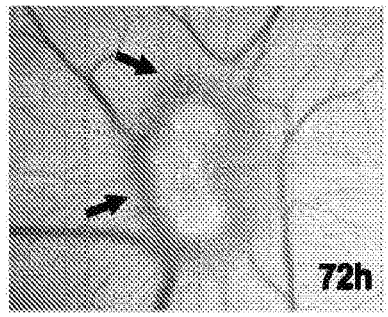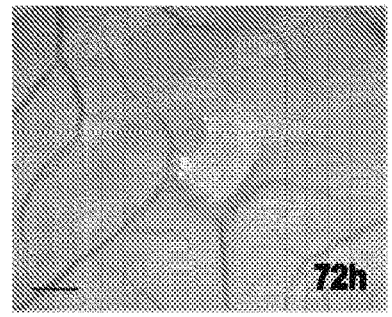

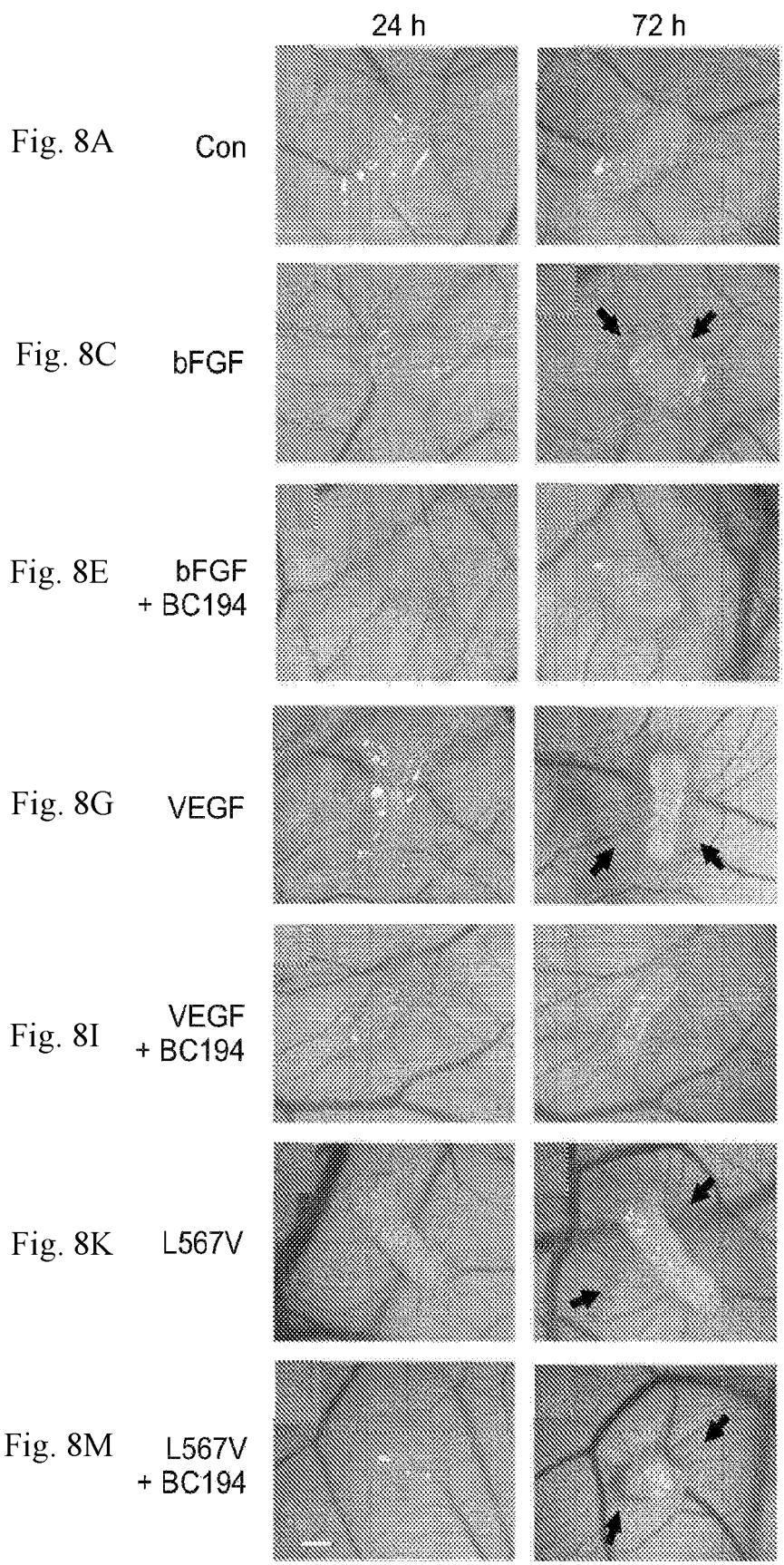

Fig.13A

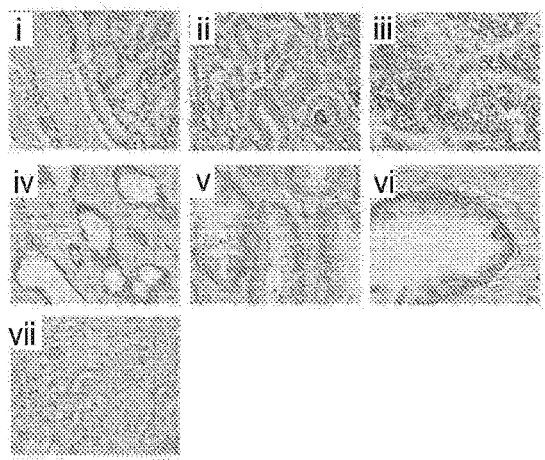

Fig. 13B

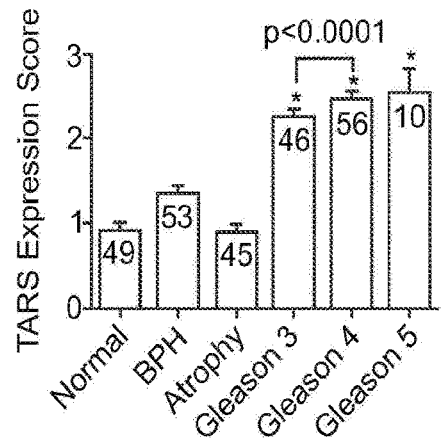

Fig. 13C

|  | Recent Prostate Specific Antigen (PSA) assay | PSA assay at diagnosis | Gleason Score | Treatment Status | TARS concentration (pg/mL) |
|---|---|---|---|---|---|
| Age matched controls (4 subjects) | N.A.[1] | N.A. | N.A. | N.A. | 105.14 ± 19.5 (S.E.M.) |
| Subject TARS0011 | unknown | unknown | 6 | None as yet | 10.94 |
| Subject TARS0012 | unknown | unknown | unknown | XRT in 1999; on androgen deprivation | 158.8 |
| Subject TARS0013 |  | 4.4 | 6 | Active surveillance | 202.27 |
| Subject TARS0014 | 23.3 | 6.4 | 9 | XRT + RRP, now androgen deprivation | undetectable |
| Subject TARS0015 | 1.5 |  | 6 | Active surveillance | 4.65 |
| Subject TARS0016 | 92.3 | 180 (metastatic) | 9 | androgen deprivation | undetectable |
| Subject TARS0017 | 8.6 | unknown | unknown | XRT, androgen deprivation | 19.251 |
| Subject TARS0018 | unknown | 6.2 | 7 | None as yet | undetectable |
| Subject TARS0019 | 6.5 | unknown | 7 | None as yet | 69.327 |
| Subject TARS0020 | 3.5 | 3.5 | 6 | Active surveillance | 84.615 |

1. Not applicable or available
2. XRT; external beam radiation therapy
3. RRP; radical retropubic prostatectomy Selected Interaction from affinity purified TARS identified by mass spectrometry

| Prey Gene Names | XC Score | # Peptides ID'd | Condition | Gene Function |
|---|---|---|---|---|
| TARSL2 | 38.28 | 4 | 1,2 | Threonyl-tRNA Synthetase (second cytoplasmic paralog) |
| EPRS | 30.19 | 4 | 1 | Bifunctional GluProRS |
| PARP | 30.16 | 4 | 2 | Poly [ADP ribose] polymerase |
| eEF1A1 | 10.16 | 2 | 1,2 | Elongation factor 1-alpha 1 |
| GAPDH | 10.16 | 1 | 2 | Glyceraldehyde-3-phosphate dehydrogenase |
| ENO1 | 10.15 | 1 | 2 | Alpha-enolase |
| MARS | 10.15 | 1 | 1 | Methionyl-tRNA synthetase (cytoplasmic) |
| NUP107 | 10.15 | 1 | 1 | Nuclear pore complex |
| VHL-1 | 10.1 | 1 | 2 | Von Hippel Lindau Tumor Suppressor |
| VHL-3 | 10.1 | 1 | 2 | Von Hippel Lindau Tumor Suppressor |
| LARS | 10.14 | 1 | 2 | Leucyl-tRNA synthetase (cytoplasmic) |
| eEF1G | 10.11 | 1 | 2 | Elongation Factor 1-gamma |
| TARS2 | 8.13 | 1 | 1,2 | Threonyl-tRNA Synthetase (mitochondrial) |

1. Condition 1: over expressed TARS; Condition 2: over-expressed TARS and over-expressed VHL

FIG. 16

SEQUENCE LISTING

```
<160> NUMBER OF SEQ ID NOS: 9

<210> SEQ ID NO 1
<211> LENGTH: 2888
<212> TYPE: DNA
<213> ORGANISM: Homo sapiens

<400> SEQUENCE: 1
```

```
ggtcagcgga gagtaggcat gtagcttctg cagttgctcc tcctcaccct ccgcgacctg    60
atttcctaga agggctctgt cacccgaaaa gattttccac tggcttagag gagggagggc   120
ccgccttccc ccgttatcca ttggctgctc gttccgccgc aagttggggg cggggttagg   180
gcgcctttcg attgcatcag ctggtccagc cgaggccaag tcccgggcgc tagcccacct   240
cccacccgcc tcttggctcc tctcctctag gccgtcgctt tcgggttctc tcatcgcttc   300
gtcgttcgcc aatgtttgag gagaaggcca gcagtccttc agggaagatg ggaggcgagg   360
agaagccgat tggtgctggt gaagagaagc aaaaggaagg aggcaaaaag aagaacaaag   420
aaggatctgg agatggaggt cgagctgagt tgaatccttg gcctgaatat atttacacac   480
gtcttgagat gtataatata ctaaaagcag aacatgattc cattctggca gaaaaggcag   540
aaaaagatag caagccaatt aaagtcactt tgcctgatgg taaacaggtt gatgcggaat   600
cttggaaaac tacaccatat caaattgcct gtggaattag tcaaggcctg ccgacaaca   660 ccgttattgc taaagtaaat aatgttgtgt gggacctgga ccgccctctg gaagaagatt   720
gtaccttgga gcttctcaag tttgaggatg aggaagctca ggcagtgtat tggcactcta   780
gtgctcacat aatgggtgaa gccatggaaa gagtctatgg tggatgttta tgctacggtc   840
cgccaataga aaatggattc tattatgaca tgtacctcga agaaggggt gtgtctagca   900 atgatttctc ttctctggag gctttgtgta agaaaatcat taagaaaaa caagcttttg   960 aaagactgga agttaagaaa gaaactttac tggcaatgtt taagtacaac aagttcaaat  1020
gccggatatt gaatgaaaag gtgaatactc caactaccac agtctataga tgtggcccct  1080
tgatagatct ctgccggggt cctcatgtta gacacacggg caaaattaag gctttaaaaa  1140
tacacaaaaa ttcctccacg tactgggaag caaagcaga tatggagact ctccagagaa  1200
tttatggcat ttcattccca gatcctaaaa tgttgaaaga gtgggagaag ttccaagagg  1260
aagctaaaaa ccgagatcat aggaaaattg gcagggacca agaactatat ttctttcatg  1320
aactcagccc tggaagttgc ttttttctgc caaaaggagc ctacatttat aatgcactta  1380
ttgaattcat taggagcgaa ataggaaaa gaggattcca ggaggtagtc accccaaaca  1440
tcttcaacag ccgactctgg atgaccttgg gccactggca gcactacagc gagaacatgt  1500
tctcctttga ggtggagaag gagctgtttg ccctgaaacc catgaactgc caggacact  1560 gccttatgtt tgatcatcgg ccaaggtcct ggcgagaact gcctctgcgg ctagctgatt  1620
ttggggtact tcataggaac gagctgtctg gagcactcac aggactcacc cgggtacgaa  1680
gattccaaca ggatgatgct cacatattct gtgccatgga gcagattgaa gatgaaataa  1740
aaggttgttt ggattttcta cgtacggtat atagcgtatt tggattttct tttaaactaa  1800 accttttctac tcgcccggaa aaattccttg gagatatcga agtatgggat caagctgaga  1860
aacaacttga aaacagtctg aatgaatttg gtgaaaagtg ggagttaaac tctggagatg  1920
gagctttcta tggcccaaag attgacatac agattaaaga tgcgattggg cggtaccacc  1980
agtgtgcaac catccagctg gatttccagt tgcccatcag atttaatctt acttatgtaa  2040
gccatgatgg tgatgataag aaaaggccag tgattgttca tcgagccatc ttgggatcag  2100
tggaaagaat gattgctatc ctcacagaaa actatggggg caaatggccc ttttggctgt  2160
cccctcgcca ggtaatggta gttccagtgg gaccaacctg tgatgaatat gcccaaaagg  2220
tacgacaaca attccacgat gccaaattca tggcagacat tgatctggat ccaggctgta  2280
cattgaataa aaagattcga aatgcacagt tagcacagta taacttcatt ttagttgttg  2340
```

```
gtgaaaaaga gaaaatcagt ggcactgtta atatccgcac aagagacaat aaggtccacg    2400
gggaacgcac catttctgaa actatcgagc ggctacagca gctcaaagag ttccgcagca    2460
aacaggcaga agaagaattt taatgaaaaa attacccaga ttggctccat ggaaaaggag    2520
gaacagcgtt tccgtaaaat tgactttgta ctctgaaaac gtcaatttat attgaacttg    2580
gaggagtttg gcaaagtctg aataggtcaa cctgcaggcg taactatttt tgacctagtc    2640 agttttttaaa caatgtgcat ttgaaggagt taattaaaag agagccaata aaatgatttt    2700
actcattcag tatctgagta ctggaagtga aacatgagga atgctttagt gtaatgtggg    2760
agaacttttt tgtaaaattta atgcaattga aaaagttttc aaattcaatt aagataacta    2820
gaattggatt atggtgtaaa aataaaaaaa aaatttattc acataaaaaa aaaaaaaaa    2880 aaaaaaaa    2888
```

<210> SEQ ID NO 2
<211> LENGTH: 723
<212> TYPE: PRT
<213> ORGANISM: Homo sapiens

<400> SEQUENCE: 2

```
Met Phe Glu Glu Lys Ala Ser Ser Pro Ser Gly Lys Met Gly Gly Glu
1               5                   10                  15

Glu Lys Pro Ile Gly Ala Gly Glu Lys Gln Lys Glu Gly Gly Lys
            20                  25                  30

Lys Lys Asn Lys Glu Gly Ser Gly Asp Gly Gly Arg Ala Glu Leu Asn
        35                  40                  45

Pro Trp Pro Glu Tyr Ile Tyr Thr Arg Leu Glu Met Tyr Asn Ile Leu
    50                  55                  60

Lys Ala Glu His Asp Ser Ile Leu Ala Glu Lys Ala Glu Lys Asp Ser
65                  70                  75                  80

Lys Pro Ile Lys Val Thr Leu Pro Asp Gly Lys Gln Val Asp Ala Glu
                85                  90                  95

Ser Trp Lys Thr Thr Pro Tyr Gln Ile Ala Cys Gly Ile Ser Gln Gly
            100                 105                 110

Leu Ala Asp Asn Thr Val Ile Ala Lys Val Asn Asn Val Val Trp Asp
        115                 120                 125

Leu Asp Arg Pro Leu Glu Glu Asp Cys Thr Leu Glu Leu Leu Lys Phe
    130                 135                 140

Glu Asp Glu Glu Ala Gln Ala Val Tyr Trp His Ser Ser Ala His Ile
145                 150                 155                 160

Met Gly Glu Ala Met Glu Arg Val Tyr Gly Cys Leu Cys Tyr Gly
                165                 170                 175

Pro Pro Ile Glu Asn Gly Phe Tyr Tyr Asp Met Tyr Leu Glu Glu Gly
            180                 185                 190

Gly Val Ser Ser Asn Asp Phe Ser Ser Leu Glu Ala Leu Cys Lys Lys
        195                 200                 205

Ile Ile Lys Glu Lys Gln Ala Phe Glu Arg Leu Glu Val Lys Lys Glu
    210                 215                 220

Thr Leu Leu Ala Met Phe Lys Tyr Asn Lys Phe Lys Cys Arg Ile Leu
225                 230                 235                 240

Asn Glu Lys Val Asn Thr Pro Thr Thr Thr Val Tyr Arg Cys Gly Pro
                245                 250                 255

Leu Ile Asp Leu Cys Arg Gly Pro His Val Arg His Thr Gly Lys Ile
            260                 265                 270
```

-continued

```
Lys Ala Leu Lys Ile His Lys Asn Ser Ser Thr Tyr Trp Glu Gly Lys
            275                 280                 285

Ala Asp Met Glu Thr Leu Gln Arg Ile Tyr Gly Ile Ser Phe Pro Asp
        290                 295                 300

Pro Lys Met Leu Lys Glu Trp Glu Lys Phe Gln Glu Glu Ala Lys Asn
305                 310                 315                 320

Arg Asp His Arg Lys Ile Gly Arg Asp Gln Glu Leu Tyr Phe Phe His
                325                 330                 335

Glu Leu Ser Pro Gly Ser Cys Phe Phe Leu Pro Lys Gly Ala Tyr Ile
            340                 345                 350

Tyr Asn Ala Leu Ile Glu Phe Ile Arg Ser Glu Tyr Arg Lys Arg Gly
        355                 360                 365

Phe Gln Glu Val Val Thr Pro Asn Ile Phe Asn Ser Arg Leu Trp Met
    370                 375                 380

Thr Ser Gly His Trp Gln His Tyr Ser Glu Asn Met Phe Ser Phe Glu
385                 390                 395                 400

Val Glu Lys Glu Leu Phe Ala Leu Lys Pro Met Asn Cys Pro Gly His
                405                 410                 415

Cys Leu Met Phe Asp His Arg Pro Arg Ser Trp Arg Glu Leu Pro Leu
            420                 425                 430

Arg Leu Ala Asp Phe Gly Val Leu His Arg Asn Glu Leu Ser Gly Ala
        435                 440                 445

Leu Thr Gly Leu Thr Arg Val Arg Arg Phe Gln Gln Asp Asp Ala His
    450                 455                 460

Ile Phe Cys Ala Met Glu Gln Ile Glu Asp Glu Ile Lys Gly Cys Leu
465                 470                 475                 480

Asp Phe Leu Arg Thr Val Tyr Ser Val Phe Gly Phe Ser Phe Lys Leu
                485                 490                 495

Asn Leu Ser Thr Arg Pro Glu Lys Phe Leu Gly Asp Ile Glu Val Trp
            500                 505                 510

Asp Gln Ala Glu Lys Gln Leu Glu Asn Ser Leu Asn Glu Phe Gly Glu
        515                 520                 525

Lys Trp Glu Leu Asn Ser Gly Asp Gly Ala Phe Tyr Gly Pro Lys Ile
    530                 535                 540

Asp Ile Gln Ile Lys Asp Ala Ile Gly Arg Tyr His Gln Cys Ala Thr
545                 550                 555                 560

Ile Gln Leu Asp Phe Gln Leu Pro Ile Arg Phe Asn Leu Thr Tyr Val
                565                 570                 575

Ser His Asp Gly Asp Lys Lys Arg Pro Val Ile Val His Arg Ala
            580                 585                 590

Ile Leu Gly Ser Val Glu Arg Met Ile Ala Ile Leu Thr Glu Asn Tyr
        595                 600                 605

Gly Gly Lys Trp Pro Phe Trp Leu Ser Pro Arg Gln Val Met Val Val
    610                 615                 620

Pro Val Gly Pro Thr Cys Asp Glu Tyr Ala Gln Lys Val Arg Gln Gln
625                 630                 635                 640

Phe His Asp Ala Lys Phe Met Ala Asp Ile Asp Leu Asp Pro Gly Cys
                645                 650                 655

Thr Leu Asn Lys Lys Ile Arg Asn Ala Gln Leu Ala Gln Tyr Asn Phe
            660                 665                 670

Ile Leu Val Val Gly Glu Lys Glu Lys Ile Ser Gly Thr Val Asn Ile
        675                 680                 685

Arg Thr Arg Asp Asn Lys Val His Gly Glu Arg Thr Ile Ser Glu Thr
```

```
              690                 695                 700
Ile Glu Arg Leu Gln Gln Leu Lys Glu Phe Arg Ser Lys Gln Ala Glu
705                 710                 715                 720

Glu Glu Phe

<210> SEQ ID NO 3
<211> LENGTH: 722
<212> TYPE: PRT
<213> ORGANISM: Mus musculus

<400> SEQUENCE: 3

Met Ser Gln Glu Lys Ala Ser Ser Pro Ser Gly Lys Met Asp Gly Glu
1               5                   10                  15

Lys Pro Val Asp Ala Ser Glu Glu Lys Arg Lys Glu Gly Gly Lys Lys
            20                  25                  30

Lys Ser Lys Asp Gly Gly Gly Asp Gly Gly Arg Ala Glu Leu Asn Pro
        35                  40                  45

Trp Pro Glu Tyr Ile Asn Thr Arg Leu Asp Met Tyr Asn Lys Leu Lys
    50                  55                  60

Ala Glu His Asp Ser Ile Leu Ala Glu Lys Ala Ala Lys Asp Ser Lys
65                  70                  75                  80

Pro Ile Lys Val Thr Leu Pro Asp Gly Lys Gln Val Asp Ala Glu Ser
                85                  90                  95

Trp Lys Thr Thr Pro Tyr Gln Ile Ala Cys Gly Ile Ser Gln Gly Leu
            100                 105                 110

Ala Asp Asn Thr Val Val Ala Lys Val Asn Lys Val Val Trp Asp Leu
        115                 120                 125

Asp Arg Pro Leu Glu Thr Asp Cys Thr Leu Glu Leu Leu Lys Phe Glu
    130                 135                 140

Asp Glu Glu Ala Gln Ala Val Tyr Trp His Ser Ser Ala His Ile Met
145                 150                 155                 160

Gly Glu Ala Met Glu Arg Val Tyr Gly Gly Cys Leu Cys Tyr Gly Pro
                165                 170                 175

Pro Ile Glu Asn Gly Phe Tyr Tyr Asp Met Tyr Leu Glu Glu Gly Gly
            180                 185                 190

Val Ser Ser Asn Asp Phe Ser Ser Leu Glu Thr Leu Cys Lys Lys Ile
        195                 200                 205

Ile Lys Glu Lys Gln Thr Phe Glu Arg Leu Glu Val Lys Lys Glu Thr
    210                 215                 220

Leu Leu Glu Met Phe Lys Tyr Asn Lys Phe Lys Cys Arg Ile Leu Asn
225                 230                 235                 240

Glu Lys Val Asn Thr Pro Thr Thr Val Tyr Arg Cys Gly Pro Leu
                245                 250                 255

Ile Asp Leu Cys Arg Gly Pro His Val Arg His Thr Gly Lys Ile Lys
            260                 265                 270

Thr Leu Lys Ile His Lys Asn Ser Ser Thr Tyr Trp Glu Gly Lys Ala
        275                 280                 285

Asp Met Glu Thr Leu Gln Arg Ile Tyr Gly Ile Ser Phe Pro Asp Pro
    290                 295                 300

Lys Leu Leu Lys Glu Trp Glu Lys Phe Gln Glu Ala Lys Asn Arg
305                 310                 315                 320

Asp His Arg Lys Ile Gly Arg Asp Gln Glu Leu Tyr Phe Phe His Glu
                325                 330                 335

Leu Ser Pro Gly Ser Cys Phe Phe Leu Pro Lys Gly Ala Tyr Ile Tyr
```

```
                340                 345                 350
Asn Thr Leu Met Glu Phe Ile Arg Ser Glu Tyr Arg Lys Arg Gly Phe
            355                 360                 365

Gln Glu Val Val Thr Pro Asn Ile Phe Asn Ser Arg Leu Trp Met Thr
370                 375                 380

Ser Gly His Trp Gln His Tyr Ser Glu Asn Met Phe Ser Phe Glu Val
385                 390                 395                 400

Glu Lys Glu Gln Phe Ala Leu Lys Pro Met Asn Cys Pro Gly His Cys
                405                 410                 415

Leu Met Phe Asp His Arg Pro Arg Ser Trp Arg Glu Leu Pro Leu Arg
                420                 425                 430

Leu Ala Asp Phe Gly Val Leu His Arg Asn Glu Leu Ser Gly Ala Leu
            435                 440                 445

Thr Gly Leu Thr Arg Val Arg Arg Phe Gln Gln Asp Asp Ala His Ile
        450                 455                 460

Phe Cys Ala Met Glu Gln Ile Glu Asp Glu Ile Lys Gly Cys Leu Asp
465                 470                 475                 480

Phe Leu Arg Thr Val Tyr Ser Val Phe Gly Phe Ser Phe Lys Leu Asn
                485                 490                 495

Leu Ser Thr Arg Pro Glu Lys Phe Leu Gly Asp Ile Glu Ile Trp Asn
            500                 505                 510

Gln Ala Glu Lys Gln Leu Glu Asn Ser Leu Asn Glu Phe Gly Glu Lys
        515                 520                 525

Trp Glu Leu Asn Pro Gly Asp Gly Ala Phe Tyr Gly Pro Lys Ile Asp
    530                 535                 540

Ile Gln Ile Lys Asp Ala Ile Gly Arg Tyr His Gln Cys Ala Thr Ile
545                 550                 555                 560

Gln Leu Asp Phe Gln Leu Pro Ile Arg Phe Asn Leu Thr Tyr Val Ser
                565                 570                 575

His Asp Gly Asp Asp Lys Lys Arg Pro Val Ile Val His Arg Ala Ile
            580                 585                 590

Leu Gly Ser Val Glu Arg Met Ile Ala Ile Leu Thr Glu Asn Tyr Gly
        595                 600                 605

Gly Lys Trp Pro Phe Trp Leu Ser Pro Arg Gln Val Met Val Val Pro
610                 615                 620

Val Gly Pro Thr Cys Asp Glu Tyr Ala Gln Lys Val Arg Gln Gln Phe
625                 630                 635                 640

His Asp Ala Lys Phe Met Ala Asp Thr Asp Leu Asp Pro Gly Cys Thr
                645                 650                 655

Leu Asn Lys Lys Ile Arg Asn Ala Gln Leu Ala Gln Tyr Asn Phe Ile
            660                 665                 670

Leu Val Val Gly Glu Lys Glu Lys Ala Ser Gly Thr Val Asn Ile Arg
        675                 680                 685

Thr Arg Asp Asn Lys Val His Gly Glu Arg Thr Val Glu Glu Thr Val
    690                 695                 700

Arg Arg Leu Gln Gln Leu Lys Gln Thr Arg Ser Lys Gln Ala Glu Glu
705                 710                 715                 720

Glu Phe

<210> SEQ ID NO 4
<211> LENGTH: 725
<212> TYPE: PRT
<213> ORGANISM: Caenorhabditis elegans
```

<400> SEQUENCE: 4

```
Met Arg Leu Asn Cys Phe Arg Ile Phe Val His Ile Gln Lys Pro Thr
1               5                   10                  15

Gln Ile Phe Lys Pro Phe Tyr Arg Ser Leu Ser Ser Glu Ala Ser Asp
            20                  25                  30

Lys Tyr His Phe Val Asn Gly His Met Ser Lys Ala Pro Thr Asp
        35                  40                  45

Met Ala Pro Trp Pro Ala Phe Ile Glu Glu Arg Ile Lys Leu Trp Asp
    50                  55                  60

Lys Leu Lys Ala Glu Tyr Asp Ala Glu Ile Ala Ala Lys Glu Ser Glu
65                  70                  75                  80

Pro Ile Gln Ile Thr Leu Pro Asp Gly Lys Ile His Glu Gly Lys Thr
                85                  90                  95

Trp Arg Thr Thr Pro Phe Glu Ile Ala Glu Arg Ile Ser Lys Gly Leu
            100                 105                 110

Ala Glu Ala Ala Val Ile Ala Lys Val Asn Gly Ala Val Trp Asp Leu
        115                 120                 125

Asp Arg Pro Phe Glu Gly Asn Ala Lys Leu Glu Leu Leu Lys Phe Asp
    130                 135                 140

Asp Asp Glu Ala Lys Gln Val Phe Trp His Ser Ser Ala His Val Leu
145                 150                 155                 160

Gly Glu Ala Met Glu Arg Tyr Cys Gly Gly His Leu Cys Tyr Gly Pro
                165                 170                 175

Pro Ile Gln Glu Gly Phe Tyr Tyr Asp Met Trp His Glu Asn Arg Thr
            180                 185                 190

Ile Cys Pro Asp Asp Phe Pro Lys Ile Asp Gln Ile Val Lys Ala Ala
        195                 200                 205

Val Lys Asp Lys Gln Lys Phe Glu Arg Leu Glu Met Thr Lys Glu Asp
210                 215                 220

Leu Leu Glu Met Phe Lys Tyr Asn Glu Phe Lys Val Arg Ile Ile Thr
225                 230                 235                 240

Glu Lys Ile His Thr Pro Lys Thr Thr Val Tyr Arg Cys Gly Pro Leu
                245                 250                 255

Ile Asp Leu Cys Arg Gly Pro His Val Arg His Thr Gly Lys Val Lys
            260                 265                 270

Ala Met Ala Ile Thr Lys Asn Ser Ser Tyr Trp Glu Gly Lys Ala
        275                 280                 285

Asp Ala Glu Ser Leu Gln Arg Leu Tyr Gly Ile Ser Phe Pro Asp Ser
    290                 295                 300

Lys Gln Leu Lys Glu Trp Gln Lys Leu Gln Glu Glu Ala Ala Lys Arg
305                 310                 315                 320

Asp His Arg Lys Leu Gly Lys Glu His Asp Leu Phe Phe His Gln
                325                 330                 335

Leu Ser Pro Gly Ser Ala Phe Trp Tyr Pro Lys Gly Ala His Ile Tyr
            340                 345                 350

Asn Lys Leu Val Asp Phe Ile Arg Lys Gln Tyr Arg Arg Arg Gly Phe
        355                 360                 365

Thr Glu Val Ile Thr Pro Asn Met Tyr Asn Lys Leu Trp Glu Thr
    370                 375                 380

Ser Gly His Trp Gln His Tyr Ser Glu Asp Met Phe Lys Ile Glu Val
385                 390                 395                 400

Glu Lys Glu Glu Phe Gly Leu Lys Pro Met Asn Cys Pro Gly His Cys
                405                 410                 415
```

-continued

Leu Met Phe Gly His Met Pro His Thr Tyr Asn Glu Leu Pro Phe Arg
        420                 425                 430

Phe Ala Asp Phe Gly Val Leu His Arg Asn Glu Met Ser Gly Ala Leu
        435                 440                 445

Thr Gly Leu Thr Arg Val Arg Arg Phe Gln Gln Asp Asp Ala His Ile
    450                 455                 460

Phe Cys Arg Gln Asp Gln Ile Ser Glu Glu Ile Lys Gln Cys Leu Asp
465                 470                 475                 480

Phe Leu Glu Tyr Ala Tyr Glu Lys Val Phe Gly Phe Thr Phe Lys Leu
            485                 490                 495

Asn Leu Ser Thr Arg Pro Glu Gly Phe Leu Gly Asn Ile Glu Thr Trp
        500                 505                 510

Asp Lys Ala Glu Ala Asp Leu Thr Asn Ala Leu Asn Ala Ser Gly Arg
        515                 520                 525

Lys Trp Val Leu Asn Pro Gly Asp Gly Ala Phe Tyr Gly Pro Lys Ile
    530                 535                 540

Asp Ile Thr Ile Gln Asp Ala Leu Lys Arg Asn Phe Gln Cys Ala Thr
545                 550                 555                 560

Ile Gln Leu Asp Phe Gln Leu Pro Asn Gln Phe Asp Leu Ser Tyr Phe
            565                 570                 575

Asp Glu Lys Gly Glu Lys Gln Arg Pro Val Met Ile His Arg Ala Val
        580                 585                 590

Leu Gly Ser Val Glu Arg Met Thr Ala Ile Leu Thr Glu Ser Tyr Gly
        595                 600                 605

Gly Lys Trp Pro Phe Trp Leu Ser Pro Arg Gln Cys Lys Ile Ile Thr
    610                 615                 620

Val His Glu Ser Val Arg Asp Tyr Ala Asn Asp Val Lys Lys Gln Ile
625                 630                 635                 640

Phe Glu Ala Gly Phe Glu Ile Glu Tyr Glu Glu Asn Cys Gly Asp Thr
            645                 650                 655

Met Asn Lys Gln Val Arg Lys Ala Gln Leu Ala Gln Phe Asn Phe Ile
        660                 665                 670

Leu Val Ile Gly Ala Lys Glu Lys Glu Asn Gly Thr Val Asn Val Arg
        675                 680                 685

Thr Arg Asp Asn Ala Val Arg Gly Glu Val Ala Leu Asp Lys Leu Ile
    690                 695                 700

Ser Lys Phe Arg Arg Phe Ala Asp Glu Tyr Val Ala Asp Thr Glu Lys
705                 710                 715                 720

Ser Glu Glu Trp Ala
            725

<210> SEQ ID NO 5
<211> LENGTH: 734
<212> TYPE: PRT
<213> ORGANISM: Saccharomyces cerevisiae

<400> SEQUENCE: 5

Met Ser Ala Ser Glu Ala Gly Val Thr Glu Gln Val Lys Lys Leu Ser
1               5                   10                  15

Val Lys Asp Ser Ser Asn Asp Ala Val Lys Pro Asn Lys Lys Glu Asn
            20                  25                  30

Lys Lys Ser Lys Gln Gln Ser Leu Tyr Leu Asp Pro Glu Pro Thr Phe
        35                  40                  45

Ile Glu Glu Arg Ile Glu Met Phe Asp Arg Leu Gln Lys Glu Tyr Asn

```
            50                  55                  60
Asp Lys Val Ala Ser Met Pro Arg Val Pro Leu Lys Ile Val Leu Lys
 65                  70                  75                  80

Asp Gly Ala Val Lys Glu Ala Thr Ser Trp Glu Thr Thr Pro Met Asp
                     85                  90                  95

Ile Ala Lys Gly Ile Ser Lys Ser Leu Ala Asp Arg Leu Cys Ile Ser
                    100                 105                 110

Lys Val Asn Gly Gln Leu Trp Asp Leu Asp Arg Pro Phe Glu Gly Glu
                115                 120                 125

Ala Asn Glu Glu Ile Lys Leu Glu Leu Leu Asp Phe Glu Ser Asp Glu
130                 135                 140

Gly Lys Lys Val Phe Trp His Ser Ser Ala His Val Leu Gly Glu Ser
145                 150                 155                 160

Cys Glu Cys His Leu Gly Ala His Ile Cys Leu Gly Pro Pro Thr Asp
                165                 170                 175

Asp Gly Phe Phe Tyr Glu Met Ala Val Arg Asp Ser Met Lys Asp Ile
            180                 185                 190

Ser Glu Ser Pro Glu Arg Thr Val Ser Gln Ala Asp Phe Pro Gly Leu
            195                 200                 205

Glu Gly Val Ala Lys Asn Val Ile Lys Gln Lys Gln Lys Phe Glu Arg
210                 215                 220

Leu Val Met Ser Lys Glu Asp Leu Leu Lys Met Phe His Tyr Ser Lys
225                 230                 235                 240

Tyr Lys Thr Tyr Leu Val Gln Thr Lys Val Pro Asp Gly Gly Ala Thr
                245                 250                 255

Thr Val Tyr Arg Cys Gly Lys Leu Ile Asp Leu Cys Val Gly Pro His
                260                 265                 270

Ile Pro His Thr Gly Arg Ile Lys Ala Phe Lys Leu Leu Lys Asn Ser
            275                 280                 285

Ser Cys Tyr Phe Leu Gly Asp Ala Thr Asn Asp Ser Leu Gln Arg Val
        290                 295                 300

Tyr Gly Ile Ser Phe Pro Asp Lys Lys Leu Met Asp Ala His Leu Lys
305                 310                 315                 320

Phe Leu Ala Glu Ala Ser Met Arg Asp His Arg Lys Ile Gly Lys Glu
                325                 330                 335

Gln Glu Leu Phe Leu Phe Asn Glu Met Ser Pro Gly Ser Cys Phe Trp
                340                 345                 350

Leu Pro His Gly Thr Arg Ile Tyr Asn Thr Leu Val Asp Leu Leu Arg
            355                 360                 365

Thr Glu Tyr Arg Lys Arg Gly Tyr Glu Glu Val Ile Thr Pro Asn Met
    370                 375                 380

Tyr Asn Ser Lys Leu Trp Glu Thr Ser Gly His Trp Ala Asn Tyr Lys
385                 390                 395                 400

Glu Asn Met Phe Thr Phe Glu Val Glu Lys Glu Thr Phe Gly Leu Lys
                405                 410                 415

Pro Met Asn Cys Pro Gly His Cys Leu Met Phe Lys Ser Arg Glu Arg
                420                 425                 430

Ser Tyr Arg Glu Leu Pro Trp Arg Val Ala Asp Phe Gly Val Ile His
        435                 440                 445

Arg Asn Glu Phe Ser Gly Ala Leu Ser Gly Leu Thr Arg Val Arg Arg
    450                 455                 460

Phe Gln Gln Asp Asp Ala His Ile Phe Cys Thr His Asp Gln Ile Glu
465                 470                 475                 480
```

Ser Glu Ile Glu Asn Ile Phe Asn Phe Leu Gln Tyr Ile Tyr Gly Val
            485                 490                 495

Phe Gly Phe Glu Phe Lys Met Glu Leu Ser Thr Arg Pro Glu Lys Tyr
        500                 505                 510

Val Gly Lys Ile Glu Thr Trp Asp Ala Ala Glu Ser Lys Leu Glu Ser
        515                 520                 525

Ala Leu Lys Lys Trp Gly Gly Asn Trp Glu Ile Asn Ala Gly Asp Gly
    530                 535                 540

Ala Phe Tyr Gly Pro Lys Ile Asp Ile Met Ile Ser Asp Ala Leu Arg
545                 550                 555                 560

Arg Trp His Gln Cys Ala Thr Ile Gln Leu Asp Phe Gln Leu Pro Asn
                565                 570                 575

Arg Phe Glu Leu Glu Phe Lys Ser Lys Asp Gln Asp Ser Glu Ser Tyr
            580                 585                 590

Glu Arg Pro Val Met Ile His Arg Ala Ile Leu Gly Ser Val Glu Arg
        595                 600                 605

Met Thr Ala Ile Leu Thr Glu His Phe Ala Gly Lys Trp Pro Phe Trp
    610                 615                 620

Leu Ser Pro Arg Gln Val Leu Val Val Pro Val Gly Val Lys Tyr Gln
625                 630                 635                 640

Gly Tyr Ala Glu Asp Val Arg Asn Lys Leu His Asp Ala Gly Phe Tyr
                645                 650                 655

Ala Asp Val Asp Leu Thr Gly Asn Thr Leu Gln Lys Lys Val Arg Asn
            660                 665                 670

Gly Gln Met Leu Lys Tyr Asn Phe Ile Phe Ile Val Gly Glu Gln Glu
        675                 680                 685

Met Asn Glu Lys Ser Val Asn Ile Arg Asn Arg Asp Val Met Glu Gln
    690                 695                 700

Gln Gly Lys Asn Ala Thr Val Ser Val Glu Glu Val Leu Lys Gln Leu
705                 710                 715                 720

Arg Asn Leu Lys Asp Glu Lys Arg Gly Asp Asn Val Leu Ala
                725                 730

<210> SEQ ID NO 6
<211> LENGTH: 723
<212> TYPE: PRT
<213> ORGANISM: Homo sapiens

<400> SEQUENCE: 6

Met Phe Glu Glu Lys Ala Ser Ser Pro Ser Gly Lys Met Gly Gly Glu
1               5                   10                  15

Glu Lys Pro Ile Gly Ala Gly Glu Glu Lys Gln Lys Glu Gly Gly Lys
            20                  25                  30

Lys Lys Asn Lys Glu Gly Ser Gly Asp Gly Gly Arg Ala Glu Leu Asn
        35                  40                  45

Pro Trp Pro Glu Tyr Ile Tyr Thr Arg Leu Glu Met Tyr Asn Ile Leu
    50                  55                  60

Lys Ala Glu His Asp Ser Ile Leu Ala Glu Lys Ala Glu Lys Asp Ser
65                  70                  75                  80

Lys Pro Ile Lys Val Thr Leu Pro Asp Gly Lys Gln Val Asp Ala Glu
                85                  90                  95

Ser Trp Lys Thr Thr Pro Tyr Gln Ile Ala Cys Gly Ile Ser Gln Gly
            100                 105                 110

Leu Ala Asp Asn Thr Val Ile Ala Lys Val Asn Asn Val Val Trp Asp

-continued

```
            115                 120                 125
Leu Asp Arg Pro Leu Glu Glu Asp Cys Thr Leu Glu Leu Leu Lys Phe
        130                 135                 140
Glu Asp Glu Glu Ala Gln Ala Val Tyr Trp His Ser Ser Ala His Ile
145                 150                 155                 160
Met Gly Glu Ala Met Glu Arg Val Tyr Gly Cys Leu Cys Tyr Gly
                165                 170                 175
Pro Pro Ile Glu Asn Gly Phe Tyr Tyr Asp Met Tyr Leu Glu Glu Gly
                180                 185                 190
Gly Val Ser Ser Asn Asp Phe Ser Ser Leu Glu Ala Leu Cys Lys Lys
            195                 200                 205
Ile Ile Lys Glu Lys Gln Ala Phe Glu Arg Leu Glu Val Lys Lys Glu
        210                 215                 220
Thr Leu Leu Ala Met Phe Lys Tyr Asn Lys Phe Lys Cys Arg Ile Leu
225                 230                 235                 240
Asn Glu Lys Val Asn Thr Pro Thr Thr Thr Val Tyr Arg Cys Gly Pro
                245                 250                 255
Leu Ile Asp Leu Cys Arg Gly Pro His Val Arg His Thr Gly Lys Ile
                260                 265                 270
Lys Ala Leu Lys Ile His Lys Asn Ser Ser Thr Tyr Trp Glu Gly Lys
            275                 280                 285
Ala Asp Met Glu Thr Leu Gln Arg Ile Tyr Gly Ile Ser Phe Pro Asp
        290                 295                 300
Pro Lys Met Leu Lys Glu Trp Glu Lys Phe Gln Glu Glu Ala Lys Asn
305                 310                 315                 320
Arg Asp His Arg Lys Ile Gly Arg Asp Gln Glu Leu Tyr Phe Phe His
                325                 330                 335
Glu Leu Ser Pro Gly Ser Cys Phe Phe Leu Pro Lys Gly Ala Tyr Ile
                340                 345                 350
Tyr Asn Ala Leu Ile Glu Phe Ile Arg Ser Glu Tyr Arg Lys Arg Gly
            355                 360                 365
Phe Gln Glu Val Val Thr Pro Asn Ile Phe Asn Ser Arg Leu Trp Met
        370                 375                 380
Thr Ser Gly His Trp Gln His Tyr Ser Glu Asn Met Phe Ser Phe Glu
385                 390                 395                 400
Val Glu Lys Glu Leu Phe Ala Leu Lys Pro Met Asn Cys Pro Gly His
                405                 410                 415
Cys Leu Met Phe Asp His Arg Pro Arg Ser Trp Arg Glu Leu Pro Leu
                420                 425                 430
Arg Leu Ala Asp Phe Gly Val Leu His Arg Asn Glu Leu Ser Gly Ala
            435                 440                 445
Leu Thr Gly Leu Thr Arg Val Arg Arg Phe Gln Gln Asp Asp Ala His
        450                 455                 460
Ile Phe Cys Ala Met Glu Gln Ile Glu Asp Glu Ile Lys Gly Cys Leu
465                 470                 475                 480
Asp Phe Leu Arg Thr Val Tyr Ser Val Phe Gly Phe Ser Phe Lys Leu
                485                 490                 495
Asn Leu Ser Thr Arg Pro Glu Lys Phe Leu Gly Asp Ile Glu Val Trp
                500                 505                 510
Asp Gln Ala Glu Lys Gln Leu Glu Asn Ser Leu Asn Glu Phe Gly Glu
            515                 520                 525
Lys Trp Glu Leu Asn Ser Gly Asp Gly Ala Phe Tyr Gly Pro Lys Ile
        530                 535                 540
```

Asp Ile Gln Ile Lys Asp Ala Ile Gly Arg Tyr His Gln Cys Ala Thr
545                 550                 555                 560

Ile Gln Leu Asp Phe Gln Leu Pro Ile Arg Phe Asn Leu Thr Tyr Val
                565                 570                 575

Ser His Asp Gly Asp Lys Lys Arg Pro Val Ile Val His Arg Ala
            580                 585                 590

Ile Leu Gly Ser Val Glu Arg Met Ile Ala Ile Leu Thr Glu Asn Tyr
            595                 600                 605

Gly Gly Lys Trp Pro Phe Trp Leu Ser Pro Arg Gln Val Met Val Val
            610                 615                 620

Pro Val Gly Pro Thr Cys Asp Glu Tyr Ala Gln Lys Val Arg Gln Gln
625                 630                 635                 640

Phe His Asp Ala Lys Phe Met Ala Asp Ile Asp Leu Asp Pro Gly Cys
                645                 650                 655

Thr Leu Asn Lys Lys Ile Arg Asn Ala Gln Leu Ala Gln Tyr Asn Phe
                660                 665                 670

Ile Leu Val Val Gly Glu Lys Glu Lys Ile Ser Gly Thr Val Asn Ile
            675                 680                 685

Arg Thr Arg Asp Asn Lys Val His Gly Glu Arg Thr Ile Ser Glu Thr
690                 695                 700

Ile Glu Arg Leu Gln Gln Leu Lys Glu Phe Arg Ser Lys Gln Ala Glu
705                 710                 715                 720

Glu Glu Phe

<210> SEQ ID NO 7
<211> LENGTH: 100
<212> TYPE: PRT
<213> ORGANISM: Homo sapiens

<400> SEQUENCE: 7

Arg Ala Glu Leu Asn Pro Trp Pro Glu Tyr Ile Tyr Thr Arg Leu Glu
1               5                   10                  15

Met Tyr Asn Ile Leu Lys Ala Glu His Asp Ser Ile Leu Ala Glu Lys
            20                  25                  30

Ala Glu Lys Asp Ser Lys Pro Ile Lys Val Thr Leu Pro Asp Gly Lys
        35                  40                  45

Gln Val Asp Ala Glu Ser Trp Lys Thr Thr Pro Tyr Gln Ile Ala Cys
    50                  55                  60

Gly Ile Ser Gln Gly Leu Ala Asp Asn Thr Val Ile Ala Lys Val Asn
65                  70                  75                  80

Asn Val Val Trp Asp Leu Asp Arg Pro Leu Glu Glu Asp Cys Thr Leu
                85                  90                  95

Glu Leu Leu Lys
            100

<210> SEQ ID NO 8
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 8
caccagtgtg caaccatcca gctggatttc caggtgccca tcagatttaa tc        52

<210> SEQ ID NO 9

```
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 9
gattaaatct gatgggccac tggaaatcca gctggatggt tgcacactgg tg              52
```

METHODS AND COMPOUNDS FOR DIAGNOSING THREONYL-TRNA SYNTHETASE-ASSOCIATED DISEASES AND CONDITIONS

RELATED APPLICATIONS

This application is a Divisional of U.S. patent application Ser. No. 14/416,347, filed on Jan. 22, 2015, now pending, which is a National Stage Filing under U.S.C. § 371 of PCT International Application PCT/US2013/51806, filed Jul. 24, 2013 which was published under PCT Article 21(2) in English, which claims benefit under 35 U.S.C. § 119(e) of U.S. Provisional Application No. 61/675,652, filed Jul. 25, 2012 and the content of each of which is incorporated by reference herein in its entirety.

GOVERNMENT INTEREST

This invention was made with government support under RO1 GM54899 and by training grant T32 ES007122-23 both awarded by the National Institutes of Health. The government has certain rights in the invention.

FIELD OF THE INVENTION

The invention relates, in part, to methods and compounds for diagnosing diseases and conditions associated with altered threonyl-tRNA synthetase (TARS) activity in a subject.

BACKGROUND

Angiogenesis plays a role in diseases such as cancer and other proliferative disorders. For example, a small solid tumor may be able to survive in the absence of vascularization, but to provide sufficient nutrients and oxygen and to remove waste products from cells that make up larger tumors, vascularization of the tissue is necessary. Triggers and regulators of angiogenesis in cells and tissues are not fully understood, but it is thought that hypoxia and lack of adequate nutritional access in cells in tumors greater than approximately 2 cm$^3$ in size may result in angiogenesis, which supports further tumor growth with increased delivery of oxygen and nutrients. Angiogenesis may be a factor in the progression of a tumor or cancer, not only by providing nutrient support for a tumor to continue to grow in size, but angiogenesis may also play a role in metastatic activity in some cancers.

Angiogenesis has emerged as a target for cancer therapy due to the reliance of many cancers on new vessels and the poor prognosis associated with cancers that have advanced angiogenesis (Folkman, J. (2001) Semin Oncol 28 (6), 536-542). Angiogenesis is normally suppressed by angiopoietin-1 which is secreted by vascular pericytes and inhibits endothelial cell proliferation. There are many factors involved in the tumor angiogenic switch, but initiation of angiogenesis by hypoxic tumor cells is primarily through induction of hypoxia inducible factor-1α (HIF-1α) which stimulates expression of vascular endothelial growth factor (VEGF). VEGF acts in combination with other growth factors and receptors to increase activation of the Ras/MAP kinase and phosphoinositide 3 kinase (PI3 kinase) pathways in endothelial cells. These pathways are involved in induction of genes involved in endothelial cell proliferation and migration. (Bikfalvi, A. and Bicknell, R. (2002) Trends in Pharmacological Sciences 23 (12), 576-582; Liao, D. and Johnson, R. (2007) Cancer and Metastasis Reviews 26 (2), 281-290; and Olsson, A. K. et al. (2006) Nat Rev Mol Cell Biol 7 (5), 359-371).

Cell and tissue growth, for example vascular growth in angiogenesis, are known to involve protein synthesis but processes involved in the initiation, regulation, and modulation of protein synthesis in angiogenesis appear to be quite complex and are not well understood. The lack of understanding of the complex pathways and interactive regulatory events necessary to trigger and support angiogenesis in cells limits approaches to diagnose disorders that are characterized, in part, by angiogenesis.

SUMMARY OF THE INVENTION

The invention includes, in part, methods and compounds for diagnosing diseases and conditions characterized by altered threonyl-tRNA synthetase (TARS) activity, which include, but are not limited to diseases and conditions in which angiogenesis is altered. In some embodiments of the invention, a level of a TARS molecule is determined and compared to a control level of TARS to assess onset, progression, and/or regression of a disease or condition associated with altered TARS activity.

It has now been shown for the first time that TARS is a potent angiogenic inducer in vitro and in vivo affecting endothelial cell migration and tube formation. TARS is also shown to be secreted by endothelial cells in response to angiogenic or inflammatory signaling, indicating its novel role as a pro-angiogenic chemokine. Furthermore, an association is revealed between TARS levels and both ovarian and prostate cancers in human patient samples.

According to an aspect of the invention, methods of diagnosing a subject as having, or at increased risk of developing a disorder associated with increased threonyl-tRNA synthetase (TARS) activity are provided. The methods include (a) obtaining a biological sample from a subject; (b) measuring the amount of a TARS molecule in the biological sample; and (c) comparing the level of the TARS molecule in the biological sample to a normal control level of the TARS molecule, wherein a significant increase in the level of the TARS molecule in the subject biological sample compared to the normal control level is an indication that the subject has or is at increased risk of developing the disorder associated with increased TARS activity. In some embodiments, a significant increase in the level of the TARS molecule in the subject sample compared to the control determines that the subject is at increased risk of developing a disorder associated with increased TARS activity. In certain embodiments, the normal control is a level of the TARS molecule characteristic of biological samples from individuals free of the disorder associated with increased TARS activity. In some embodiments, the level of the TARS molecule is measured by measuring a secreted TARS molecule. In some embodiments, the level of the TARS molecule is measured by measuring a non-secreted TARS molecule. In certain embodiments, the level of the TARS molecule is measured by measuring the activity of the TARS molecule. In some embodiments, the disorder associated with increased TARS activity is an angiogenesis-associated disorder. In some embodiments, the angiogenesis-associated disorder is a cancer, a tumor, a hemangioma, vascular overgrowth, venous malformation, arterial malformation, overweight, macular degeneration, inflammatory disease, psoriasis, diabetes, or rheumatoid arthritis. In some embodiments, the cancer is a metastatic carcinoma of the cervix; sarcoma of the kidney; renal cell carcinoma; prostate cancer;

androgen independent prostate cancer; Kaposi's sarcoma; colorectal cancer, hepatobilliary cancer, gastric cancer, epithelial ovarian cancer; lung cancer, or mesothelioma. In certain embodiments, the cancer is a metastatic cancer. In some embodiments, the biological sample is a sample of blood, tissue, serum, urine, stool, sputum, cerebrospinal fluid, or supernatant from cell lysate. In some embodiments, the biological sample includes a cell or tissue. In certain embodiments, the TARS molecule includes a TARS polypeptide. In some embodiments, the TARS molecule includes a TARS-encoding nucleic acid. In certain embodiments, a means of the measuring includes an immunological assay, nucleic acid determination, mass spectrometry, TARS aminoacylation assay, TARS active site determination assay, or a TARS binding assay including a TARS-binding reporter molecule. In some embodiments, the immunological assay includes an ELISA assay. In some embodiments, the method also includes selecting a treatment regimen for the subject based at least in part on the comparison of the level of the TARS molecule in the biological sample to the normal control level of the TARS molecule. In some embodiments, the treatment regimen includes administering one or more of a medicament, surgery, radiation, or chemotherapy to the subject. In certain embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the diagnosis.

According to another aspect of the invention, methods of diagnosing a subject as having, or at increased risk of developing, a disorder associated with increased threonyl-tRNA synthetase (TARS) activity are provided. The methods include (a) obtaining a biological sample from a subject; (b) measuring the amount of a TARS molecule in the biological sample; and (c) comparing the level of the TARS molecule in the biological sample to a disease control level of the TARS molecule, wherein a similar level of the TARS molecule in the subject biological sample compared to the disease control level is an indication that the subject has or is at increased risk of developing the disorder associated with increased TARS activity. In certain embodiments, the disease control level is a level of the TARS molecule characteristic of biological samples from individuals having the disorder associated with increased TARS activity. In some embodiments, the level of the TARS molecule is measured by measuring a secreted TARS molecule. In some embodiments, the level of the TARS molecule is measured by measuring a non-secreted TARS molecule. In some embodiments, the level of the TARS molecule is measured by measuring the activity of TARS. In certain embodiments, the disorder associated with increased TARS activity is an angiogenesis-associated disorder. In some embodiments, the angiogenesis-associated disorder is a cancer, a tumor, a hemangioma, vascular overgrowth, venous malformation, arterial malformation, overweight, macular degeneration, inflammatory disease, psoriasis, diabetes, or rheumatoid arthritis. In some embodiments, the cancer is a metastatic carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, or mesothelioma. In some embodiments, the cancer is a metastatic cancer. In certain embodiments, the biological sample is a sample of blood, tissue, serum, urine, stool, sputum, cerebrospinal fluid, or supernatant from cell lysate. In some embodiments, the biological sample includes a cell or tissue. In some embodiments, the TARS molecule is a TARS polypeptide. In some embodiments, the TARS molecule is a TARS-encoding nucleic acid. In certain embodiments, a means for the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In some embodiments, the method also includes selecting a treatment regimen for the subject based at least in part on the comparison of the level of the TARS molecule in the biological sample to the normal control level of the TARS molecule. In some embodiments, the treatment regimen includes administering one or more of a medicament, surgery, radiation, or chemotherapy to the subject. In certain embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the diagnosis.

According to another aspect of the invention, methods for determining a prognosis in a subject diagnosed with a disorder associated with increased threonyl-tRNA synthetase (TARS) activity are provided. The methods include (a) obtaining a biological sample from the subject; (b) measuring a TARS molecule level in the subject's biological sample; (c) comparing the TARS molecule level of the subject's sample with a control level of the TARS molecule; and (d) correlating levels of the TARS molecule greater than the control level with an indication of unfavorable prognosis and levels of the TARS molecule at or below the control level with a favorable prognosis. In certain embodiments, the disorder associated with increased TARS activity is an angiogenesis-associated disorder. In some embodiments, the angiogenesis-associated disorder is a cancer, a tumor, a hemangioma, vascular overgrowth, venous malformation, arterial malformation, overweight, macular degeneration, inflammatory disease, psoriasis, diabetes, or rheumatoid arthritis. In some embodiments, the cancer is a metastatic carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, or mesothelioma. In some embodiments, the cancer is a metastatic cancer. In certain embodiments, the TARS molecule is a TARS protein. In some embodiments, the TARS molecule is a TARS-encoding nucleic acid. In some embodiments, a means of the measuring includes an immunological assay, nucleotide determination (mRNA or DNA), mass spectrometry, TARS aminoacylation assay, TARS active site determination assay, or a TARS binding assay including a TARS-binding reporter molecule, or an ELISA assay. In certain embodiments, the method also includes selecting a treatment regimen for the subject based at least in part on the determined prognosis. In some embodiments, the treatment regimen includes administering one or more of a medicament, surgery, radiation, or chemotherapy to the subject. In certain embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the prognosis determined.

According to another aspect of the invention, methods of determining the onset, progression, or regression in a subject of a disorder associated with increased threonyl-tRNA synthetase (TARS) activity are provided. The methods include (a) obtaining a first biological sample from a subject; (b) measuring the level of a TARS molecule in the first biological sample; (c) obtaining a second biological sample from the subject; (d) measuring the amount of the TARS molecule in the second biological sample obtained from the subject, wherein the second biological sample is obtained from the subject at a time subsequent to the time the first biological sample is obtained; and (e) comparing the measurement of the TARS molecule in the first biological sample to the measurement of the TARS molecule in the second biological sample as a determination of the onset, progression, or regression of the disorder associated with increased TARS activity. In some embodiments, an increase in the level of the TARS molecule in the second sample compared to the first sample indicates the onset or progression of the disorder. In certain embodiments, a decrease in the level of the TARS molecule in the second sample compared to the first sample indicates the regression of the disorder. In some embodiments, the disorder associated with increased TARS activity is an angiogenesis-associated disorder. In some embodiments, the angiogenesis-associated disorder is a cancer, a tumor, a hemangioma, vascular overgrowth, venous malformation, arterial malformation, overweight, macular degeneration, inflammatory disease, psoriasis, diabetes, or rheumatoid arthritis. In certain embodiments, the cancer is a metastatic carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, or mesothelioma. In some embodiments, the cancer is a metastatic cancer. In some embodiments, the TARS molecule is a TARS protein. In some embodiments, the TARS molecule is a TARS-encoding nucleic acid. In certain embodiments, a means of the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In some embodiments, the method also includes selecting a treatment regimen for the subject based at least in part on the determination of the onset, progression or regression of the disorder. In some embodiments, the treatment regimen includes administering one or more of a medicament, surgery, radiation, or chemotherapy to the subject. In certain embodiments, the treatment regimen includes stopping a prior administration of one or more of a medicament, surgery, radiation, or chemotherapy. In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the determined onset, progression or regression of the of the disorder.

According to yet another aspect of the invention, methods for determining the metastatic potential of a cancer are provided. The methods include (a) obtaining a biological sample from a subject having a cancer; (b) measuring a level of a threonyl-tRNA synthetase (TARS) molecule in the biological sample; and (c) comparing the level of the TARS molecule in the biological sample to a control level of the TARS molecule, wherein a significantly higher level of the TARS molecule in the sample compared to the control level of the TARS molecule indicates a higher metastatic potential for the cancer. In some embodiments, the cancer is a carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, or mesothelioma. In some embodiments, the TARS molecule is a TARS protein. In certain embodiments, the TARS molecule is a TARS-encoding nucleic acid. In some embodiments, a means for the measuring includes an immunological assay, nucleotide determination (mRNA or DNA), mass spectrometry, TARS aminoacylation, GTPase, or Ap4A synthesis assay, TARS active site determination assay, a TARS binding assay including a TARS-binding reporter molecule, or an ELISA assay. In some embodiments, the method also includes selecting a treatment regimen for the subject based at least in part on the determined metastatic potential. In certain embodiments, the treatment regimen includes administering one or more of a medicament, surgery, radiation, or chemotherapy to the subject. In some embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the determined metastatic potential.

According to another aspect of the invention, methods of diagnosing a subject as having, or is at increased risk of developing, a disorder associated with decreased threonyl-tRNA synthetase (TARS) activity are provided. The methods include (a) obtaining a biological sample from a subject; (b) measuring the amount of a TARS molecule in the biological sample; (c) comparing the level of the TARS molecule in the biological sample to a normal control level of the TARS molecule, wherein a significant decrease in the level of the TARS molecule in the subject biological sample compared to the normal control level is an indication that the subject has or is at increased risk of developing the disorder associated with decreased TARS activity. In certain embodiments, a significant decrease in the level of the TARS molecule in the subject sample compared to the control determines that the subject is at risk of developing a disorder associated with decreased TARS activity. In some embodiments, the normal control is a level of the TARS molecule characteristic of biological samples from individuals free of the disorder associated with decreased TARS activity. In some embodiments, the level of the TARS molecule is measured by measuring a secreted TARS molecule. In certain embodiments, the level of the TARS molecule is measured by measuring a non-secreted TARS molecule. In some embodiments, the level of the TARS molecule is measured by measuring the activity of the TARS molecule. In some embodiments, the disorder associated with decreased TARS activity is an angiogenesis-associated disorder. In some embodiments, the subject has or is at risk of having an angiogenesis-associated disease or condition. In certain embodiments, the angiogenesis-associated disease or condition is a tissue implant, organ implant, ischemia, peripheral vascular disease, diabetes, cardiac infarction, tissue trauma, cartilage to bone transformation, stroke, surgery, pregnancy, macular degeneration, or vascular occlusion. In some embodiments, the biological sample is a sample of blood, tissue, serum, urine, stool, sputum, cerebrospinal fluid, or supernatant from cell lysate. In some embodiments, the biological sample includes a cell or tissue. In certain embodiments, the TARS molecule includes a TARS polypeptide. In some embodiments, the TARS molecule includes a TARS-encoding nucleic acid. In some embodiments, a means for the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In some embodiments, the method also includes selecting a treatment regimen for the subject based at least in part on the determined diagnosis. In certain embodiments, the treatment regimen includes administering one or more of a medicament, surgery, radiation, or chemotherapy to the subject. In some embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the diagnosis determined.

According to yet another aspect of the invention, methods of diagnosing a subject as having, or at increased risk of developing, a disorder associated with decreased threonyl-tRNA synthetase (TARS) activity are provided. The methods include (a) obtaining a biological sample from the subject; (b) measuring the amount of a TARS molecule in the biological sample; and (c) comparing the level of the TARS molecule in the biological sample to a disease control level of the TARS molecule, wherein a similar level of the TARS molecule in the subject biological sample compared to the disease control level is diagnostic for the subject having or being at increased risk of developing the disorder associated with decreased TARS activity. In certain embodiments, the disease control level is a level of the TARS molecule characteristic of biological samples from individuals having the disorder associated with decreased TARS activity. In some embodiments, the level of the TARS molecule is measured by measuring the level of a secreted TARS molecule. In some embodiments, the level of the TARS molecule is measured by measuring a non-secreted TARS molecule. In certain embodiments, the level of the TARS molecule is measured by measuring the activity of TARS. In some embodiments, the disorder associated with decreased TARS activity is an angiogenesis-associated disorder. In some embodiments, the angiogenesis-associated disease or condition is a tissue implant, organ implant, ischemia, cardiac infarction, tissue trauma, cartilage to bone transformation, stroke, peripheral vascular disease, surgery, pregnancy, macular degeneration, or vascular occlusion. In some embodiments, the biological sample is a sample of blood, tissue, serum, urine, stool, sputum, cerebrospinal fluid, or supernatant from cell lysate. In certain embodiments, the biological sample includes a cell or tissue. In some embodiments, the TARS molecule is a TARS protein. In some embodiments, the TARS molecule is a TARS-encoding nucleic acid. In some embodiments, a means for the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In certain embodiments, the method also includes selecting a treatment regimen for the subject based at least in part on the determined diagnosis. In some embodiments, the treatment regimen includes administering one or more of a medicament, surgery, radiation, or chemotherapy to the subject. In some embodiments, the treatment regimen includes stopping a prior administration regimen of one or more of a medicament, surgery, radiation, or chemotherapy to the subject. In certain embodiments, the control is a sample obtained from the subject at a different time than the sample obtained in step (a). In some embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the diagnosis determined.

According to yet another aspect of the invention, methods for determining a prognosis in a subject diagnosed with a disorder associated with decreased threonyl-tRNA synthetase (TARS) activity are provided. The methods include (a) obtaining a biological sample from the subject; (b) measuring a TARS molecule level in the subject's biological sample; (c) comparing the TARS molecule level of the subject's sample with a control level of the TARS molecule; and (d) correlating levels of the TARS molecule lower than the control level with an indication of unfavorable prognosis and levels of the TARS molecule at or above the control level with a favorable prognosis. In some embodiments, the disorder associated with decreased TARS activity is an angiogenesis-associated disorder. In certain embodiments, the angiogenesis-associated disease or condition is a tissue implant, organ implant, ischemia, cardiac infarction, tissue trauma, cartilage to bone transformation, stroke, peripheral vascular disease, diabetes, surgery, pregnancy, macular degeneration, vascular occlusion. In some embodiments, the TARS molecule is a TARS protein. In some embodiments, the TARS molecule is a TARS-encoding nucleic acid. In some embodiments, a means for the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In certain embodiments, the method also includes selecting a treatment regimen for the subject based at least in part on the determined prognosis. In some embodiments, the treatment regimen includes administering one or more of a medicament, surgery, radiation, or chemotherapy to the subject. In some embodiments, the treatment regimen includes stopping a prior administration regimen of one or more of a medicament, surgery, radiation, or chemotherapy to the subject. In some embodiments, the control is a sample obtained from the subject at a different time than the sample obtained in step (a). In certain embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the prognosis determined.

According to another aspect of the invention, methods of determining the onset, progression, or regression in a subject of a disorder associated with decreased threonyl-tRNA synthetase (TARS) activity are provided. The methods include (a) measuring the level of a TARS molecule in a first biological sample obtained from a subject, (b) measuring the amount of the TARS molecule in a second biological sample obtained from the subject, wherein the second biological sample is obtained from the subject at a time subsequent to the time the first biological sample is obtained; and (c) comparing the measurement of the TARS molecule in the first sample to the measurement of the TARS molecule in the second sample as a determination of the onset, progression, or regression of the disorder associated with decreased TARS activity. In some embodiments, a decrease in the level of the TARS molecule in the second sample compared to the first sample indicates the onset or progression of the disorder. In some embodiments, an increase in the level of the TARS molecule in the second sample compared to the first sample indicates the regression of the disorder. In some embodiments, the disorder associated with decreased TARS activity is an angiogenesis-associated disorder. In certain embodiments, the angiogenesis-associated disease or condition is a tissue implant, organ implant, ischemia, cardiac infarction, tissue trauma, cartilage to bone transformation, stroke, surgery, peripheral vascular disease, diabetes, pregnancy, macular degeneration, or vascular occlusion. In some embodiments, the TARS molecule is a TARS protein. In some embodiments, the TARS molecule is a TARS-encoding nucleic acid. In some embodiments, a means for the measuring includes an immunological assay, nucleotide determination (mRNA or DNA), mass spectrometry, TARS aminoacylation assay, TARS active site determination assay, a TARS binding assay including a TARS-binding reporter molecule, or an ELISA assay. In certain embodiments, the method also includes selecting a treatment regimen for the subject based at least in part on the determination of the onset, progression or regression of the disorder. In some embodiments, the treatment regimen includes administering one or more of a medicament, surgery, radiation, or chemotherapy to the subject. In some embodiments, the treatment regimen includes stopping a prior administration of one or more of a medicament, surgery, radiation, or chemotherapy. In certain embodiments, the method also includes administering one or more of a medicament, surgery, radiation, or chemotherapy to the subject to treat the disorder, wherein the selection of the one of more of the medicament, surgery, radiation, or chemotherapy is selected based, at least in part, on the determined onset, progression or regression of the of the disorder.

According to another aspect of the invention, kits are provided. The kits including a means for measuring activity of a threonyl-tRNA synthase (TARS) molecule and instructions for measuring a level of TARS activity in a biological sample obtained from a subject. In some embodiments, the kit also includes 1, 2, 3, 4, 5, 6, 7, 8, 9, 10, or more compounds that bind to or react with a TARS molecule, and a means for detecting the binding or reaction. In some embodiments, the kit also includes one or more detectable labels and instructions for using the one or more detectable labels to measure TARS activity in a biological sample. In some embodiments, the TARS molecule is a TARS protein. In certain embodiments, the TARS molecule is a TARS-encoding nucleic acid.

BRIEF DESCRIPTION OF THE DRAWINGS

FIG. 1B shows results from 10 nM BC194, and FIG. 1C shows results from 1000 nM BC194. Scale bar=100 µm. Graph in FIG. 1D shows quantification of branches over a range of BC194 concentrations using the Simple Neurite Tracer plug-in on ImageJ software. Numbers represent average data from 3 separate experiments performed in duplicate. Multiple comparisons of one-way ANOVA were performed using the Tukey Test; n=3, *p<0.05.

FIG. 3A-D shows Western blots and graphs that indicate that high concentrations of BC194 are required to stimulate the unfolded protein response and apoptosis. HUVECs grown in full serum media were exposed to the indicated concentrations of BC194, followed by Western Blot of cell extracts using antibodies recognizing phospho-eIF2α (FIG. 3A), cleaved caspase-3 (FIG. 3B) and β-actin or β-tubulin as a loading control. Quantification of phospho-eIF2α and c-caspase-3 relative to the loading controls were determined using Quantity One software and average data are shown in FIGS. 3C and 3D; respectively *p<0.05, n=3.

FIG. 4A is a graph showing effects of BC194 on cell viability. HUVECs were exposed to the indicated concentrations of BC194, and live cells were quantified by trypan blue exclusion and normalized to the untreated control; n=3, *p<0.05. FIG. 4B is a graph showing effects of BC194 on proliferation. HUVECs were exposed to the indicated concentrations of BC194 and proliferation was quantified over time using an Alamar Blue™ assay (a measure of NADPH oxidase activity). n=3, *p<0.05. FIG. 4C is a flow cytometry analysis, and FIG. 4D is an SDS-PAGE showing lack of effects of BC194 on nascent protein synthesis. Cells were exposed to the indicated concentrations of BC194 and new protein synthesis was detected using a Click-iT® metabolic labeling kit. Proteins were separated by SDS-PAGE and visualized using streptavidin-HRP. Cycloheximide (CHX, 50 µM) was used as a control for complete inhibition of protein synthesis.

FIG. 5A shows results using Coomassie stain of TARS and L567V TARS proteins separated by SDS-PAGE indicating purified intact proteins. FIG. 5B is a graph showing that purified TARS exhibits aminoacyl synthetase activity and activity is not compromised in the borrelidin-resistant mutant L567V. TARS activity was comparable to E. coli TARS and commercially available human TARS expressed in CHO cells (Francklyn, First et al. 2008).

FIGS. 6A, 6B, and 6C show results using low serum, full serum, and low serum+TARS, respectively. HUVECs were plated onto Matrigel in low serum (LS, 0.2% fetal bovine serum) or EGM-2 full serum media (FS, 5% FBS). Where indicated, 100 nM purified recombinant human TARS was added to the media. Tubes were imaged and analyzed after 6 h as in FIG. 1, Scale bar=100 µm. FIG. 6D is a histograph of quantified branches; n=3, $*p<0.01$ compared to low serum. FIG. 6E is a histogram of quantified branches for TARS effect; mean±standard error of the mean, n=3, *P, 0.01 compared to Low Serum (Student's test). FIG. 6F is a histogram of quantified branches for a range of BC194 concentrations added to Full Serum media. Numbers represent mean±standard error of the mean, n=3, $*P<0.05$ (one-way ANOVA, Tukey test).

FIG. 7A-C provides graphs and a photomicrographic image demonstrating that TARS induces in vivo angiogenesis in a CAM assay. Fertilized chicken embryos were cultured ex-ova and, starting at developmental day 10, agents were applied daily to gelfoam sponges on the CAM. Images were recorded daily over 72 h and scored blindly according to a modified version of Intensity Scoring as previously described (Ribatti et al, 2006). Graphs represent the change in CAM vascularity score over 72 h. (FIG. 7A) BC194 (10 nM) was applied to the CAM along with PBS (Control), bFGF (40 µg/ml), and VEGF (2 µg/ml). The angiostatic control retinoic acid (RA) was used at 100 µg/ml. Representative images for (FIG. 7A) are shown in FIG. 8B, and FIG. 8C. Purified recombinant TARS, BC194-resistant mutant TARS (L567V) and BC194 were applied at 100 µg/ml. FIG. 7C shows representative CAM images over time; arrows denote spoke-wheel response. Scale bar=1.0 mm. FIG. 7B is a histogram of change in CAM vascularity score over 72 h; n>14, $*p<0.001$ compared to PBS control; # $p<0.001$ compared to TARS.

FIG. 8A-N provides representative photomicrographic images for the graphs shown in FIGS. 7A and 7B. Fertilized chicken embryos were cultured ex-ova and, starting at developmental day 10, agents were applied daily to gelfoam sponges on the CAM. Left panels represent images taken at 24 h and right panels at 72 h for PBS Control (FIGS. 8A and 8B), bFGF (FIGS. 8C-F), VEGF (FIGS. 8G-J) and L567V TARS (FIGS. 8K-N). BC194 (100 ng/sponge) was included where indicated. Arrows indicate spoke-wheel response; Scale bar=1.0 mm. FIG. 9A shows Coomassie stain of 2 µg LARS separated by SDS-PAGE. FIG. 9B shows a graph indicating that LARS exhibits enzyme activity as measured by conversion of $^{32}P$-ATP to AMP. Numbers represent labeled AMP determined by thin layer chromatography followed by phosphorimaging. FIGS. 9C and D indicate that LARS has no effect on angiogenesis measured in the CAM assay. Purified LARS (100 ng/sponge) was added to CAMs as in FIG. 8. FIG. 9C provides representative images showing no effect of LARS on CAM vascularity; Scale bar=1.0 mm. FIG. 9D provides a graph representing the average CAM vascularity score over 72 h as compared to PBS or TARS; n=5, $*p<0.05$.

In FIG. 10A HUVECs were treated with VEGF or TNF-α (50 ng/ml) where indicated. After 6 h the level of TARS in the supernatant was determined by ELISA. Graph represents an average of 3 experiments; $*p<0.05$. FIG. 10B shows cell membrane integrity for the experiments in (A and C) using the lactate dehydrogenase assay CytoTox-ONE™ at 6 h and 16 h. Numbers represent percent cytotoxicity relative to a lysis control. For FIG. 10C HUVECs grown on a 10 cm dish were exposed to 50 ng/ml of VEGF or TNF-α in 0% serum EGM-2 media for 16 h. Shown is a representative TARS Western blot of cell lysates and media samples, n=4. Media was concentrated 20-fold to accommodate 25% onto the gel and compared to 5% of the cell lysate. Purified TARS was used to estimate the TARS concentration within samples. β-tubulin was measured as a loading and lysis control. FIG. 10D shows that VEGF and TNF-α do not induce TARS transcription. HUVECs were exposed to 50 ng/ml of VEGF or TNF-α followed by RNA extraction and RT-qPCR to measure TARS mRNA levels. Shown are Rq values relative to a β-2 macroglobulin control; n=3.

FIG. 11A shows results indicating that TARS does not significantly affect cell proliferation. HUVECs were cultured in low serum (0.2% FBS) media containing 50 ng/ml VEGF and 10 nM BC194 where indicated; relative proliferation was measured over time using an Alamar Blue™ assay; n=3. FIGS. 11B and C show VEGF and TARS-mediated migration. HUVEC migration was measured using a trans-well assay. The migration compartment contained 50 ng/ml VEGF, 100 nM LARS or 100 nM TARS and 10 nM BC194 where indicated. Shown in FIG. 11B are representative images of DAPI stained nuclei from migrated cells after 4 h. FIG. 11C shows a histogram representing number of migrated cells after 4 h for the conditions indicated; n>3, $*p<0.05$ compared to Control, # $p<0.05$ compared to VEGF.

FIG. 13A-C provides photomicrographs and a histogram of statistical analysis correlating TARS levels in prostate cancer tissue sections with Gleason score, and a table depicting the results of initial ELISA measurements on serum samples from prostate cancer patients. The images in FIG. 13A show results of immunohistochemistry of TARS within patient tissue sections showing examples of the scoring rubric. (i=TARS+1, ii=TARS+2, iii=TARS+3, iv=Atrophy, v=benign prostate hyperplasia (BPH) TARS+1, vi=BPH TARS negative, and vii=TARS negative). FIG. 13B presents a graph representing statistical analysis of TARS expression score as related to tumor diagnosis. Slides were scored by at least two pathologists, with a third tie breaker when necessary. Values within bars represent number of patients. *p<0.0001. FIG. 13C presents a table describing TARS serum measurements in four age matched control subjects and ten prostate cancer patients in various stages of diagnosis and treatment.

FIG. 16 lists the putative interacting partners of TARS, as determined from an affinity purification-mass spectrometry experiment. In all experiments, TARS was over-expressed (with a biotinylatable tag tail) and then affinity purified on streptavidin-conjugated beads. The bound proteins were then removed from the beads by boiling, resolved on SDS polyacrylamide gels, and then extracted from individual gel slices. The experiment was performed under two conditions. In Condition 1, only TARS was overexpressed; in Condition 2, both TARS and VHL were overexpressed.

FIG. 17A is a graph comparing the aminoacylation progress curves of wild and R442A mutant TARS. Based on the results of this assay, R442A TARS has virtually negligible aminoacylation function. FIG. 17B compares the change in CAM vascularity score for wild type, BC-194 resistant L567V TARS and aminoacylation-deficient R442A TARS. The histograms represent the change in vascularity score over 72 hour; *p<0.001 compared to PBS control; # P<0.001 compared to TARS. FIG. 17C is a graph comparing the progress curves of Ap4A formation for human TARS, R442A TARS, and TARS in the presence of BC194 or borrelidin. FIG. 17D is a graph comparing the progress curves of Ap4A formation for human TARS, R442A TARS, and TARS in the presence of (10 μM) BC194 or borrelidin (10 μM). FIGS. 17C and 17D indicate that Ap4A and Ap4G synthesis is blocked in R442A TARS, and its synthesis is at least partially inhibited by borrelidin and BC914. FIG. 17E is a graph comparing the progress curves of GTP hydrolysis for human TARS, R442A TARS, and E. coli ThrRS in the presence of (10 mM) BC194 or borrelidin. This plot indicates that wild type human and R442 TARS both possess potent GTPase activities, but the bacterial enzyme does not. FIG. 17F is a graph comparing the progress curves of GTP hydrolysis for human TARS in the presence of substrates that are specific for the aminoacylation reaction. The key result is that when ATP and aminoacylation substrates are present, GTPase function is severely inhibited.

Figure 1A:
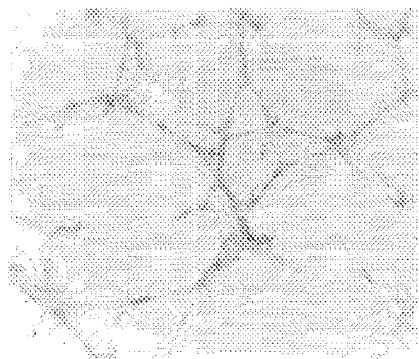
FIG. 1A-D provides photomicrographic images and a graph providing evidence that a subnanomolar concentration of the TARS inhibitor BC194 inhibits endothelial tube formation. Human umbilical vein endothelial cells (HUVECs) were seeded on Matrigel™ in full serum media (2% FBS) along with the indicated concentrations of BC194. After 6 h, cells were fixed and stained with Oregon Green 488 Phalloidin. Shown are representative images using the full serum media response as Control (FIG. 1A)
Figure 1B:
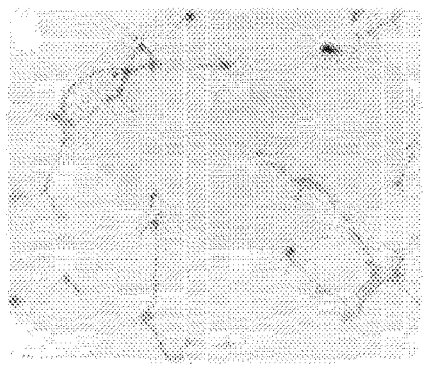
Figure 1C:
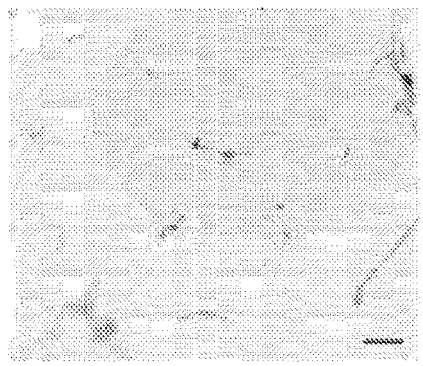
Figure 1D:
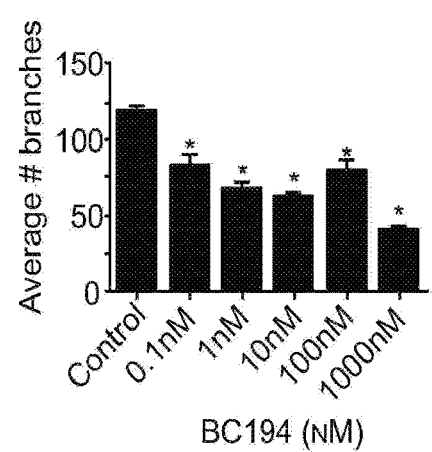

| Amino Acid and Nucleotide Sequences |
| --- |
| SEQ ID NO: 1 Human TARS nucleic acid sequence is provided as GENBANK ™ Accession No. NM_152295 mRNA. |
| ggtcagcggagagtaggcatgtagcttctgcagttgctcctcctcaccct |
| ccgcgacctgatttcctagaagggctctgtcacccgaaaagattttccac |
| tggcttagaggagggagggcccgccttccccgttatccattggctgctc |
| gttccgccgcaagttggggcggggttagggcgcctttcgattgcatcag |
| ctggtccagccgaggccaagtcccgggcgctagcccacctcccacccgcc |
| tcttggctcctctcctctaggccgtcgctttcgggttctctcatcgcttc |
| gtcgttcgccaatgtttgaggagaaggccagcagtccttcagggaagatg |
| ggaggcgaggagaagccgattggtgctggtgaagagaagcaaaaggaagg |
| aggcaaaaagaagaacaaagaaggatctggagatggaggtcgagctgagt |
| tgaatccttggcctgaatatattttacacacgtcttgagatgtataatata |
| ctaaaagcagaacatgattccattctggcagaaaaggcagaaaaagatag |
| caagccaattaaagtcactttgcctgatggtaaacaggttgatgcggaat |
| cttggaaaactacaccatatcaaattgcctgtggaattagtcaaggcctg |
| gccgacaacaccgttattgctaaagtaaataatgttgtgtgggacctgga |
| ccgccctctggaagaagattgtaccttggagcttctcaagtttgaggatg |
| aggaagctcaggcagtgtattggcactctagtgctcacataatgggtgaa |
| gccatggaaagagtctatggtggatgtttatgctacggtccgccaataga |
| aaatggattctattatgacatgtacctcgaagaaggggtgtgtctagca |
| atgatttctcttctctggaggcttttgtgtaagaaaatcattaaagaaaaa |
| caagcttttgaaagactggaagttaagaaagaaactttactggcaatgtt |
| taagtacaacaagttcaaatgccggatattgaatgaaaaggtgaatactc |
| caactaccacagtctatagatgtggccctttgatagatctctgccggggt |
| cctcatgttagacacacgggcaaaattaaggctttaaaaatacacaaaaa |
| ttcctccacgtactgggaaggcaaagcagatatggagactctccagagaa |
| tttatggcatttcattcccagatcctaaaatgttgaaagagtgggagaag |
| ttccaagaggaagctaaaaaccgagatcataggaaaattggcagggacca |
| agaactatatttctttcatgaactcagccctggaagttgcattactgcca |
| aaaggagcctacatttataatgcacttattgaattcattaggagcgaata |
| taggaaaagaggattccaggaggtagtcaccccaaacatcttcaacagcc |
| gactctggatgacctcgggccactggcagcactacagcgagaacatgttc |
| tcctttgaggtggagaaggagctgtttgccctgaaacccatgaactgccc |
| aggacactgccttatgtttgatcatcggccaaggtcctggcgagaactgc |
| ctctgcggctagctgattttggggtacttcataggaacgagctgtctgga |
| gcactcacaggactcacccgggtacgaagattccaacaggatgatgctca |
| catattctgtgccatggagcagattgaagatgaaataaaaggttgtttgg |
| attttctacgtacggtatatagcgtatttggattttcttttaaactaaac |
| ctttctactcgcccggaaaaattccttggagatatcgaagtatgggatca |
| agctgagaaacaacttgaaaacagtctgaatgaatttggtgaaaagtggg |
| agttaaactctggagatggagctttctatggcccaaagattgacatacag |
| attaaagatgcgattgggcggtaccaccagtgtgcaaccatccagctgga |
| tttccagttgcccatcagatttaatcttacttatgtaagccatgatggtg |
| atgataagaaaaggccagtgattgttcatcgagccatcttgggatcagtg |
| gaaagaatgattgctatcctcacagaaaactatgggggcaaatggccctt |

Amino Acid and Nucleotide Sequences ttggctgtccctcgccaggtaatggtagttccagtgggaccaacctgtg
atgaatatgcccaaaaggtacgacaacaattccacgatgccaaattcatg
gcagacattgatctggatccaggctgtacattgaataaaaagattcgaaa
tgcacagttagcacagtataacttcattttagttgttggtgaaaaagaga
aaatcagtggcactgttaatatccgcacaagagacaataaggtccacggg
gaacgcaccatttctgaaactatcgagcggctacagcagctcaaagagtt
ccgcagcaaacaggcagaagaagaattttaatgaaaaaattacccagatt
ggctccatggaaaaggaggaacagcgtaccgtaaaattgactttgtactc
tgaaaacgtcaatttatattgaacttggaggagtttggcaaagtctgaat
aggtcaacctgcaggcgtaactattatgacctagtcagatttaaacaatg
tgcatttgaaggagttaattaaaagagagccaataaaatgattttactca
ttcagtatctgagtactggaagtgaaacatgaggaatgctttagtgtaat
gtgggagaactttttttgtaaatttaatgcaattgaaaaagttttcaaatt
caattaagataactagaattggattatggtgtaaaaataaaaaaaaaatt
tattcacataaaaaaaaaaaaaaaaaaaaaaaa.

SEQ ID NO: 2 A human TARS protein sequence is
provided as GENBANK ™ Accession No. P26639, which
is also the amino acid sequence encoded by SEQ ID
NO: 1, which is set forth under GENBANK ™
Accession No. NM_152295
MFEEKASSPSGKMGGEEKPIGAGEEKQKEGGKKKNKEGSGDGGRAELNPW
PEYIYTRLEMYNILKAEHDSILAEKAEKDSKPIKVTLPDGKQVDAESWKT
TPYQIACGISQGLADNTVIAKVNNVVWDLDRPLEEDCTLELLKFEDEEAQ
AVYWHSSAHIMGEAMERVYGGCLCYGPPIENGFYYDMYLEEGGVSSNDFS
SLEALCKKIIKEKQAFERLEVKKETLLAMFKYNKFKCRILNEKVNTPTTT
VYRCGPLIDLCRGPHVRHTGKIKALKIHKNSSTYWEGKADMETLQRIYGI
SFPDPKMLKEWEKFQEEAKNRDHRKIGRDQELYFFHELSPGSCFFLPKGA
YIYNALIEFIRSEYRKRGFQEVVTPNIFNSRLWMTSGHWQHYSENMFSFE
VEKELFALKPMNCPGHCLMFDHRPRSWRELPLRLADFGVLHRNELSGALT
GLTRVRRFQQDDAHIFCAMEQIEDEIKGCLDFLRTVYSVFGFSFKLNLST
RPEKFLGDIEVWDQAEKQLENSLNEFGEKWELNSGDGAFYGPKIDIQIKD
AIGRYHQCATIQLDFQLPIRFNLTYVSHDGDDKKRPVIVHRAILGSVERM
IAILTENYGGKWPFWLSPRQVMVVPVGPTCDEYAQKVRQQFHDAKFMADI
DLDPGCTLNKKIRNAQLAQYNFILVVGEKEKISGTVNIRTRDNKVHGERT
ISETIERLQQLKEFRSKQAEEEF.

SEQ ID NO: 3 Mus musculus TARS polypeptide
sequence having GENBANK ™ Accession No. Q9D0R2.
MSQEKASSPSGKMDGEKPVDASEEKRKEGGKKKSKDGGGDGGRAELNPWP
EYINTRLDMYNKLKAEHDSILAEKAAKDSKPIKVTLPDGKQVDAESWKTT
PYQIACGISQGLADNTVVAKVNKVVWDLDRPLETDCTLELLKFEDEEAQA
VYWHSSAHIMGEAMERVYGGCLCYGPPIENGFYYDMYLEEGGVSSNDFSS
LETLCKKIIKEKQTFERLEVKKETLLEMFKYNKFKCRILNEKVNTPTTTV
YRCGPLIDLCRGPHVRHTGKIKTLKIHKNSSTYWEGKADMETLQRIYGIS
FPDPKLLKEWEKFQEEAKNRDHRKIGRDQELYFFHELSPGSCFFLPKGAY
IYNTLMEFIRSEYRKRGFQEVVTPNIFNSRLWMTSGHWQHYSENMFSFEV
EKEQFALKPMNCPGHCLMFDHRPRSWRELPLRLADFGVLHRNELSGALTG
LTRVRRFQQDDAHIFCAMEQIEDEIKGCLDFLRTVYSVFGFSFKLNLSTR
PEKFLGDIEIWNQAEKQLENSLNEFGEKWELNPGDGAFYGPKIDIQIKDA
IGRYHQCATIQLDFQLPIRFNLTYVSHDGDDKKRPVIVHRAILGSVERMI
AILTENYGGKWPFWLSPRQVMVVPVGPTCDEYAQKVRQQFHDAKFMADTD
LDPGCTLNKKIRNAQLAQYNFILVVGEKEKASGTVNIRTRDNKVHGERTV
EETVRRLQQLKQTRSKQAEEEF.

SEQ ID NO: 4 C Elegans TARS polypeptide sequence
having GENBANK ™ Accession No. P52709.
MRLNCFRIFVHIQKPTQIFKPFYRSLSSEASDKYHFVNGHKMSKAPTDMA
PWPAFIEERIKLWDKLKAEYDAEIAAKESEPIQITLPDGKIHEGKTWRTT
PFEIAERISKGLAEAAVIAKVNGAVWDLDRPFEGNAKLELLKFDDDEAKQ
VFWHSSAHVLGEAMERYCGGHLCYGPPIQEGFYYDMWHENRTICPDDFPK
IDQIVKAAVKDKQKFERLEMTKEDLLEMFKYNEFKVRIITEKIHTPKTTV
YRCGPLIDLCRGPHVRHTGKVKAMAITKNSSSYWEGKADAESLQRLYGIS
FPDSKQLKEWQKLQEEAAKRDHRKLGKEHDLFFFHQLSPGSAFWYPKGAH
IYNKLVDFIRKQYRRRGFTEVITPNMYNKKLWETSGHWQHYSEDMFKIEV
EKEEFGLKPMNCPGHCLMFGHMPHTYNELPFRFADFGVLHRNEMSGALTG
LTRVRRFQQDDAHIFCRQDQISEEIKQCLDFLEYAYEKVFGFTFKLNLST
RPEGFLGNIETWDKAEADLTNALNASGRKWVLNPGDGAFYGPKIDITIQD
ALKRNFQCATIQLDFQLPNQFDLSYFDEKGEKQRPVMIHRAVLGSVERMT
AILTESYGGKWPFWLSPRQCKIITVHESVRDYANDVKKQIFEAGFEIEYE
ENCGDTMNKQVRKAQLAQFNFILVIGAKEKENGTVNVRTRDNAVRGEVAL
DKLISKFRRFADEYVADTEKSEEWA.

SEQ ID NO: 5 S cerevisiae TARS polypeptide
sequence having GENBANK ™ Accession No. P04801.
MSASEAGVTEQVKKLSVKDSSNDAVKPNKKENKKSKQQSLYLDPEPTFIE
ERIEMFDRLQKEYNDKVASMPRVPLKIVLKDGAVKEATSWETTPMDIAKG
ISKSLADRLCISKVNGQLWDLDRPFEGEANEEIKLELLDFESDEGKKVFW
HSSAHVLGESCECHLGAHICLGPPTDDGFFYEMAVRDSMKDISESPERTV
SQADFPGLEGVAKNVIKQKQKFERLVMSKEDLLKMFHYSKYKTYLVQTKV
PDGGATTVYRCGKLIDLCVGPHIPHTGRIKAFKLLKNSSCYFLGDATNDS
LQRVYGISFPDKKLMDAHLKFLAEASMRDHRKIGKEQELFLFNEMSPGSC
FWLPHGTRIYNTLVDLLRTEYRKRGYEEVITPNMYNSKLWETSGHWANYK
ENMFTFEVEKETFGLKPMNCPGHCLMFKSRERSYRELPWRVADFGVIHRN
EFSGALSGLTRVRRFQQDDAHIFCTHDQIESEIENIFNFLQYIYGVFGFE
FKMELSTRPEKYVGKIETWDAAESKLESALKKWGGNWEINAGDGAFYGPK
IDIMISDALRRWHQCATIQLDFQLPNRFELEFKSKDQDSESYERPVMIHR
AILGSVERMTAILTEHFAGKWPFWLSPRQVLVVPVGVKYQGYAEDVRNKL
HDAGFYADVDLTGNTLQKKVRNGQMLKYNFIFIVGEQEMNEKSVNIRNRD
VMEQQGKNATVSVEEVLKQLRNLKDEKRGDNVLA.

SEQ ID NO: 6 Homo sapiens TARS cytoplasmic isoform
1 having GENBANK ™ Accession No NP_689508.
MFEEKASSPSGKMGGEEKPIGAGEEKQKEGGKKKNKEGSGDGGRAELNPW
PEYIYTRLEMYNILKAEHDSILAEKAEKDSKPIKVTLPDGKQVDAESWKT
TPYQIACGISQGLADNTVIAKVNNVVWDLDRPLEEDCTLELLKFEDEEAQ
AVYWHSSAHIMGEAMERVYGGCLCYGPPIENGFYYDMYLEEGGVSSNDFS
SLEALCKKIIKEKQAFERLEVKKETLLAMFKYNKFKCRILNEKVNTPTTT
VYRCGPLIDLCRGPHVRHTGKIKALKIHKNSSTYWEGKADMETLQRIYGI
SFPDPKMLKEWEKFQEEAKNRDHRKIGRDQELYFFHELSPGSCFFLPKGA
YIYNALIEFIRSEYRKRGFQEVVTPNIFNSRLWMTSGHWQHYSENMFSFE
VEKELFALKPMNCPGHCLMFDHRPRSWRELPLRLADFGVLHRNELSGALT
GLTRVRRFQQDDAHIFCAMEQIEDEIKGCLDFLRTVYSVFGFSFKLNLST
RPEKFLGDIEVWDQAEKQLENSLNEFGEKWELNSGDGAFYGPKIDIQIKD
AIGRYHQCATIQLDFQLPIRFNLTYVSHDGDDKKRPVIVHRAILGSVERM
IAILTENYGGKWPFWLSPRQVMVVPVGPTCDEYAQKVRQQFHDAKFMADI
DLDPGCTLNKKIRNAQLAQYNFILVVGEKEKISGTVNIRTRDNKVHGERT
ISETIERLQQLKEFRSKQAEEEF.

SEQ ID NO: 7 is a portion of the sequence set
forth in GENBANK ™ Accession No.: NM_152295.
RAELNPWPEYIYTRLEMYNILKAEHDSILAEKAEKDSKPIKVTLPDGKQV
DAESWKTTPYQIACGISQGLADNTVIAKVNNVVWDLDRPLEEDCTLELL
K.

SEQ ID NO: 8 is forward primer
5' caccagtgtgcaaccatccagctggatttccaggtgcccatcagatt
taatc 3'.

SEQ ID NO: 9 is reverse primer
5' gattaaatctgatgggccactggaaatccagctggatggttgcacac
tggtg 3'.

DETAILED DESCRIPTION

Angiogenesis is involved in many cellular functions and processes including in diseases and conditions such as cancer, tumors, hemangiomas, vascular overgrowth, venous malformation, arterial malformation, overweight (fat storage), macular degeneration, inflammatory disease, psoriasis, diabetes, and rheumatoid arthritis that may be characterized by excess angiogenesis and/or for which it may be desirable to limit or reduce angiogenesis for treatment. Angiogenesis is also involved in diseases and conditions such as tissue or organ implants, ischemia, cardiac infarction, tissue trauma, cartilage to bone transformation, stroke, surgery, pregnancy, macular degeneration, vascular occlusion, which may be characterized by the presence of insufficient angiogenesis and/or for which it may be desirable to increase angiogenesis as a treatment. It has now been identified that threonyl-tRNA synthetase (TARS) plays a role in angiogenesis and can be used in methods to diagnose and treat diseases and conditions characterized by abnormal (either increased or decreased) levels of TARS. As used herein, with respect to TARS activity, the terms: "increased", "elevated", and "higher" are used interchangeably. As used herein with respect to TARS molecule activity and quantitation, the terms "decrease", "reduced", and "lower" are used interchangeably.

In cancers, angiogenesis signaling can be an early step in invasive cancer growth, ascites formation, and metastasis. Cells that are environmentally stressed by hypoxia and/or starvation respond by expressing genes that support anaerobic metabolism and stimulate angiogenesis. Because of their rapid growth, many cancer cell types continuously express these genes in an effort to continue growing in a nutrient-poor environment. The development of vasculature, e.g., angiogenesis, involves changes in protein synthesis and may be initiated by environmental stress such as hypoxia or starvation in a cell. Aminoacyl tRNA synthetases are believed to function in some aspects of angiogenesis. Cancer treatments that reduce angiogenesis have recently been shown to causes hypoxia, enhancing the ability of cancer stem cells to increase their invasiveness and metastatic potential. Hence, cancer diagnoses and treatments that influence the hypoxic response are significant and novel area of cancer therapeutics.

It has now been identified that the determination of the levels and activity of threonyl-tRNA synthetase (TARS) in cells and tissues can be used in methods to diagnose diseases and conditions in which angiogenesis is altered, e.g., is abnormal compared to cells and tissues lacking the disease or condition. Thus, it is now understood that levels of TARS expression and function can be useful in methods to diagnosis diseases and conditions that are characterized at least in part by altered TARS activity. Diseases and conditions that have altered TARS activity may include angiogenesis-associated diseases and conditions, examples of which are provided herein, and include but are not limited to cancer. Thus, the improved understanding the role of TARS in early angiogenesis signaling has now been used to identify novel diagnostic targets to recognize and diagnose angiogenesis-associated conditions, such as cancer, thus improving the likelihood of successful treatment.

Protein synthesis is known to include activities of aminoacyl tRNA synthetases, which are enzymes that catalyze the aminoacylation of tRNA by their cognate amino acids. Threonyl-tRNA synthetase (TARS) is an aminoacyl tRNA synthetase that is known to charge tRNA with threonine during protein synthesis. Protein synthesis plays a role in many different activities of cells and tissues such as growth and development, differentiation, replication, signaling, etc. and alterations in aminoacyl tRNA synthetase activities and functions may result in disruption of cell processes and disease. One non-limiting example of a disorder that TARS activity may play a role in is cancer.

Cancer cells respond to environmental stress and the tumor microenvironment plays a role in determining cancer cell survival and growth responses. Cancer cells rely on these responses because they rapidly outgrow their blood supply and must survive under conditions of hypoxia, starvation, and metabolic stress. Cells relieve these stresses by decreasing protein translation through the unfolded protein response and increasing blood supply through secretion of angiogenic cytokines and growth factors. A novel connection between these metabolic and angiogenic responses has now been identified and features, in part, the ability of tRNA synthetase inhibitors to alter the angiogenesis signaling pathway through a novel mechanism. In addition to having a role in cancer, angiogenesis also occurs physiologically during fetal development, wound healing, pregnancy, weight gain, and ischemic preconditioning, and is a feature found numerous additional diseases and conditions.

TARS is an aminoacyl-tRNA synthetase that selectively catalyzes the ATP-dependent formation of threonyl-tRNA, a substrate for the protein translation machinery. Aside from their canonical functions in protein synthesis, aminoacyl-tRNA synthetases have been implicated in autoimmune and cytokine function, recovery from hypoxic stress, and angiogenesis. (Brown, M. V. et al. (2010) *Vascul Pharmacol* 52 (1-2), 21-26). Secretion and cytokine activities of extracellular TARS have now been examined and it has now been identified that TARS is secreted under conditions of exposure to cytokines (e.g., TNF-αt and VEGF) and that one or more specific domains of TARS, including the N-terminal domain of TARS (the TGS domain), are regulatory in nature and able to confer cytokine activity.

Threonyl-tRNA synthetase (TARS) is a metabolic workhorse that functions to charge tRNA with threonine during protein synthesis. TARS is ubiquitously expressed in a number of prokaryotic and eukaryotic organisms. TARS is alternatively known as threonine tRNA ligase 1; Threonine—tRNA ligase, threonyl-transfer ribonucleate synthetase, threonyl-transfer RNA synthetase, threonyl-transfer ribonucleic acid synthetase, threonyl ribonucleic synthetase, threonine-transfer ribonucleate synthetase, threonine translase, TRS, and ThrRS. An example of a human TARS protein sequence is provided as GENBANK™ Accession No. P26639. Examples of TARS polypeptide sequences of other species include: *Mus musculus*: GENBANK™ Accession No.Q9D0R2; *C Elegans*: GENBANK™ Accession No. P52709; *S cerevisiae*: GENBANK™ Accession No. P04801. A human TARS nucleic acid sequence is provided as GENBANK™ Accession No. NM_152295.

It has now been discovered that TARS acts in a previously unknown manner to promote angiogenesis. Studies have now shown that inhibition of TARS reduces both the hypoxic response of cancer cells and, unexpectedly, that application of exogenous purified TARS also stimulated angiogenesis in an in vivo angiogenesis assay. Thus, TARS may have dual functions as a metabolic regulator and as an angiogenic cytokine, and may be secreted from cells exposed to ischemic stress. It has also now been found that TARS mRNA and TARS polypeptide may be selectively overexpressed in various cancers, including but not limited to ovarian tumors, which are highly angiogenic. An association between TARS polypeptide expression and activity levels are positively correlated with angiogenesis and with cancer metastases. It has also now also been identified that levels and/or activity of TARS mRNA and TARS polypeptide may be higher than normal or lower than normal in additional diseases and conditions as described herein.

It has now been shown that an increase in expression and/or activities of TARS (potentially including GTPase and Ap4A synthetic functions) is correlated with an increase in angiogenesis of cells and also that an increase in expression and/or activity of TARS is correlated with metastasis of a cancer compared to a lower level of expression and/or activity of TARS in a poorly metastatic or non-metastatic cancer. Thus, expression and/or activity of TARS can be used to determine angiogenic potential in cells and tissues and can also be used to determine metastatic potential in cancers. In addition, the protein provides a target for treatments to enhance or inhibit angiogenesis and for treatments to inhibit the metastatic process in cancers.

Accordingly, the evaluation and comparison of levels of TARS molecules, such as TARS-encoding nucleic acids and TARS polypeptides, either normal or mutated, can be both diagnostic and prognostic for particular diseases and conditions associated with angiogenesis. In some aspects of the invention, the disease or condition associated with angiogenesis is cancer and may be metastatic cancer. It has now been identified, that an elevated level of TARS, which may be a level of TARS polypeptide or level of TARS-encoding nucleic acid, for example, may indicate an increase in angiogenesis in a cell, a tissue, and/or a subject. In some aspects, an increase in the TARS polypeptide or TARS-encoding nucleic acid level may indicate an increased likelihood for metastatic activity of a cancer, while lower levels of TARS and/or TARS activity may indicate that the cancer has reduced metastatic potential. Further, by monitoring a particular neoplastic growth over a period of time and comparing changes in the level of a TARS polypeptide or TARS-encoding nucleic acid, one can evaluate changes in metastatic activity of the cancer.

The present invention provides methods of diagnosing a disease or condition associated with abnormal TARS activity. As used herein, the term "TARS activity" refers to a function of the TARS molecule, such as, but not limited to, aminoacylation of tRNA by threonine, association of a TARS polypeptide with a von Hippel Lindau (VHL) polypeptide to form a complex, association of a TARS polypeptide with elongation factor 1 (eEF1) to form a complex, associate of a TARS polypeptide with an E3 ubiquitin ligase, secretion of TARS protein or fragment of protein, binding of TARS to membrane receptors, or binding of TARS to extracellular matrix proteins.

In some embodiments of the invention, a disease or condition may be characterized by increased TARS activity compared with a control level of TARS activity. In certain embodiments of the invention a disorder or condition may be characterized by decreased TARS activity compared with a control level of TARS activity. It will be understood that a change in TARS activity may be due to a change in the amount of TARS expressed in a cell, tissue, or subject, a change in the function or activity of TARS that is expressed in a cell, tissue, or subject, and/or a change in the secretion of TARS by a cell, tissue, or subject. Thus, in some embodiments of the invention, a reduction in TARS activity may be a result of a reduction in the amount of TARS polypeptide in a cell, tissue, or fluid and in some embodiments the amount of TARS polypeptide may be unchanged (e.g., normal compared with a normal control) but the functional activity of the TARS that is present in the cell, tissue, or subject may be reduced. Similarly, in some embodiments of the invention, an increase in TARS activity may be a result of an increase in the amount of TARS polypeptide in a cell, tissue, fluid or subject and in certain embodiments the amount of TARS polypeptide may be unchanged (e.g., normal compared with a normal control) but the functional activity of the TARS that is present in a cell or tissue may be increased. The altered activity may the result of an increase in availability of a post-translationally modified version of TARS, which may be differentially secreted from one or more relevant cell types (including cancer cells, HUVEC cells, or cells of the innate immune system).

It has been identified that altered TARS activity in cells and/or tissues is correlated with various diseases and conditions. In certain diseases and conditions the level of TARS activity is statistically significantly higher in cells and/or tissues having the disease or condition compared to the level of TARS activity in cells and/or tissues that do not have the disease or condition. A level of TARS activity in a disease or condition characterized by a significantly higher activity compared to a normal control level may have a level of TARS activity that is at least 1%, 5%, 10%, 20%, 30%, 40%, 50%, 60%, 70%, 80%, 90%, 100%, 125%, 150%, 175%, 200%, or higher than a normal control level of TARS activity, e.g., a level in an equivalent sample that does not have a disorder or condition characterized by elevated, e.g., higher levels of TARS activity. As used herein, a disease or condition that may be characterized by elevated TARS activity may also be referred to as a disease or condition associated with elevated TARS activity.

Examples of diseases and conditions that may be characterized elevated TARS activity include, but are not limited to cancer, a tumor, a hemangioma, vascular overgrowth, venous malformation, arterial malformation, overweight, macular degeneration, inflammatory disease, psoriasis, diabetes, interstitial lung disease, and rheumatoid arthritis. An increase in angiogenesis may be a characteristic of diseases and conditions in which a higher TARS activity (versus a normal control level) is present. Non-limiting examples of cancers that may be characterized by elevated levels of TARS activity include a metastatic carcinoma of the cervix; sarcoma of the kidney; renal cell carcinoma; androgen independent prostate cancer; Kaposi's sarcoma; colorectal cancer, hepatobilliary cancer, gastric cancer, epithelial ovarian cancer; lung cancer, and mesothelioma. In some aspects of the invention, assessing a change in the level of TARS activity in a disease or condition characterized by increased TARS activity may be desirable, and methods of the invention may be used to monitor the level of TARS activity over time to assess changes.

In certain diseases and conditions a level of TARS activity is statistically significantly lower in cells and/or tissues having the disease or condition compared to the level of TARS activity in cells and/or tissues that do not have the disease or condition. A level of TARS activity in a disease or condition characterized by a significantly lower activity compared to a normal control level may have a level of TARS activity that is at less than 95%, 90%, 85%, 80%, 75%, 70%, 65%, 60%, 55%, 50%, 45%, 40%, 35%, 30%, 25%, 20%, 15%, 10%, 5%, or 1%, of a level in a normal control of TARS activity, e.g., a level in an equivalent sample that does not have a disorder or condition characterized by reduced, e.g., lower levels of TARS activity.

Examples of diseases and conditions that may be characterized by reduced TARS activity include, but are not limited to diseases or conditions such as is a tissue implant, organ implant, ischemia, cardiac infarction, tissue trauma, cartilage to bone transformation, stroke, surgery, pregnancy, macular degeneration, or vascular occlusion. In some aspects of the invention, assessing a change in the level of TARS activity in a disease or condition characterized by reduced (e.g., lower compared to a control) TARS activity may be desirable and methods of the invention may be used to monitor the level of TARS activity over time to assess changes. As used herein, a disease or condition that may be characterized by reduced TARS activity may also be referred to as a disease or condition associated with reduced TARS activity.

Diagnostic methods of the invention may include determining a level of TARS in a cell or tissue sample and comparing the determined level to a control level of TARS. For example a diagnostic test of the invention may include determining a level of TARS activity in a subject that has, is suspected of having, or is susceptible to having, or is at risk of having a disease or condition characterized by altered TARS activity. A TARS level can be determined using methods of the invention to measure the amount and/or activity of a TARS molecule in an in vitro assay of a biological sample that has been obtained from the subject. As used herein, the term "measure" may refer to a determination of the presence or absence of a TARS molecule, may refer to a determination of a quantity a TARS molecule, or may refer to a determination of an activity level of a TARS molecule. Methods of measuring polypeptides or nucleic acids are known in the art, and non-limiting examples of measuring means are provided herein.

Detection methods suitable for use in methods of the present invention can be used to detect TARS polypeptide or nucleic acid molecules in a biological sample in vitro as well as in vivo. For example, in vitro techniques for detection of TARS mRNA include reverse transcriptase quantitative polymerase chain reaction (RT-qPCR), Northern hybridizations, in situ hybridizations, DNA or oligonucleotide array, and next generation sequencing. In vitro techniques for detection of TARS DNA include polymerase chain reaction (PCR) and Southern hybridizations. In vitro techniques for detection of TARS polypeptide include, but are not limited to enzyme linked immunosorbent assays (ELISAs), Western blots, immunoprecipitations and immunofluorescence, and other known suitable techniques. Alternatively, TARS polypeptide can be detected in vivo in a subject by introducing into the subject a labeled anti-TARS antibody. For example, the antibody can be labeled with a detectable marker such as a colorimetric marker, enzymatic marker, radioactive marker, etc. whose presence and location in a subject can be detected by standard imaging techniques.

Certain embodiments of the invention include methods of performing an in vivo diagnostic test in a subject. An in vivo diagnostic test of the invention may include administering to a subject one or more compounds useful to determine a level of TARS in a cell or tissue in the subject. In a non-limiting example, a detectably labeled antibody or antibody fragment that binds a TARS polypeptide can be administered to the subject and can be measured to determine the TARS level in the subject, e.g., in a cell, or tissue in the subject. It will be understood that when using an in vivo method of the invention, the biological sample tested from the subject may comprise an in vivo cell or tissue sample and that the in vivo cell or tissue is considered to have been obtained from the subject even though the sample is not removed from the subject prior to use in the diagnostic method of the invention.

In some aspects of the invention, a disease for diagnosis may be one for which a biological sample can be obtained from a subject for testing and assay. In certain embodiments, a diagnosis is done in vivo and the diagnostic molecule (e.g., antibody, binding molecule or other compound) that is used to detect a TARS molecule must be administered to a subject. Where the present invention provides for the administration of, for example, antibodies or one or more other detectable compounds or small molecules to a subject, then this may be by any suitable route. The route of administration will depend, in part, on the location of the disease or condition for diagnosis. For example, if the disease to be diagnosed in vivo includes a tumor, an appropriate method of administration may be by injection directly to the site of the tumor. Thus, administration may by injection, including subcutaneous, intramuscular, intravenous, intrathecal, intracranial, and intradermal injections. Administration can also be by other means as described elsewhere herein. Administration via a catheter is also a mode of administration useful in some embodiments of the invention.

In Vivo Imaging Techniques

A molecule used in a diagnostic method of the invention, (e.g., an anti-TARS antibody or fragment thereof, a small molecules that bind to TARS or to TARS in associated with another polypeptide, etc.—(also referred to herein as "a diagnostic molecule of the invention") may also be used for imaging purposes, for example, to detect tumor metastasis. Suitable labels that may be attached to a diagnostic molecule and used in methods of the invention include, but are not limited to, radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin, and nano- or micro-particles.

In some embodiments a diagnostic molecule (e.g., an antibody or fragment thereof etc.) used for a diagnostic method of the invention may be labelled, or otherwise modified, to permit detection. Such labeled diagnostic molecules can be used for real-time in vivo diagnostics using sample that remains within (e.g., is not removed from) a subject or for in vitro diagnostics using a sample that is removed from a subject. Although not intending to be limited, an example of an in vitro diagnostic method of the invention may include use of a labeled anti-TARS antibody to detect tumor margins in tissue, for example, in a tissue removed during the process of surgery. Detectable labels that can be used in conjunction with a diagnostic molecule of the invention may be any that do not substantially interfere with the diagnostic molecule binding to a TARS molecule, but that allow external detection. Examples of detectable labels and methods suitable for use in in vitro diagnostic methods of the invention are described in detail elsewhere herein. Suitable in vivo detectable labels may include those that may be detected by X-radiography, NMR or MRI. For X-radiographic techniques, suitable detectable labels include any radioisotope that emits detectable radiation but that is not overtly harmful to the patient, such as barium or cesium, for example. Suitable detectable labels for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce in vivo diagnostic images. In the case of a radioisotope moiety, for a human subject, the quantity of radioactivity injected will normally range from about 5 to 20 millicuries of technetium-99m. The labeled diagnostic molecule (for example, labeled antibody or antibody fragment thereof or other TARS binding molecule) will then preferentially accumulate at the location of sample cells that contain TARS. The labeled diagnostic molecule can then be detected using known techniques.

In some embodiments of the invention, a diagnostic molecule for use in an in vitro or in vivo diagnostic method of the invention may be administered to a subject. For example, a diagnostic molecule may be administered to a subject and subsequently a biological sample may be obtained from that subject and examined in vitro using a diagnostic method set forth herein. In certain embodiments, a diagnostic molecule may be administered to a subject and subsequently an in vivo testing method used to determine a TARS activity level in a biological sample that remains within the subject. Thus, in some aspects of the invention, a diagnostic molecule may be administered orally, topically, or by parenteral means, including subcutaneous and intramuscular injection, implantation of sustained release depots, intravenous injection, intrathecal injection, intranasal administration, vaginal administration, rectal administration, and the like. Accordingly, a diagnostic molecule of the invention may be administered as a pharmaceutical composition comprising the treatment compound in combination with a pharmaceutically acceptable carrier. Such compositions may be aqueous solutions, emulsions, creams, ointments, suspensions, gels, liposomal suspensions, and the like. Suitable carriers (excipients) include, but are not limited to, water, saline, Ringer's solution, dextrose solution, and solutions of ethanol, glucose, sucrose, dextran, mannose, mannitol, sorbitol, polyethylene glycol (PEG), phosphate, acetate, gelatin, collagen, vegetable oils, and the like. One or more pharmaceutically acceptable salts may be included in a pharmaceutical composition of the invention. Exemplary pharmaceutically acceptable salts include, but are not limited to mineral acid salts such as hydrochlorides, hydrobromides, phosphates, sulfates, and the like; and the salts of organic acids such as acetates, propionates, malonates, benzoates, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin and the like. Other topical formulations include aerosols, bandages, and other wound dressings or wound-packing materials.

The amount of a diagnostic molecule required for a diagnostic method of the invention will of course vary depending upon the nature, location, and severity of the disorder, the age and condition of the subject, and other factors readily determined by one of ordinary skill in the art, including, but not limited to a health-care professional.

A method of the invention may include comparing a level of a TARS molecule in a sample to a control value or level for the TARS molecule. As used herein a "control" may be a normal control or a disease control. Selection and use of appropriate controls in diagnostic methods are well known in the art. In some embodiments of the invention, a normal control level may be obtained from a cell or tissue sample that is known to be free of the disease or condition associated with altered (increased or decreased) TARS activity. A normal control level of a TARS molecule and/or TARS molecule activity can readily be determined by measuring a level of the TARS molecule or TARS molecule activity using an assay provided herein and/or any suitable assay available in the art. In some embodiments of the invention, a disease control level may be obtained from a cell or tissue sample that includes cells and/or tissues known have the disease or condition associated with altered TARS activity. In some embodiments, a disease control TARS level may be based on levels obtained from one or more subjects known to have the disease or condition associated with altered TARS activity. In certain embodiments of the invention, the disease control may be a sample from a subject diagnosed with the disease or condition and the subject's disease control may be compared to another sample obtained from the subject at a different time. Disease control levels of TARS and TARS activity can readily be determined by measuring levels of TARS or TARS activity, respectively, in a biological sample of individuals having the disease or condition associated with altered (higher or lower) TARS activity.

In some aspects of the invention methods are provided that include comparing a level of TARS determined or measured a sample obtained from a subject to a control value for determining a disease stage or subject prognosis. In addition, onset, progression, or regression of a disease or condition characterized by altered TARS activity can be assessed by determining TARS levels in a subject by measuring TARS levels in samples obtained from or tested in the subject at two, three, four, five, or more different times. In a method that utilizes two or more samples obtained from a subject at different times, values obtained from a sample obtained at one time can be compared to values obtained at other times. For example, a first level obtained from the subject may serve as a baseline level or control level for that subject, thus allowing comparison of the TARS level and the determination of change or stability of the TARS level over time. TARS levels could also be measured after a specific course of treatment against cancer or other diseases has been initiated, with the intent of determining the efficacy of that treatment or the onset of relapse as a consequence of resistance to the treatment.

The status of the angiogenesis-associated disease or condition can be monitored using methods of determining TARS polypeptide activity or levels of nucleic acids that encode a TARS polypeptide, etc. In some aspects of the invention, a desired response to treatment of the angiogenesis-associated disease or condition also can be delaying the onset or even preventing the onset of the angiogenesis-associated disease or condition.

The invention, in some aspects, includes methods and assays (e.g. binding assays, gel electrophoresis; mass spectrometry; NMR; etc.) to determine changes in TARS level and/or activity in a subject or cell sample (e.g., cell culture) over time. This allows monitoring of TARS levels and/or activity in a subject who is to undergo treatment for a cancer or other proliferative disease or condition and also enables to monitoring in a subject who is currently undergoing therapy for the cancer or proliferative disease or condition. Thus, methods of the invention may be used to diagnose or assess a cancer or proliferative disease or condition in a subject and may also be used to assess the efficacy of a therapeutic treatment of a cancer or proliferative disease or condition and for assessment of the activity or level of a TARS molecule in a subject at various time points. For example, a subject's TARS level and/or activity can be determined prior to the start of a therapeutic regimen (either prophylactic or as a treatment of a cancer or other proliferative disease or condition), during the treatment regimen and/or after a treatment regimen, thus providing information on the status of the cancer or proliferative disease or condition in the subject.

Assessment of efficacy of candidate TARS-modulating compounds to increase or decrease expression of TARS polypeptide-encoding nucleic acid or a TARS polypeptide in a cell or tissue may also be done using assays of the invention in cells from culture—e.g., as screening assays to assess candidate TARS-modulating compounds to modulate TARS polypeptide activity. TARS-modulating compounds that alter TARS polypeptide activity in a cell, tissue, or subject may be used in the treatment of a cancer or proliferative disease or condition or as a pretreatment for a cancer or proliferative disease or condition (e.g., to prepare a cell or subject for subsequent treatment).

It will be understood that a therapeutic regimen may be either prophylactic or a treatment of a cancer or proliferative disease or condition in a subject. The invention in some aspects provides methods that may be used to monitor a subject's response to prophylactic therapy and/or treatment for a cancer or proliferative disease or condition provided to a subject. Methods of the invention (e.g. binding assays, gel electrophoresis; mass spectrometry; NMR; etc.) may also be useful to monitor the onset, progression, or regression of cancer or proliferative disease or condition in a subject at risk of developing the cancer or proliferative disease or condition. TARS polypeptide levels and/or activity or TARS-encoding nucleic acid levels may be determined in two, three, four, or more biological samples obtained from a subject at separate times. The TARS polypeptide levels and/or activity or the TARS-encoding nucleic acid levels determined in the samples may be compared and changes in the levels and/or activity over time may be used to assess the status and stage of a cancer or proliferative disease or condition in the subject (or in a cell or tissue sample) and/or the effect of a treatment strategy on the cancer or proliferative disease or condition in a subject (or a cell or tissue sample). Some embodiments of methods of the invention can be used to assess treatments for cancer or proliferative disease or conditions and can be used to obtain useful prognostic information by providing an indicator of a status of a cancer or proliferative disease or condition and in some embodiments of the invention, can be used to select a therapy for the subject, for example, to select a drug therapy, behavioral therapy, surgical therapy, etc.

Assays for assessing TARS levels in embodiments of the invention may include determining one or more TARS levels and/or activities, including but not limited to determining levels of nucleic acids that encode TARS polypeptides and/determining levels of TARS polypeptides in cells, tissues, and subjects. Levels of TARS polypeptide-encoding nucleic acids and TARS polypeptides can be determined in a number of ways when carrying out the various methods of the invention. In some embodiments of the invention, a level of a TARS polypeptide-encoding nucleic acid or TARS polypeptide is measured in relation to a control level of TARS polypeptide-encoding nucleic acid or TARS polypeptide, respectively, in a cell, tissue, or subject. One possible measurement of the level of TARS polypeptide-encoding nucleic acid or polypeptide is a measurement of an absolute level of TARS polypeptide-encoding nucleic acid or TARS polypeptide. This could be expressed, for example, in the level of TARS polypeptide-encoding nucleic acid or polypeptide per unit of cells or tissue. Another measurement of a level of TARS polypeptide-encoding nucleic acid or TARS polypeptide is a measurement of the change in the level of the TARS polypeptide-encoding nucleic acid or TARS polypeptide over time. This may be expressed in an absolute amount or may be expressed in terms of a percentage increase or decrease over time. Antibodies or antigen-binding fragments or other compounds that specifically bind a TARS polypeptide or a nucleic acid that encodes a TARS polypeptide may be used in embodiments of methods of the invention to assess TARS polypeptide and TARS polypeptide-encoding nucleic acid molecules to assess the status of a cancer or proliferative disease or condition and/or the efficacy of treatments for cancer or other proliferative disease or condition.

The present invention, in some aspects, provides methods of determining a prognosis in a subject that has a disease or condition associated with an altered TARS activity. A prognosis for a subject having such a disease or condition can be determined by measuring levels of TARS in a biological sample obtained from a subject to be tested. Expression and/or activity of TARS in the biological sample that is greater than a control level indicates a worse prognosis for the subject. Such methods can be used to assess the prognosis of a disease or condition associated with altered TARS activity. Examples of prognoses may include, but are not limited to, determination of the likelihood of metastases in a cancer, the likelihood of recovery from or remission in the disease or condition, the likelihood of progression of the disease or condition.

The present invention further provides methods for determining the metastatic potential of a cancer and/or tumor by measuring the level of TARS expression and/or activity in a biological sample of the cancer, tumor or fluid sample that is obtained from the subject. Expression and/or activity of TARS in the cancer tissue or fluid that is greater than a control level for that particular cancer or tumor tissue may indicate an increased metastatic potential of that cancer or tumor in the subject. In some embodiments, a greater level of TARS in a sample from a subject indicates versus a control level correlates with an increased risk of metastases of the cancer in the subject. Thus, an increase in a level of TARS in a subject known to have cancer that is at least 5%, 10%, 15%, 20%, 30%, 40%, 50%, 60%, 70%, 80%, 90%, 100%, 125%, 150%, or 200%, above a level that is diagnostic for the cancer may indicate an increased likelihood and risk of metastasis of the cancer in the subject and angiogenic status of the tumor. This type of information can be used by a health-care professional to help determine a medically appropriate course of treatment for the subject. For example, a determination that a subject is at higher risk of metastases from a cancer may suggest use of a more aggressive treatment of the cancer than if a lower risk of metastases is determined. Thus, for example, if an elevated level of TARS is measured in a subject known to have prostate cancer and the level is beyond that which is diagnostic for the cancer itself, this may indicate increased risk that the cancer will metastasize in the subject. Such an indication determined in a subject with a cancer, (e.g., ovarian cancer, prostate cancer, etc.) may indicate a need for more aggressive surgical treatment, radiation treatment, and/or chemotherapy treatment than if an increased level of TARS activity is not present. In addition, a measure of the angiogenic state of the tumor could provide information related to the use of anti-angiogenic treatment in patients that exhibit higher than normal TARS in their tumor or fluid samples.

Changes in a subject's condition can also be monitored using methods of the present invention by comparing changes in TARS levels and/or activity in cells and tissues in biological samples obtained from the subject at two or more time points. Thus, a first level of TARS can be determined in a sample obtained from a subject at a first time point and a second level of TARS can be determined in a subsequent sample obtained from the subject at a second time point and the levels in the samples can be compared. For a disorder characterized by higher TARS activity, a lower TARS level in a first sample compared to the level in a second sample from the same subject can be used to determine the onset or progression of a disease or condition and a higher TARS level in the first sample compared to the level in the second sample can indicate regression of the disease or condition. Similarly, for a disorder characterized by lower TARS activity, a higher TARS level in a first sample compared to the level in a second sample from the same subject can be used to determine the onset or progression of a disease or condition and a lower TARS level in the first sample compared to the level in the second sample can indicate regression of the disease or condition in the subject. Such information about the stage or status of the disease or condition can be used to assist a health-care provider to select a treatment for administration to the subject or can be used by a health-care professional to adjust (e.g., increase, decrease, or stop) a treatment that is being provided to the subject.

As used herein a "subject" refers to any warm-blooded animal, such as, but not limited to a human, a non-human primate, a rodent, a dog, cat, or other animal. Thus, in addition to human medical application, some aspects of the invention include veterinary application of methods described herein. A subject may be known to have a disease or condition characterized by an altered TARS activity as compared to a control level, and thus may be a subject diagnosed with the disease or condition. In some embodiments, a subject may not have been previously or currently diagnosed with such a disease or condition, but may be considered to be at risk of for having the disease or condition, for example, a subject who may be free of a detectable disease or condition in which TARS activity is altered. In some embodiments of the invention, a subject may have previously been diagnosed with a disease, for example diagnosed with a cancer, but the subject may be in remission at the time a diagnostic test is performed using methods of the invention.

In some embodiments of the invention, a biological sample comprises a cell or tissue or extracellular material from a subject. In some embodiments a sample is a tumor sample. A tissue sample or tumor sample may comprise tissue or a suspension of cells. A tissue section, for example, a freeze-dried, paraffin embedded, or fresh frozen section of tissue removed from a subject, or a section of a tumor biopsy can be used as the biological sample. Moreover, a biological sample may be a biological fluid obtained from a subject (e.g., blood, Aqueous humour and vitreous humour, bile, blood, serum, breast milk, cerebrospinal fluid, lymph, female or male ejaculate, gastric fluid, mucus, peritoneal fluid, plural fluid, saliva, sebum, semen, sweat, tears, vaginal secretion, urine, ascites, spinal fluid, etc.). Following collection, fluids, cells, tissues, tumor or other biological samples can be stored at temperatures below −20° C. to prevent degradation until the detection method is to be performed. In some embodiments of the invention, a biological sample in which a TARS molecule is to be detected is a prostate or ovarian tissue and/or tumor sample. In certain embodiments of the invention, a biological sample in which TARS mRNA or TARS polypeptide is to be detected is, for example, a prostate, colon, cervical, ovarian, or other tumor. In some aspects of the invention, a biological sample may comprise TARS that has been secreted from the cell in which it was produced. In certain aspects of the invention, a biological sample may comprise a TARS molecule that is a non-secreted molecule, which as used herein, is a TARS molecule that was produced in a cell but not secreted by that cell into the extracellular environment.

Biological samples for use in methods of the invention (e.g., for diagnostic purposes) may be obtained from any number of sources. A sample obtained directly from a cancer or tumor, such as the stroma or cytosol, may be used to determine the metastatic potential of the cancer or tumor. Such diagnostic methods may be useful to monitor progress of a subject, such as after surgery to remove a tumor. If a reference (e.g., control or baseline) TARS level determination is made in a sample after the operation, and one or more additional determinations are made in samples taken from the subject at later times, any increase in the level of TARS could be indicative of a relapse, or possibly a metastasis.

As used herein, the term "isolated", when used in the context of a biological sample, is intended to indicate that the biological sample has been removed from a subject. In some embodiments of the invention, a biological sample comprises a sample that has been isolated from a subject and is subjected to a method of the present invention without further processing or manipulation subsequent to its isolation. In some embodiments of the invention, a biological sample can be processed or manipulated subsequent to being isolated and prior to being subjected to a method of the invention. For example, a sample can be refrigerated (e.g., stored at 4° C.), frozen (e.g., stored at −20° C., stored at −135° C., frozen in liquid nitrogen, or cryopreserved using any one of many standard cryopreservation techniques known in the art). Furthermore, a sample can be purified subsequent to isolation from a subject and prior to subjecting it to a method of the present invention.

As used herein, the term "purified" when used in the context of a biological sample, is intended to indicate that at least one component of the isolated biological sample has been removed from the biological sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a tissue or tumor sample can be purified such that substantially only the polypeptide or mRNA component of the biological sample remains.

Furthermore, it may be desirable to amplify a component of a biological sample such that detection of the component is facilitated. For example, the mRNA component of a biological sample can be amplified (e.g., by RT-PCR) such that detection of TARS mRNA is facilitated. As used herein, the term "RT-PCR" (an abbreviation for reverse transcriptase-polymerase chain reaction) involves subjecting mRNA to the reverse transcriptase enzyme, resulting in the production of a cDNA which is complementary to the base sequences of the mRNA. Large amounts of selected cDNA can then be produced by means of the polymerase chain reaction which relies on the action of heat-stable DNA polymerase for its amplification action. Alternative amplification methods include: self-sustained sequence replication (Guatelli, J. C. et al., 1990, Proc. Natl. Acad. Sci. USA 87: 1874-1878), transcriptional amplification system (Kwoh, D. Y. et al., 1989, Proc. Natl. Acad. Sci. USA 86: 1173-1177), Q-Beta Replicase (Lizardi, P. M. et all, 1988, Bio/Technology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

TARS Detection Techniques

TARS molecules (for example, TARS polypeptides and nucleic acids that encode TARS polypeptides), can be detected and measured using any suitable means known in the art. In some embodiments of the invention, a detection or measurement means for TARS molecules includes an immunological assay, nucleotide determination (mRNA or DNA), mass spectrometry assessment, TARS aminoacylation assay, TARS active site determination assay, or a TARS binding assay that may include a TARS-binding reporter molecule. Examples of immunological assays suitable for use in methods of the invention may include, but are not limited to ELISA assays, assays that utilize an anti-TARS antibody (or FV derivative) to which is conjugated a detectable label, (examples of which include but are not limited to a radiolabel, non-limiting examples of which are technicium and indium). In some aspects of the invention, TARS levels may be measured in complex mixtures using an amino acid (threonine) activation assay, aminoacylation assay, or binding of a threonine specific tRNA, or a nucleic acid aptamer designed and selected to bind to threonyl-tRNA synthetase.

In some embodiments of the invention, levels of a TARS polypeptide may be detected in complex protein mixtures using mass spectrometry methods, which may include a TARS-specific peptide as an internal standard to allow quantitation. Methods of measuring levels of nucleic acids encoding TARS (i.e. TARS mRNA) may include, but are not limited to, real-time polymerase chain reaction (qRT-PCR), DNA array, and next generation sequencing methods.

The present invention features agents that are capable of detecting and/or quantitating a TARS polypeptide or a TARS-encoding nucleic acid such that the presence and/or level of TARS are determined. As defined herein, an "agent" refers to a substance that is capable of identifying or detecting TARS in a biological sample (e.g., identifies or detects TARS mRNA, TARS DNA, TARS polypeptide, TARS activity, etc.). In some embodiments of the invention, the agent is a labeled or a labelable antibody or molecule (e.g., a binding partner) that specifically binds to a TARS polypeptide. It will be understood that as used herein, the term "polypeptide" is used in reference to an amino acid sequence of a full-length TARS protein or a portion of a TARS protein. As used herein, the terms "labeled" or "labelable" refers to the attaching or including of a label (e.g., a marker or indicator) or ability to attach or include a label (e.g., a marker or indicator). Markers or indicators useful in methods of the invention may include, but are not limited to, for example, radioactive molecules, colorimetric molecules, and enzymatic molecules that produce detectable changes in a substrate.

In some embodiments of the invention, an agent is an antibody that specifically binds to all or a portion of a TARS polypeptide. As used herein, the phrase "specifically binds" refers to binding of, for example, an antibody to an epitope or antigen or antigenic determinant in such a manner that binding can be displaced or competed with a second preparation of identical or similar epitope, antigen or antigenic determinant. In an exemplary embodiment, the agent is an antibody that specifically binds to all or a portion of the human TARS polypeptide. In some embodiments of the invention, an ELISA is used in conjunction with the antibody to determine the presence and/or level of TARS polypeptide in a biological sample. Methods of the invention for detecting the presence and/or quantity of a TARS molecule may also include procedures such as an immunological assay, a polymerase chain reaction, real-time polymerase chain reaction (qRT-PCR), mass spectrometry, a TARS aminoacylation assay, TARS active site determination assay, or a TARS binding assay comprising a TARS-binding reporter molecule. In addition, embodiments of the invention include may include nucleic "aptamers", i.e. nucleic acids (DNA, RNA or peptide nucleic acids [PNAs]) that possess high affinity for TARS derived polypeptides and can be readily labeled for high throughput binding assays. Aptamers can be produced by standard molecular biological techniques by those skilled in the art by repeated rounds of binding, selection, and affinity, and amplification (Hamaguchi, et al. *Anal. Biochem*. (2001) 294; pt 2, pages 126-131).

In some embodiments of the invention an agent is a labeled or labelable nucleic acid probe capable of hybridizing to a TARS nucleic acid, (e.g., a TARS RNA or DNA). For example, the agent can be an oligonucleotide primer for the polymerase chain reaction that flanks or lies within the nucleotide sequence encoding human TARS. In some embodiments of the invention, the biological sample being tested is an isolate, for example, RNA. In yet another embodiment, the isolate (e.g., the RNA) is subjected to an amplification process that results in amplification of TARS nucleic acid. As defined herein, an "amplification process" is designed to strengthen, increase, or augment a molecule within the isolate. For example, where the isolate is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

TARS Nucleic Acid Binding Agents

Types of agents that can be used to determine levels of TARS-encoding nucleic acids may include, but are not limited to cDNA, riboprobes, synthetic oligonucleotides and genomic probes. The type of agent (e.g. probe) used will generally be dictated by the particular situation, such as riboprobes for in situ hybridization, and cDNA for Northern blotting, for example. Most preferably, the probe is directed to nucleotide regions unique to the polypeptide. Detection of the TARS-encoding gene, per se, will be useful for diagnostic methods of the invention and for screening for mutations associated with enhanced expression. Other forms of assays to detect targets more readily associated with levels of expression—transcripts and other expression products—will generally be useful as well. A probe may be as short as is required to differentially recognize TARS mRNA transcripts, and may be as short as, for example, 15 bases; however, probes of at least 17 bases, 18 bases, 19, bases, 20 bases, or more may be used.

A probe may also be reverse-engineered by one skilled in the art, for example using the amino acid sequence of GENBANK™ Accession No.:NM_152295. However use of such probes may be more limited than the native DNA sequence, as it will be appreciated that any one given reverse-engineered sequence will not necessarily hybridize well, or at all, with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

The form of labeling of a probe used in an embodiment of the invention may be any that is appropriate, such as the use of radioisotopes, for example, $^{32}P$ and $^{35}S$, etc. Labeling with radioisotopes may be achieved, whether the probe is synthesized chemically or biologically, by the use of suitably labeled bases using methods well known in the art.

TARS RNA Detection Techniques

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using known amplification methods. For example, it is within the scope of the present invention to reverse transcribe mRNA into cDNA followed by real-time polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR). Each of these methods is well known and routinely used in the art. Other known amplification methods can also be utilized in methods of the invention, including, but not limited to:

In situ hybridization visualization may also be employed, wherein a radioactively labeled antisense RNA probe is hybridized with a thin section of a biopsy sample, washed, cleaved with RNase and exposed to a sensitive emulsion for autoradiography. Biological samples may be stained with haematoxylin to demonstrate the histological composition of the sample, and dark field imaging with a suitable light filter shows the developed emulsion. Non-radioactive labels such as digoxigenin, etc. may also be used.

TARS Antibodies and Additional Binding Agents

It will be appreciated that antibodies for use in accordance with diagnostic methods of the present invention may be monoclonal or polyclonal as appropriate. Antibody equivalents of these may comprise: the Fab' fragments of the antibodies, such as Fab, Fab', F(ab')2 and Fv; idiotopes; or the results of allotope grafting (where the recognition region of an animal antibody is grafted into the appropriate region of a human antibody to avoid an immune response in the patient), for example. Single chain antibodies may also be used. Other suitable modifications and/or agents will be apparent to those skilled in the art. Chimeric and humanized antibodies are also within the scope of the invention and a variety of approaches for making chimeric antibodies are known in the art. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art.

In addition to using antibodies to bind to and for detection of a TARS molecule in diagnostic methods of the invention, it may also be possible to use other molecules or compounds that bind to a TARS molecule in diagnostic methods. For example, it may be possible to identify antagonists, compounds, and/or molecules such as polypeptides that specifically bind to a TARS molecule. In addition, it may also be possible to use an antibody or other compound or molecule that binds to, and permits detection of a TARS molecule in a biological sample. In some embodiments a TARS molecule will detected as part of a complex with one or more additional polypeptides. One non-limiting example of a binding molecule that may be useful in methods of the invention is a von Hippel Lindau (VHL) polypeptide. VHL polypeptides bind to and form a complex with TARS, and in some embodiments of the invention may be used as an agent to detect the presence and/or to quantify a TARS molecule in a biological sample. Other polypeptides include, but are not limited to, eukaryotic elongation factor EF1A1, or Poly ADP ribose polymerase (PARP), as shown in FIG. 16.

An isolated TARS polypeptide, or fragment thereof, can be used as an immunogen to generate antibodies that bind TARS using standard techniques for polyclonal and monoclonal antibody preparation. The full-length TARS polypeptide can be used or, alternatively, the invention provides antigenic peptide fragments of TARS for use as immunogens. The antigenic peptide of TARS may comprise at least 8 amino acid residues of the amino acid sequence shown in GENBANK™ Accession No.:NM_152295 and encompasses an epitope of TARS such that an antibody raised against the peptide forms a specific immune complex with TARS. Polypeptides that may be used as immunogens include but are not limited to the sequence set forth as SEQ ID NO:7 RAELNPWPEYIYTRLEMYNILKAEHDSILAE-KAEKDSKPIKVTLPDGKQVDAESWKTTPYQIACGIS-QGLADNTVIAKVNNVVWDLDRPLEEDCTLELLK, which is a portion of the sequence set forth in GENBANK™ Accession No.:NM_152295. In some aspects of the invention, an antigenic peptide may comprise at least 10, 11, 12, 13, 14, 15, 16, 17, 18, 19, 20, 21, 22, 23, 24, 25, 26, 27, 28, 29, 30, or more residues. Antigenic polypeptides comprising at least 50, 100, 150, 200 or 250 amino acid residues are also within the scope of the present invention. Preferred epitopes encompassed by the antigenic peptide are regions of TARS that are located on the surface of the polypeptide, e.g., hydrophilic regions.

A TARS immunogen typically may be used to prepare antibodies by immunizing a suitable subject, (e.g., rabbit, goat, mouse or other mammal) with the immunogen. An appropriate immunogenic preparation can contain, for examples, recombinantly expressed TARS polypeptide or a chemically synthesized TARS polypeptide. The preparation can further include an adjuvant, such as Freund's complete or incomplete adjuvant, or similar immunostimulatory agent. Immunization of a suitable subject with an immunogenic TARS preparation induces a polyclonal anti-TARS antibody response. The immunogen may further include a portion of non-TARS polypeptide, for example, a polypeptide useful to facilitate purification.

Accordingly, another aspect of the invention pertains to the use of anti-TARS antibodies to determine the level and activity of TARS polypeptides. The term "antibody" as used herein refers to immunoglobulin molecules and immunologically active portions of immunoglobulin molecules, i.e., molecules that contain an antigen binding site which specifically binds (immunoreacts with) an antigen, such as TARS. The invention may include use of polyclonal and monoclonal antibodies that bind TARS. The term "monoclonal antibody" or "monoclonal antibody composition", as used herein, refers to a population of antibody molecules that contain only one species of an antigen binding site capable of immunoreacting with a particular epitope of TARS. A monoclonal antibody composition thus typically displays a single binding affinity for a particular TARS polypeptide with which it immunoreacts.

Polyclonal antibodies generated by the above or another technique may be used directly, or suitable antibody producing cells may be isolated from the animal and used to form a hybridoma by known means [Kohler and Milstein, Nature 256:795. (1975)]. Selection of an appropriate hybridoma will also be apparent to those skilled in the art, and the resulting antibody may be used in a suitable assay to identify and/or quantify a TARS molecule.

TARS Protein Detection Techniques

Methods of the invention may include the use of diagnostic molecules (e.g., antibodies, antibody equivalents, binding molecules, etc.) to detect TARS polypeptides. Methods for the detection of polypeptides are well known to those skilled in the art, and include ELISA (enzyme linked immunosorbent assay), RIA (radioimmunoassay), Western blotting, and immunohistochemistry. Methods for immunoassays are routinely used and are well known in the art.

ELISA and RIA procedures may be conducted such that a TARS standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, TARS in the sample is allowed to react with the corresponding immobilized antibody, radioisotope- or enzyme-labeled anti-TARS antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay may involve contacting antigen with immobilized antibody and, without washing, contacting the mixture with labeled antibody. A "two-step" assay may involve washing before contacting the mixture with labeled antibody. Other conventional methods may also be employed as suitable.

Enzymatic and radiolabeling of a detection agent (e.g., antibodies, binding molecules, etc.) may be carried out by conventional means. Such means will generally include covalent linking of the enzyme to the detection agent, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of an assay system on a support, thereby allowing other components of the system to be brought into contact with the component and readily removed without laborious and time-consuming labor. It is possible for a second phase to be immobilized away from the first, but one phase may be sufficient.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled detection agent with the substrate under controlled conditions well-known in the art.

Other techniques may be used to detect TARS molecules according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-TARS antibodies (unlabeled) are then brought into contact with the support and assayed by a secondary immunological reagent, such as labeled protein A or anti-immunoglobulin (suitable labels including but not limited to $^{125}$I, horseradish peroxidase and alkaline phosphatase). Chromatographic detection may also be used.

Immunohistochemistry may be used to detect expression of human TARS in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay may be scored visually, using microscopy, or using any other suitable methods.

TARS Detection Kit

The invention also encompasses kits for detecting the presence of TARS in a biological sample (e.g., a cell sample, tissue sample, tumor sample, etc.). For example, a kit can comprise a labeled or labelable agent capable of detecting TARS polypeptide or nucleic acid (e.g., RNA, DNA, etc.) in a biological sample and a means for determining the amount of TARS in the sample. The agent can be packaged in a suitable container. The kit can further comprise a means for comparing the amount of TARS in the sample with a standard and/or can further comprise instructions for using the kit to detect TARS nucleic acid or polypeptide.

This invention in some aspects also provides a kit for measuring human TARS. Such a kit may include a diagnostic agent (e.g., an antibody or antibody fragments, or binding molecule, etc.) that selectively bind human TARS or a set of DNA oligonucleotide primers that allows synthesis of cDNA encoding the polypeptide or a DNA probe that detects expression of TARS mRNA, etc. In some embodiments of the invention, the primers and probes may comprise at least 15, 16, 17, 18, 19, 20, 21, 22, 23, 24, or more nucleotides and hybridize under stringent conditions to a DNA fragment having the nucleotide sequence set forth in GENBANK™ Accession No.: NM_152295. As herein used, the term "stringent conditions" means hybridization will occur only if there is at least 85%, 90%, 91%, 92%, 93%, 94%, 95%, 96%, 97%, 98%, or at least 99%, identity between the sequences.

Methods of Detection

The invention in some aspects provides methods for detecting the presence of a TARS molecule in a biological sample. The method may comprise contacting the biological sample with an agent capable of detecting TARS polypeptide or nucleic acid molecules (e.g., TARS mRNA or DNA, etc.) such that the presence of TARS is detected in the biological sample. An agent for detecting TARS mRNA using methods of the invention may be a labeled or labelable nucleic acid probe capable of hybridizing to TARS mRNA. The nucleic acid probe may be, for example, the full-length TARS cDNA of GENBANK™ Accession No. NM_152295 or a portion thereof, such as an oligonucleotide of at least 15, 30, 50, 100, 250 or 500 nucleotides in length and sufficient to specifically hybridize under stringent conditions to TARS mRNA.

A non-limiting example of an agent that may be used in methods of the invention for detecting TARS polypeptide is a labeled or labelable antibody capable of binding to TARS polypeptide. Antibodies can be polyclonal or monoclonal antibodies. An intact antibody, or a fragment thereof (e.g., Fab or F (ab') 2) can also be used.

The term "labeled or labelable", with regard to the probe or antibody, is intended to encompass direct labeling of the probe or antibody by coupling (i.e., physically linking) a detectable substance to the diagnostic molecule (e.g., probe, antibody, binding molecule, etc.), as well as indirect labeling of the diagnostic molecule by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Detection methods useful in methods of the invention, including but not limited to those described above herein, can be used as the basis for a method of diagnosis of a subject with a tumor and/or cancer (e.g., a prostate tumor, ovarian cancer, etc.), can be used as the basis for a method of monitoring the progression of the tumor and/or cancer in a subject, or can be used as the basis for a method of determining a prognosis for a subject at risk for developing a cancer or tumor.

In one embodiment, the invention features methods of determining the metastatic potential of a tumor and the methods may involve contacting a sample of the tumor (or isolate) with an agent capable of detecting TARS polypeptide or nucleic acid (e.g., mRNA etc.) such that the presence and/or level of TARS polypeptide or nucleic acid detected in the tumor sample or isolate, thereby determining the metastatic potential of the tumor. Another aspect of the invention features a prognostic method for determining whether a subject is at risk for developing cancer that involves contacting a biological sample obtained from the subject (or isolate of the sample) with an agent capable of detecting TARS polypeptide or nucleic acid such that the presence and/or level of TARS polypeptide or nucleic acid is detected in the biological sample or isolate, thereby determining whether the subject is at risk for developing cancer. Yet another aspect of the invention features a method of diagnosing cancer in a subject and that involves contacting a biological sample obtained from the subject (or isolate of the sample) with an agent capable of detecting TARS polypeptide or nucleic acid such that the presence and/or level of TARS polypeptide or nucleic acid is detected in the biological sample or isolate, thereby diagnosing cancer in the subject.

In some aspects and embodiments of diagnostic methods of the present invention may include determining the level of TARS polypeptide or nucleic acid in the sample or isolate. In certain embodiments, diagnostic methods of the present invention may include comparing the level of TARs polypeptide or nucleic acid in a sample or isolate with the level of TARS polypeptide or nucleic acid in a control sample. In yet another embodiment, a diagnostic or prognostic method of the invention may also include a step of forming a prognosis or forming a diagnosis, and may also include a step of determining an appropriate treatment for a subject by a health-care provider based at least in part on the determination of the TARS level in a sample from the subject.

In some embodiments of the invention, a control level of TARS activity is a level determined from cells that do not have the disease or condition associated with altered TARS activity that is being tested for in the subject's sample. For example, in some embodiments, a control level of TARS is a level determined in normal cells that do not have a cancer that is suspected to be in the biological sample obtained from the subject. In such a case, a primary malignancy of a subject's tumor/cancer cell sample can be diagnosed based on an increase in the level of expression of TARS nucleic acid or polypeptide in the subject's sample as compared to the control that is free of the cancer. In another embodiment, the control is from normal cells or a primary tumor and the subject's tumor sample is a suspected metastatic tumor sample. Acquisition of the metastatic phenotype by the suspected metastatic tumor sample can be diagnosed as described elsewhere herein, based on an increase in the level of TARS polypeptide or nucleic acid in the subject's tumor sample or bodily fluid compared to the control. In another embodiment, determining the level of a TARS molecule can be carried out in conjunction with the determination of one or more other biomarkers for cancer or a proliferative disease or condition. For example, the level of a TARS molecule (e.g., nucleic acid that encodes a TARS polypeptide, a TARS polypeptide or signature fragment thereof, may be detected using a panel that also permits detection at least one additional molecule whose expression and/or level is may be useful to characterize a cancer or other proliferative disease or condition. For example, a panel of the invention may include a means to determine the level and/or activity TARS and a means to determine the level and/or activity of each of one or more other markers that may characterize a cancer or other proliferative disease or condition to generate an aggregate "biomarker panel signature" to improve diagnosis and treatment strategies. Additional biomarkers that may be assessed using an embodiment of a biomarker panel invention include, but are not limited to: TNF-α, eEF-1α, IL-6, CA125, VEGF, autoantibodies to aminoacyl tRNA synthetases, and other biomarkers associated with ovarian cancer as previously referenced (Altundag et al. 2005; Mor, Visintin et al. 2005). A biomarker panel of the invention may include detection means for at least 1, 2, 3, 4, 5, 6, 7, 8, 9, 10, 11, 12, 13, 14, 15, 20, 30, 50, 100 or more biomarkers (including each integer in between the listed integers) in addition to a detection means for TARS.

TARS Nucleic Acid and Polypeptide Sequences and Variations

One aspect of the invention involves isolated nucleic acid molecules that encode TARS or biologically active portions thereof, as well as nucleic acid fragments sufficient for use as hybridization probes to identify TARS-encoding nucleic acid. As used herein, the term "nucleic acid molecule" is intended to include DNA molecules (e.g., cDNA or genomic DNA) and RNA molecules (e.g., mRNA). A nucleic acid molecule may be single-stranded or double-stranded or may be a double-stranded DNA molecule. An "isolated" nucleic acid molecule is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, may be free of other cellular material.

In some aspects of the invention, an isolated nucleic acid molecule of the invention comprises the nucleotide sequence shown in GENBANK™ Accession No.: NM_152295 The sequence of GENBANK™ Accession No. NM_152295 corresponds to the human TARS cDNA. This cDNA comprises sequences encoding the TARS polypeptide (i.e., "the coding region", from nucleotides 1 to 2850), and 3' untranslated sequences (nucleotides 2468-2850). Alternatively, the nucleic acid molecule may comprise only the coding region of GENBANK™ Accession No NP_689508 (e.g., nucleotides 296-2467).

The invention further encompasses nucleic acid molecules that differ from the sequence set forth in GENBANK™ Accession No. NM_152295 (and portions thereof) due to degeneracy of the genetic code and thus encode the same TARS protein as that encoded by the sequence set forth in GENBANK™ Accession No. NM_152295. Accordingly, in another embodiment, an isolated nucleic acid molecule of the invention has a nucleotide sequence encoding a protein having an amino acid sequence as set forth in GENBANK™ Accession No. NM_152295. Moreover, the invention encompasses nucleic acid molecules that encode biologically active portions of the sequence set forth in GENBANK™ Accession No. NM_152295.

A nucleic acid molecule having the nucleotide sequence as set forth in GENBANK™ Accession No. NM_152295, or a portion thereof, can be isolated using standard molecular biology techniques and the sequence information provided herein. For example, a human TARS cDNA library using all or portion of the sequence set forth in GENBANK™ Accession No. NM_152295 as a hybridization probe and standard hybridization techniques (e.g., as described in Sambrook, J., Fritsh, E. F., and Maniatis, T. Molecular Cloning: A Laboratory Manual. 2nd. edition, Cold Spring Harbor Laboratory, Cold Spring Harbor, N.Y., 1989). Moreover, a nucleic acid molecule encompassing all or a portion of the sequence set forth as GENBANK™ Accession No.: NM_152295 can be isolated using any suitable method, including as a non-limiting example, use of the polymerase chain reaction using oligonucleotide primers designed based upon the sequence set forth as GENBANK™ Accession No.: NM_152295. For example, TARS mRNA can be isolated from cells using standard, art-known methods and cDNA can be prepared using reverse transcriptase and art-known methods. Synthetic oligonucleotide primers for PCR amplification can be designed based upon the nucleotide sequence set forth in GENBANK™ Accession No. NM_152295 and nucleic acids of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TARS nucleotide sequence can be prepared by standard synthetic techniques, e.g., using an automated DNA synthesizer.

In addition to the human TARS nucleotide sequence set forth as GENBANK™ Accession No.: NM_152295, it will be appreciated by those skilled in the art that DNA sequence polymorphisms that lead to changes in the amino acid sequences of TARS may exist within a population (e.g., the human population). Such genetic polymorphism in the TARS gene may exist among individuals within a population due to natural allelic variation. Such natural allelic variations can typically result in 1-5% variance in the nucleotide sequence of a gene. Any and all such nucleotide variations and resulting amino acid polymorphisms in TARS that are the result of natural allelic variation and that do not alter the functional activity of TARS are intended to be within the scope of the invention. Moreover, nucleic acid molecules encoding TARS polypeptides from other species, and thus which have a nucleotide sequence that differs from the human sequence set forth as GENBANK™ Accession No.: NM_152295, are intended to be within the scope of the invention. Nucleic acid molecules corresponding to natural allelic variants and nonhuman homologues of the human TARS cDNA of the invention can be isolated based on their homology to the human TARS nucleic acid disclosed herein using the human cDNA, or a portion thereof, as a hybridization probe—according to standard hybridization techniques under stringent hybridization conditions, which are recognized in the art.

In some aspects of the invention, an isolated nucleic acid molecule of the invention that hybridizes under stringent conditions to the sequence set forth in GENBANK™ Accession No.: NM_152295 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human TARS.

In addition to naturally-occurring allelic variants of the TARS sequence that may exist in the population, the skilled artisan will further appreciate that changes may be introduced by mutation into the nucleotide sequence set forth as GENBANK™ Accession No. NM_152295 thereby leading to changes in the amino acid sequence of the encoded TARS protein, without altering the functional ability of the TARS protein. For example, nucleotide substitutions leading to amino acid substitutions at "non-essential" amino acid residues may be made in the sequence set forth as GENBANK™ Accession No. NM_152295. A "non-essential" amino acid residue is a residue that can be altered from the wild-type sequence of TARS polypeptide (e.g., the sequence set forth as GENBANK™ Accession No. NM_152295) without altering the activity of TARS, whereas an "essential" amino acid residue is required for TARS activity.

Accordingly, another aspect of the invention pertains to nucleic acid molecules encoding TARS polypeptides that contain changes in amino acid residues that are not essential for TARS activity, e.g., residues that are not conserved or only semi-conserved among members of the subfamily. Such TARS polypeptides differ in amino acid sequence from the sequence set forth as GENBANK™ Accession No. NM_152295 yet retain TARS activity. In one embodiment, the isolated nucleic acid molecule comprises a nucleotide sequence encoding a protein, wherein the protein comprises an amino acid sequence at least 70%, 75%, 80%, 85%, 90%, 95%, 97%, or at least 99% similar to the amino acid sequence set forth as GENBANK™ Accession No.: NM_152295 and retains a level of TARS activity.

To determine the percent similarity of two amino acid sequences (e.g., GENBANK™ Accession No. NM_152295 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., GENBANK™ Accession No. NM_152295) is occupied by the same amino acid residue as the corresponding position in the other sequence (e.g., a mutant form of TARS), then the molecules have identity at that position (i.e., as used herein amino acid "similarity" is equivalent to amino acid "identity"). If two sequences are 'homologous' they are descended from a common ancestor. The percent similarity between the two sequences is a function of the number of identical positions shared by the sequences (i.e., % similarity=number of identical positions/total number of positions×100). Such an alignment can be performed using any one of a number of well-known computer algorithms designed and used in the art for such a purpose.

An isolated nucleic acid molecule encoding a TARS polypeptide that has identity to the protein of GENBANK™ Accession No.: NM_152295 can be created by introducing one or more nucleotide substitutions, additions or deletions into the nucleotide sequence of GENBANK™ Accession No.: NM 152295 such that one or more amino acid substitutions, additions or deletions are introduced into the encoded polypeptide. Mutations can be introduced into the sequence set forth as GENBANK™ Accession No. NM_152295 by standard techniques, such as site-directed mutagenesis and PCR-mediated mutagenesis. In some embodiments of the invention conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in TARS may be replaced with another amino acid residue from the same side chain family. Alternatively, in another embodiment, mutations can be introduced randomly along all or part of a TARS coding sequence, such as by saturation mutagenesis, and the resultant mutants can be screened for TARS activity to identify mutants that retain TARS activity. Following mutagenesis of a sequence such as that set forth as GENBANK™ Accession No. NM_152295, the encoded protein can be expressed recombinantly and the TARS activity of the polypeptide can be determined, for example using an assay described herein or other suitable assay.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Threonyl tRNA Synthetase (TARS) is an Angiogenic Chemokine Secreted by Endothelial Cells in Response to VEGF Materials and Methods for Example 1

Cell Culture, Reagents and Antibodies—

Human umbilical vein endothelial cells (HUVEC) (a gift from C. Holmes, University of Vermont) were grown in Clonetics® EGM®-2 complete media (Lonza, Annandale, N.J.). Borrelidin analog BC194 was a gift from Dr. Barrie Wilkinson, (Biotica). Purified basic-fibroblast growth factor (bFGF) was a gift from J. Spees, Univ. of Vermont. Retinoic acid and cycloheximide were purchased from Sigma-Aldrich, and VEGF and TNF-α were purchased from Cell Signaling Technology, Danvers, Mass. and Calbiochem, San Diego, Calif., respectively.

Western Blot—

After treatments, cells were harvested into sample buffer containing: 0.2 M Tris-HCL, 4% SDS, 4% β-mercaptoethanol, 40% glycerol, 4 µM pyronin Y. Extracts were sheared through a 24-gauge syringe. Samples were separated by 10% SDS-PAGE and transferred to nitrocellulose membrane and probed with specific antibody as described (Lounsbury, Beddow et al. 1994). Primary antibodies are as follows: Rabbit monoclonal anti-P-eIF2α (1:1000; Cell Signaling Technology, Danvers, Mass.), rabbit monoclonal anti-Cleaved Caspase-3 (1:1000; Cell Signaling Technology, Danvers, Mass.), rabbit polyclonal anti-TARS (1:500; Santa Cruz Biotechnology, Santa Cruz, Calif.). Loading control antibodies were rabbit monoclonal anti-β-actin and anti-β-tubulin (1:1000; Cell Signaling Technology, Danvers, Mass.). Secondary antibodies were HRP-goat-anti-mouse and HRP-goat-anti-rabbit (1:5,000; Jackson Laboratories, Bar Harbor, Me.).

In Vitro Tube Formation Assay—

Tube formation assays were performed as described (Arnaoutova and Kleinman 2010; Cassavaugh, Hale et al., 201). Human Umbilical Vein Endothelial Cells (HUVECs) were seeded in 48-well plates ($1.5 \times 10^4$ cells/well) coated with 100 µl of Matrigel™ Basement Membrane Matrix Growth Factor Reduced (BD Biosciences, San Jose, Calif.) and incubated in Clonetics® EGM®-2 complete media (Lonza, Annandale, N.J.) or EGM®-2 with reduced serum (0.2% fetal bovine serum). Cells were incubated at 37° C. for 6 h then fixed in 10% formalin. Fixed samples were imaged by phase-contrast microscopy or stained with Oregon Green 488 Phalloidin (Molecular Probes, Eugene, Oreg.) then imaged with fluorescence microscopy (2× objective). Number of tubes and tube lengths (in pixels) were quantified using the Simple Neurite Tracer (Longair, Baker et al. 2011) plug-in on ImageJ software (NIH). Statistical analysis of one-way ANOVA was performed with GraphPad Software. Multiple comparisons were performed using the Tukey Test.

Cell Viability—

Cell viability was measured by counting cells in a hemacytometer with Trypan Blue exclusion (Sigma-Aldrich, St. Louis, Mo.) according to manufacturer's instructions. Measurements were normalized to untreated cells.

Nascent Protein Synthesis Assay—

Nascent protein synthesis was measured using Invitrogen Click-iT® metabolic labeling reagents [Dieterich, D. C., et al., Nat Protoc 2, 532-40 (2007)]. 1). HUVEC cultures were pre-incubated in methionine-free Dulbecco's Modified Eagle Medium (D-MEM) high glucose (Invitrogen, Life Technologies, Grand Island, N.Y.) supplemented with 10% dialyzed fetal bovine serum (Invitrogen) containing the control or test compounds. Cycloheximide (50 µM) was used as a positive control. After 45 minutes, 25 µM Click-iT® AHA (L-azidohomoalanine) (Invitrogen) was added and cultures were incubated for 3 h. Cells were lysed with 1% SDS in 50 mM Tris-HCl with protease and phosphatase inhibitors: 1 mM phenyl-methylsulfonamide, 20 mg/ml aprotinin, and 4 mg/ml leupeptin. Extracts were sonicated and protein concentration was determined by Bradford assay. Protein samples were labeled with biotin alkyne (PEG4 carboxamide-propargyl biotin) (Invitrogen) using the Click-iT® Protein Reaction Buffer Kit (Invitrogen) according to manufacturer's instructions. Equal concentrations of protein were run on a 10% SDS-PAGE and transferred to nitrocellulose membrane, incubated with streptavidin-HRP reagent (Pierce Thermo Scientific, Rockford, Ill.) followed by reaction with ECL reagent (Pierce) and exposed on film.

Expression and Purification of Human Aminoacyl tRNA Synthetases—

Figure 5A:
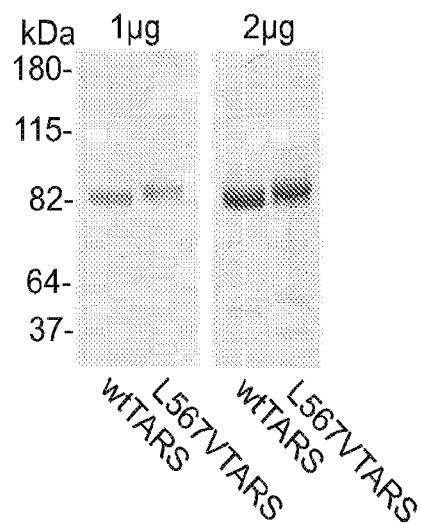
FIG. 5A-B provides a blot and graphs indicating expression and activity of human TARS and L567V TARS. Proteins were expressed and purified from *E. coli* Rosetta™ cells as described in Examples section.
Figure 5B:
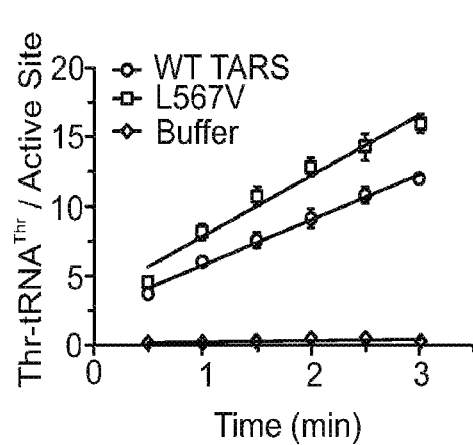
Figure 6A:
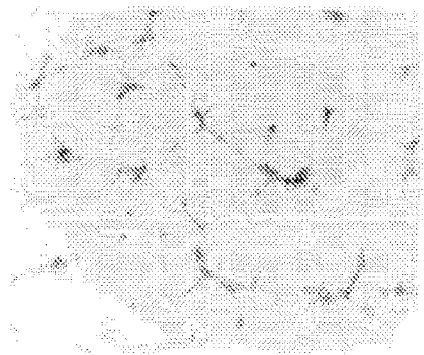
FIG. 6A-F provides photomicrographic images and a graph providing evidence that exogenous application of TARS promotes angiogenesis by an in vitro endothelial tube formation assay.
Figure 6B:
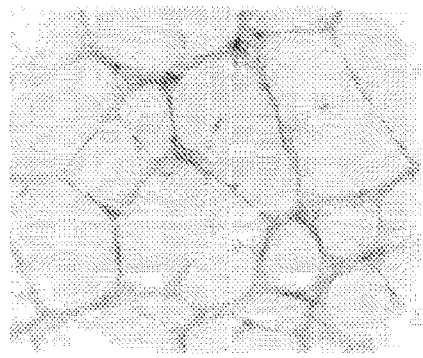
Figure 6C:
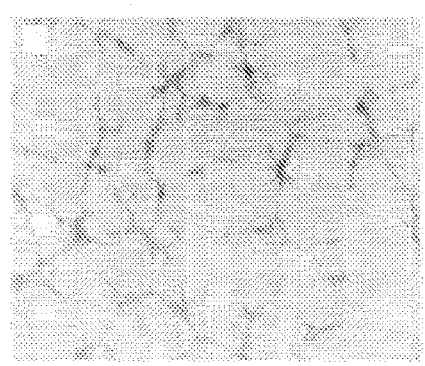
Figure 6D:
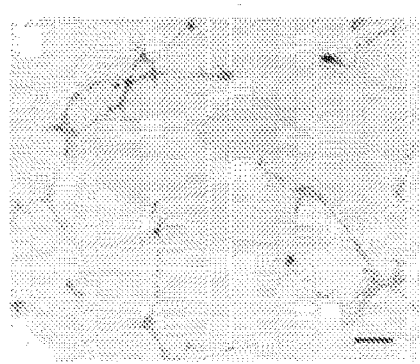
Figure 6E:
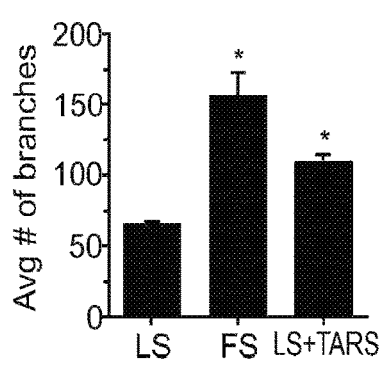
Figure 6F:
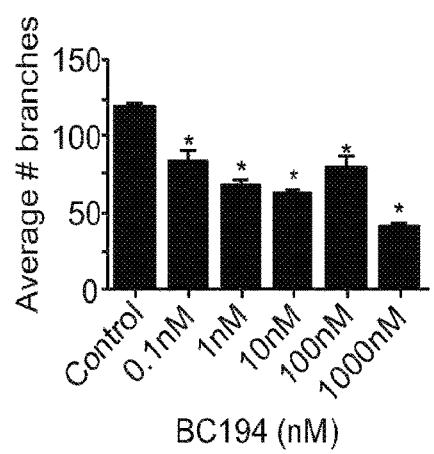

N-terminal $His_6$-tagged human TARS (ThRS) was expressed and purified from E. coli Rossetta™ 2(DE3) pLysS competent cells (EMD Millipore, Billerica, Mass.) transformed with derivatives of plasmid pET28a hctThrRS. Transformant cultures were grown in terrific broth supplemented with 100 mg/ml kanamycin and 100 mg/ml chloramphenicol at 37° C. to a cell density of A600=0.6. Expression of TARS was induced with 1 mM isopropyl 1-thio-β-D-galactoside overnight at 15° C. The bacterial pellet was lysed by sonication in buffer A (20 mM potassium phosphate buffer pH 8.0, 100 mM KCl, 35 mM imidazole, and 5 mM β-mercaptoethanol) and cleared by centrifugation at 17050×g for 30 minutes. Nucleic acids were precipitated by the addition of protamine sulfate to a final concentration of 0.3% followed be centrifugation. The supernatant was loaded onto a HisTrap™ FF column (GE Healthcare, Pittsburgh, Pa.) in buffer A and eluted by an imidazole gradient of 35-250 mM in buffer A over 20 column volumes. TARS containing fractions were identified by SDS-PAGE and GelCode™ Blue (Thermo Scientific, Rockford, Ill.), pooled, and dialyzed into buffer B (100 mM potassium phosphate buffer pH 6.8 and 5 mM (3-mercaptoethanol). The sample was loaded onto a CHT-Tricom Hydroxyapatite column and eluted over 20 column volumes by using a gradient of buffer B to buffer C (500 mM potassium phosphate pH 8.0 and 5 mM β-mercaptoethanol). TARS-containing fractions were determined by SDS-PAGE. Buffer B (10 mM HEPES pH 8.0, 100 mM KCl, 2.5 mM 3-mercaptoethanol, and 40% glycerol), and stored at −20° C. TARS-containing fractions were pooled and dialyzed into buffer D (10 mM HEPES pH 8.0, 100 mM KCl, 2.5 mM β-mercaptoethanol, and 40% glycerol), and stored at −20° C. Protein concentration was determined by Abs260. The protein purity and stability were evaluated by Coomassie stain following SDS-PAGE, and concentration of active sites was determined using a steady state aminoacylation assay (FIG. 5).

The L567V mutant was derived from the wildtype TARS plasmid using Quikchange II Site-Directed Mutagenesis (Stratagene, Cedar Creek, Tex. [Agilent Technologies Inc., Santa Clara, Calif.]) with the forward primer 5' cac cag tgt gca acc atc cag ctg gat ttc cag gtg ccc atc aga ttt aat c 3' (SEQ ID NO:8) and its reverse compliment [5'-gat taa atc tga tgg gcc act gga aat cca get gga tgg ttg cac act ggt g-3' (SEQ ID NO:9)] and transformed into XL1-Blue cells. Colonies positive for the mutation were isolated, grown in LB media, and the plasmid purified via Qiagen miniprep kit. The plasmid was then transformed into Rosetta II cells for use in protein expression using the same protocol as for wildtype TARS.

Figures 9A, 9B:
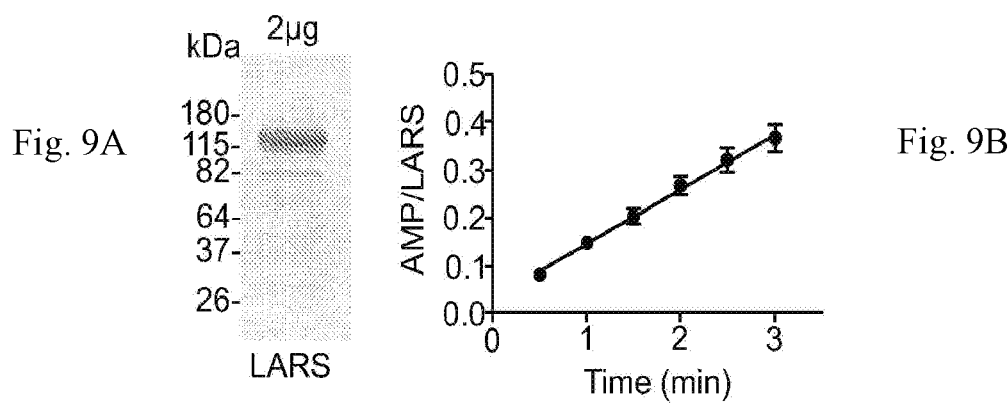
FIG. 9A-D provides a blot, graph, photomicrographic image, and a histogram showing the purification, activity, and lack of CAM effects of Leucyl tRNA synthetase (LARS). Human LARS was purified from E. coli as described in Materials and Methods in Examples section
Figure 9C:
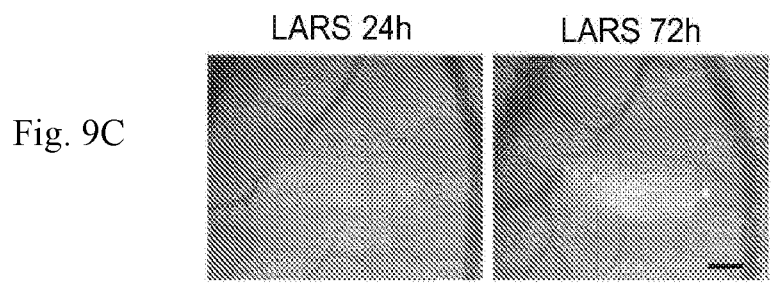
Figure 9D:
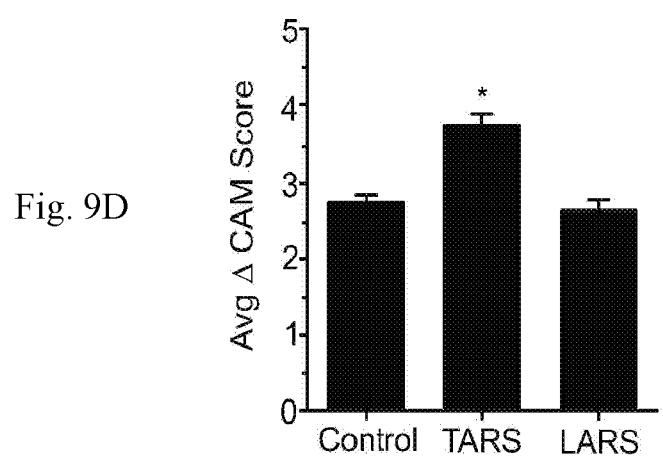

N-terminal $His_6$-tagged human leucyl tRNA synthetase (LARS) was expressed using the plasmid pPROEX hTb-LARS and purified using a similar purification scheme to the TARS purification with minor modifications described in (Francklyn, First et al., 2008). The protein purity and stability were confirmed using SDS-PAGE and Coomassie stain (FIG. 9).

Steady State Aminoacylation Assay—

The aminoacylation activities of the TARS constructs were determined using modifications to established procedures (Francklyn et al 2008). Briefly, reaction mixtures consisted of 20 mM Tris-HCl pH 8.0, 100 mM KCl, 10 mM $MgCl_2$, 1 mM dithiothreitol, 2 mM ATP, 2.5 U pyrophosphatase (Roche), 80 µM threonine, 20 µM [$^{14}$C]-threonine, and 5 µM of E. coli or human tRNAThr. Reactions were initiated with the addition of 0.25-0.75 µM TARS and run at 37° C. Aliquots were taken at varying time points and spotted onto Whatmann 3MM paper filters pre-soaked in 5% trichloroacetic acid (TCA). Upon completion, the filters were washed 3 times in excess TCA, once in 95% ethanol, and dried under a heating lamp. The formation of Thr-tRNAThr was detected by scintillation counter and the activity determined by linear regression of threonyl-tRNA-Thr formed per active site per unit time.

LARS steady state ATPase activity was determined using the same procedure as for TARS aminoacylation with the following modifications. The reaction mixture did not include labeled threonine or tRNAThr and 1 nM [α-32P] ATP (PerkinElmer, Waltham, Mass.) was added. Reactions were incubated for 3 minutes at 37° C. and initiated with the addition of 1 µM human LARS. At various time points 5 µl aliquots were quenched in 45 µl of 500 mM sodium acetate and 0.1% sodium dodecyl sulfate. For each sample, 1 µl was spotted onto a CCM cellulose PEI F plates (EMD) and resolved via thin-layer chromatography in 0.75 M potassium phosphate buffer mobile phase. Radioactive signals were detected via phosphorimaging and AMP production overtime was quantified using Quantity One v 4.6.6 software (Bio-Rad, Hercules, Calif.).

Chick Chorioallantoic Membrane Assay—

Fertilized chicken eggs (Sunrise Farms, Catskill, N.Y.) day 1-2 post-laying were incubated in a humidified incubator at 37° C. for 72 h. Cleaned eggs were cracked and plated in a sterile 10 cm² tissue culture-treated dish and incubated at 37° C. for another 7 days. On developmental day 10, 1 mm³ sterile gelatin sponge pieces (Surgifoam®; Johnson & Johnson Wound Management, Somerville, N.J.) were placed within the outer one-third of the membrane between large vessels. 40 µg/ml human bFGF and 2 µg/ml human VEGF were used as pro-angiogenic control compounds; 100 g/mL retinoic acid (Sigma-Aldrich, St. Louis, Mo.) diluted in phosphate-buffered saline (PBS) was used as an angiostatic control. All compounds were applied in 10 µl to the CAM every 24 h for 72 h. Images were taken using a Leica MZ6 stereomicroscope every 24 h. Compounds were scored according to a modified version of Intensity Scoring as previously described (Ribatti, Nico et al. 2006). Briefly, each experimental condition was given a blinded score from 0-5 based on the change in the extent of vessel convergence and formation in proximity to the sponge from day 0 to day 3. Total score is averaged individual experimental condition scores from at least 15 replicates.

ELISA and Lactate Dehydrogenase Assays—

Confluent HUVEC cultures (passage 4) were incubated at 37° C. in Clonetics® EGM®-2 modified with 0.2% fetal bovine serum with the addition of 50 ng/ml human VEGF or 50 ng/ml human TNF-α for 6 h as indicated. Culture media supernatants were tested for levels of secreted TARS protein using the Threonyl tRNA Synthetase (TARS) ELISA Kit (USCN Life Science, Wuhan, Hubei, PRC) according to manufacturer's instructions. Cell membrane integrity was confirmed using the lactate dehydrogenase assay CytoTox-ONE™ Homogeneous Membrane Integrity Assay (Promega, Madison, Wis.) according to manufacturer's instructions and reported as percent cytotoxicity relative to a lysis control. Levels of secreted VEGF were measured using the Human VEGF ELISA kit (Thermo Scientific) per manufacturer's instructions.

Quantitative RT-PCR—

Total RNA was extracted from cells using the RNeasy column protocol and cDNA was generated using an Omniscript reverse transcriptase assay according to the manufacturer's instructions (Qiagen, Frederick, Md.). Primers and probes for TARS and 32-microglobulin were Assays-on-Demand (Applied Biosystems, [Life Technologies, Carlsbad, Calif.]). RT-qPCR was performed using an ABI prism 7700 Sequence Detection System (Applied Biosystems). The relative quantity of mRNA level was determined using the comparative CT (AACT) method using β2-microglobulin to normalize mRNA level (Cassavaugh, Hale et al. 2011).

Endothelial Cell Proliferation Assay—

The MTT-based alamarBlue® (Invitrogen) reagent was used to assess cell proliferation (Ahmed, Gogal et al. 1994). HUVECs were seeded in a 96-well dish ($1\times10^3$ cells/well) and grown for 48 h in EGM®-2 media. Cells were incubated in 0.2% FBS EGM®-2 media or EGM®-2 complete media as indicated; VEGF (50 ng/ml) and media alone served as controls. After 48 h, 72 h, or 96 h in culture, 10 µl/well premixed alamarBlue® (Invitrogen) was added and after 3 h at 37° C. the amount of reduced alamarBlue® was quantified by fluorescence (excitation at 530 nm, emission at 590 nm) on a microplate reader (Synergy™ HT, BioTek, Winooski, Vt.).

Transwell Migration Assay—

Migration was assessed using transwell inserts (Svensson, Kucharzewska et al. 2011). HUVEC cultures were serum-depleted overnight in Clonetics® EGM®-2 modified with 0.2% fetal bovine serum then $5\times10^4$ cells were plated in 90% EBM®-2, 10% EGM®-2 in the upper chamber of 0.2% gelatin-coated 24-well 8 m Transwell® inserts (Corning, Tewksbury, Mass.) with 90% EBM®-2, 10% EGM®-2 media plus 50 ng/ml VEGF, 1-100 nM TARS protein, or 10 nM BC194 in the lower chamber. Cultures were incubated for 4 h, fixed in 10% formalin, and stained with 10 µg/ml DAPI solution (Roche) following removal of cells from the top layer of the chamber with a cotton swab. Migrated cells were imaged using a 4× objective on the Olympus IX70 Inverted microscope (Olympus). DAPI-stained nuclei were counted using ImageJ software.

Statistical Analysis—

Data are presented as mean+SEM, and $p<0.05$ is considered significant. Except where indicated, one-way ANOVA for multiple comparisons was performed on all data. A Kruskal-Wallis adjustment was used where necessary. All pairwise comparisons were assessed using the Student's t-test.

Results for Example 1

Concentration-Dependent Effects of a TARS Inhibitor Reveal a Specific Angiogenic Function for TARS.

Figure 2:
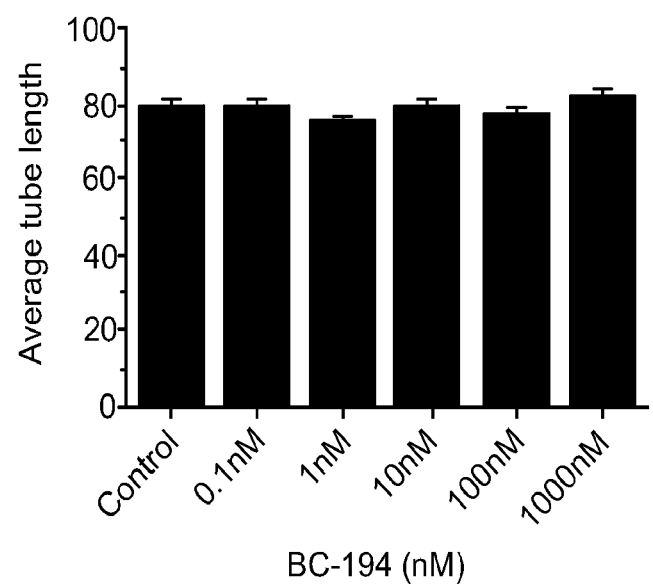
FIG. 2 is a graph showing that BC194 does not affect endothelial tube branch length. HUVECS were treated with the indicated concentration of the TARS inhibitor BC194. Graph shows quantification of branch length in pixels over a range of BC194 concentrations using the Simple Neurite Tracer plug-in on ImageJ software. Multiple comparisons of one-way ANOVA were performed using the Tukey Test; n=3.
Figure 4A:
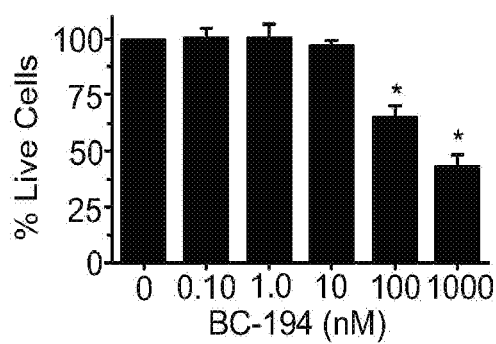
FIG. 4A-D provides graphs and an SDS-PAGE illustrating a lack of effect of BC194 on cell viability and protein synthesis.
Figure 4B:
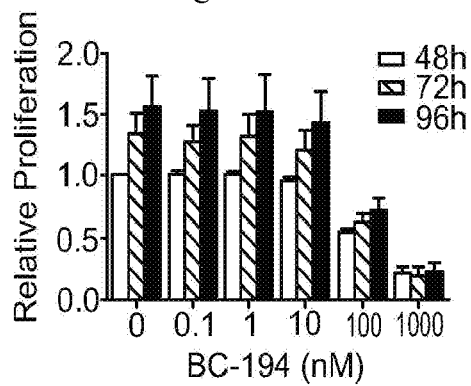
Figure 4C:
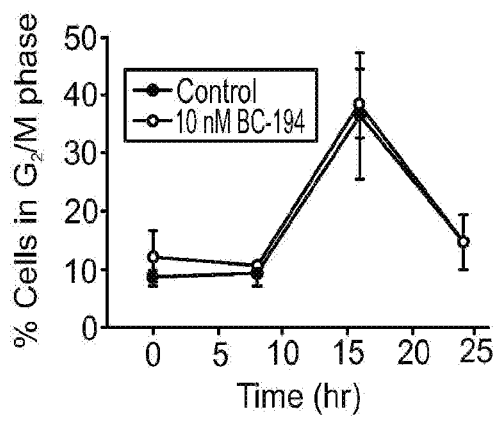
Figure 4D:
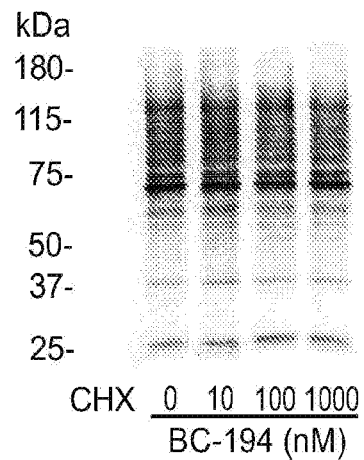

Inhibition of TARS by BC194 has been shown previously to reduce in vitro endothelial tube formation (Wilkinson, Gregory et al. 2006); however, because TARS is a component of the protein synthesis machinery, this effect could be explained by cell toxicity through the unfolded protein response or apoptosis pathways. By using a range of BC194 concentrations, the sensitivity of HUVECs to the anti-angiogenic versus cell stress effects of BC194 was compared. As shown in FIG. 1, the number of branches formed by endothelial cells in a tube formation assay was sensitive to subnanomolar concentrations of BC194, although tube length was unaffected (FIG. 2). The concentration of BC194 required to affect tube formation was 100-fold lower than that required to detect the unfolded protein response (phospho-eIF2α) and apoptosis (cleaved caspase-3) (FIG. 3). Effects on cell viability, proliferation, and nascent protein synthesis were also unaffected by BC194 at concentrations below 100 nM (FIG. 4). These data suggest that TARS may serve a secondary function in angiogenesis signaling that is separate from its function in protein synthesis and is highly sensitive to inhibition by BC194. (FIG. 8 provides photomicrographic images representative for the data shown in FIG. 4).

Exogenously Added TARS Stimulates Angiogenesis.

In light of the potential role for TARS in angiogenic signaling and the secreted activity of select other aminoacyl tRNA synthetases (Wakasugi and Schimmel 1999; Greenberg, King et al. 2008), the ability of purified TARS to stimulate angiogenesis was tested using the in vitro tube formation assay. Human His-tagged TARS was expressed in *E. coli* and purified by nickel chromatography followed by sequential column chromatography to produce an active and pure preparation (FIG. 5). As shown in FIG. 6, addition of TARS to low-serum media significantly increased the number of tube branches, suggesting that TARS itself is angiogenic and implicating an extracellular effect for BC194's anti-angiogenic effect on endothelial cells.

Figure 7A:
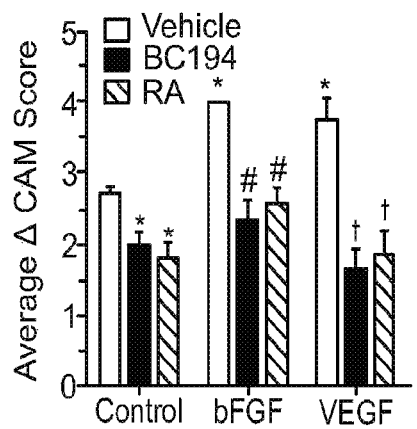
Figure 7B:
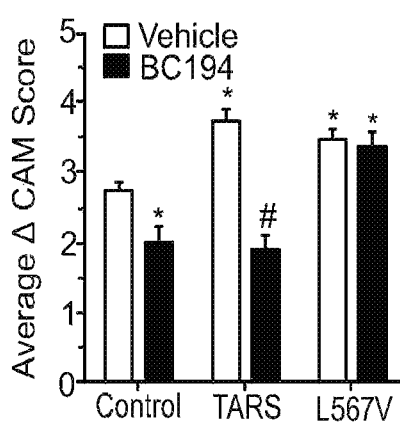

To confirm and expand these results, a chorioallantoic membrane (CAM) assay was used to examine a role for TARS in an in vivo angiogenesis environment. Daily application of BC194 to a gel sponge on the CAM over 4 days inhibited vessel formation at both the basal level and after stimulation with either bFGF or VEGF (FIG. 7A). Application of TARS to the CAM stimulated vessel formation and the angiogenic effect was sensitive to BC194, suggesting that the inhibition of angiogenesis by BC194 is not due to off-target effects (FIG. 7B,C). This conclusion was further supported by the finding that a BC194-resistant mutant of TARS, L567V TARS, stimulated vessel formation that was not inhibited by application of BC194 (FIG. 7C). Application of Leucyl tRNA synthetase (LARS) to the CAM had no observable effect on vascularization, suggesting that the angiogenic effect is not a property of all tRNA synthetases (FIG. 9). Together these data support a specific role for extracellular TARS in the activation of the in vivo endothelial angiogenic response.

TARS is Secreted in Response to VEGF and TNF-α.

Figure 10A:
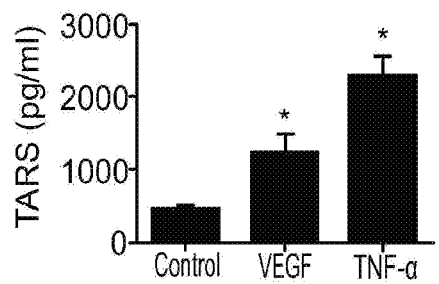
FIG. 10A-D provides graphs and a Western blot demonstrating that TARS is secreted by endothelial cells in response to VEGF and TNF-α.
Figure 10B:
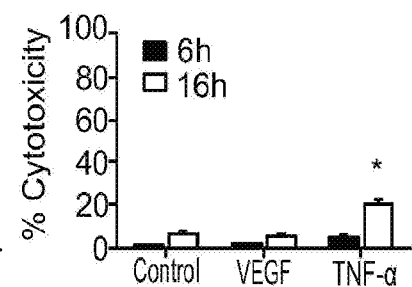
Figure 10C:
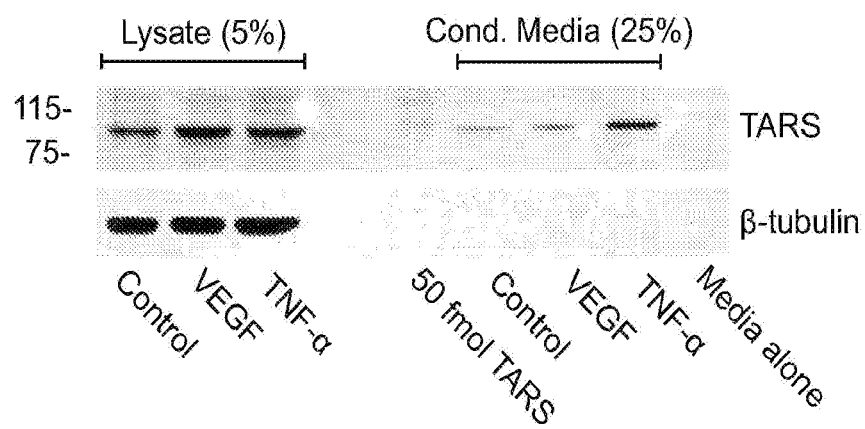
Figure 10D:
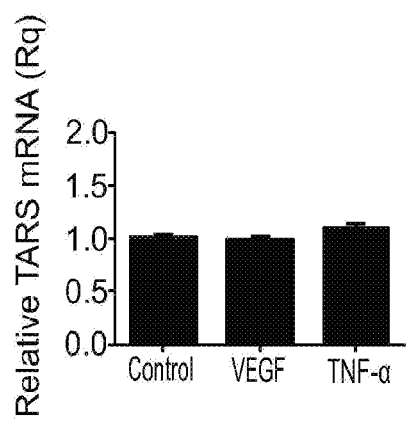
Figure 10E:
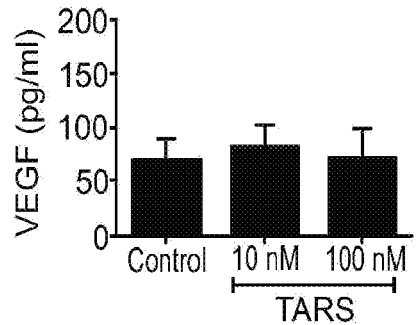
FIG. 10E shows that TARS does not induce VEGF secretion. HUVECs were exposed to the indicated concentrations of purified recombinant human TARS for 24 h and the level of VEGF in the supernatant determined by ELISA; n=3.

Although TARS exerts significant pro-angiogenic effects, there was no prior evidence that TARS is physiologically present in the extracellular space except as a result of cell lysis. To explore the possibility that TARS is actively secreted, endothelial cells were treated with VEGF or TNF-α followed by measurement of TARS in the media using ELISA. As shown in FIG. 10A, both VEGF and TNF-α stimulated a significant increase in TARS in the media, in an excess of 1000 pg/ml. The TARS present in the media was not due to cell lysis as confirmed by a cytotoxicity assay (FIG. 10B). The presence of TARS in the media was also not due to an increase in TARS expression since neither VEGF nor TNF-α induced an increase in TARS mRNA (FIG. 10D). Furthermore, adding purified recombinant TARS to the cell media did not induce secretion of VEGF as measured by ELISA (FIG. 10E). These results support a mechanism whereby TARS secretion is increased following stimulation of endothelial cell signaling through VEGF or TNF-α receptors.

TARS Stimulates Endothelial Cell Migration.

Figure 11A:
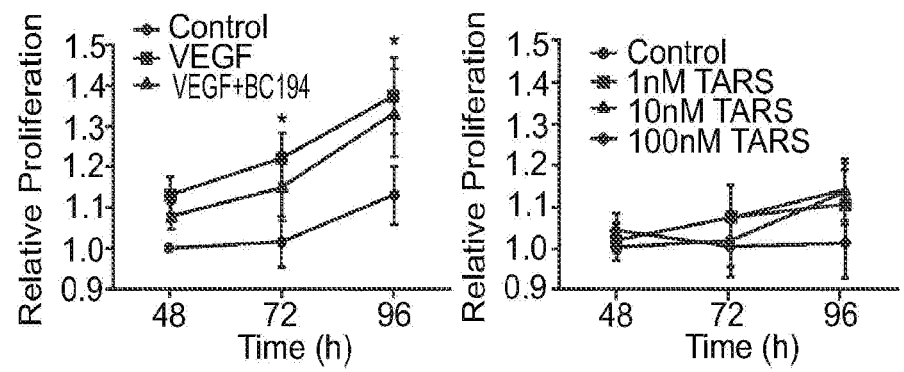
FIG. 11A-C provides graphs, photomicrographic images and a histogram showing that TARS selectively induces migration of endothelial cells that is sensitive to BC194.
Figure 11B:
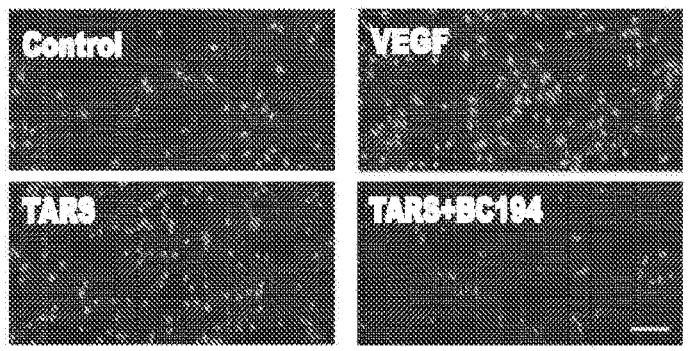
Figure 11C:
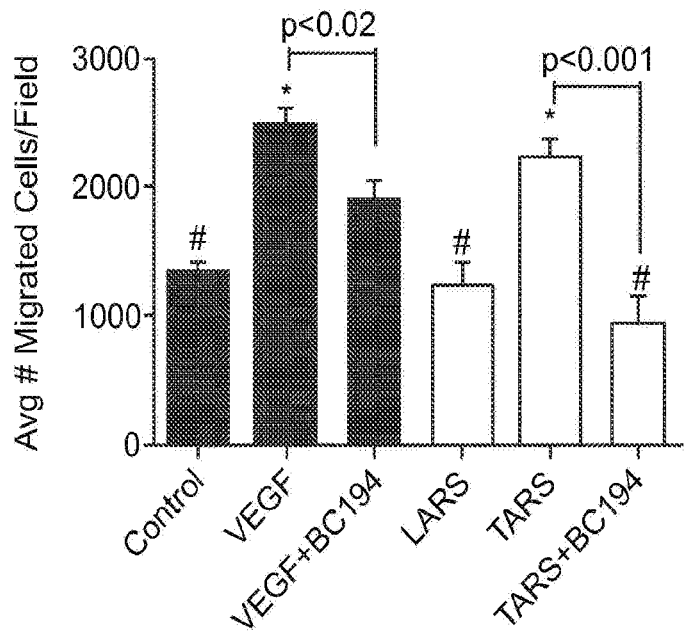

An increase in angiogenesis by TARS signaling to endothelial cells could have resulted through either an increase in cell proliferation or an increase in cell migration. Unlike VEGF, TARS did not exert a significant effect on cell proliferation, and BC194 did not significantly reduce the VEGF proliferative response (FIG. 11A). However, TARS significantly increased migration of endothelial cells in a transwell assay to an extent that was similar to VEGF (FIG. 11B). LARS did not affect migration, indicating that the TARS-mediated effect was not a non-selective result of synthetase activity. Importantly, BC194 reduced both the migration effects of VEGF and TARS, although the VEGF effect was less pronounced, suggesting that TARS may play a significant role in VEGF-mediated endothelial cell migration. This evidence supports a mechanism for TARS that includes stimulation of endothelial cell migration that contributes to its angiogenic effect.

Figure 12:
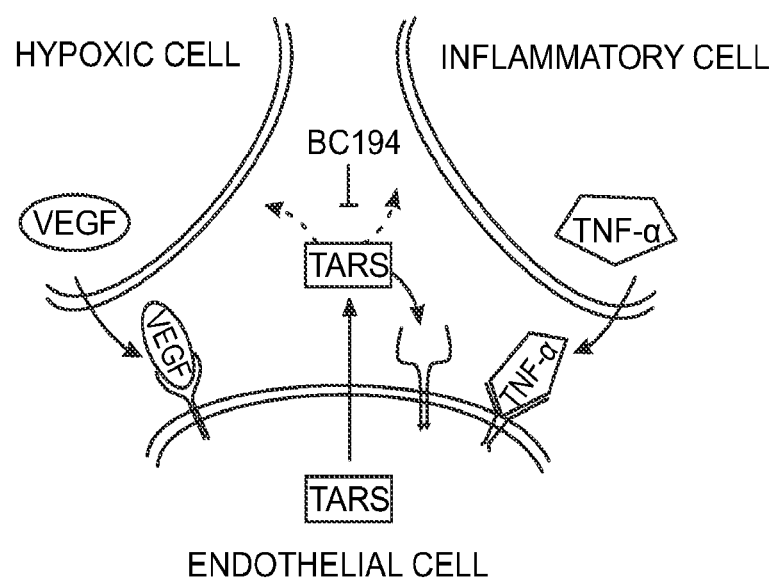
FIG. 12 is a schematic diagram of a proposed model for TARS signaling and angiogenic activity. VEGF and TNF-αt secretion by hypoxic and cells of the tumor microenvironment leads to VEGF receptor activation on endothelial cells and secretion of TARS. Secreted TARS has autocrine and possibly paracrine functions that promote angiogenic signaling. BC194 binds and inactivates TARS, preventing its angiogenic function. Thus, TARS present in patient serum could be an indicator of the angiogenic potential of tumors.

TARS may be playing a substantial role in normal and pathogenic angiogenesis as a proangiogenic chemokine activated by endothelial cells in response to VEGF or TNF-α stimulation (FIG. 12). With this as the first report of the novel angiogenic function of TARS, much remains to be uncovered about how TARS signals to endothelial cells, other processes beyond migration and angiogenesis secreted TARS may be affecting, and linkages between TARS and tumorigenesis.

Example 2

Database Assessment of TARS in Disease

Database analysis was used to assess TARS expression in cancers including Cancer Gene Anatomy Project (CGAP) (Strausberg 2001), GEO database, and Human Protein Atlas (Uhlen, Oksvold et al.). Using the CGAP database, TARS mRNA was found to be over-expressed in cells derived from prostate carcinoma, colon adenocarcinoma, ovarian carcinoma, and in certain stem cell lines. Furthermore, whereas other synthetases were found to be relatively unchanged, TARS protein was found to be selectively upregulated in ovarian tumors from tissue arrays displayed in the Human Protein Atlas. (www.proteinatlas.org/ENSG00000113407).

A preliminary investigation using GEO data from a prostate cancer progression study by Tomlins et al. (Tomlins, Mehra et al. 2007) revealed that mRNA levels of TARS exhibited a 2.9 fold increase in prostate carcinoma versus normal ($p<0.0001$). To expand on these findings, GEO dataset GSE6919, 171 sample CEL files (scanned chip image files) were downloaded. GSE6919 is a GEO SuperSeries that includes GSE6604 (normal prostate tissue from 18 patients), GSE6605 (metastatic prostate tumor included 25 samples from 4 patients and 9 sites, some paired), and paired sets GSE6606 (primary prostate tumor from 65 patients), and GSE6608 (normal prostate tissue adjacent to tumor from 63 of those patients). Probe-level intensities were background-corrected, normalized, and summarized, and Robust Multichip Average (RMA) statistics are calculated for each probe set and sample as is implemented in Partek Genomic Suites, version 6.6 Beta (Copyright 2009, Partek Inc., St. Louis, Mo., USA). Sample quality was assessed based on the 3':5' ratio, relative log expression (RLE), and normalized unscaled standard error (NUSE). Principal Component Analysis (PCA) was also used to look for outlier samples that would potentially introduce latent variation into the analysis of differential expression across sample groups. Based on these analyses, 13 samples were eliminated from further analysis. Additional analysis included assessment of GEO datasets. Results of the analysis, which included a comparison of samples of normal and metastatic prostate cancer tumors, indicated that TARS mRNA was found to be significantly elevated. These findings were selective for TARS in that other aminoacyl tRNA synthetases were not elevated in prostate cancer.

Example 3

Analysis of TARS Expression in Prostate Cancer Patients
Patient Selection for IHC Studies—

Using an IRB protocol (CHRMS #:08-218) approved by UVM Committee on Human Subjects, FAHC patient registries were searched to identify patients with high grade PCa from 2008-2010 for whom archived tissue samples were available. The search was confined to those patients for whom a clinical record was available, and who had all undergone prostatectomies, and for whom there were clinical samples available. An initial set of 54 cases with PC surgeries from 10/08 to 3/10 was collected in this way. A second group of 79 patients with high-grade disease was identified with surgeries over the interval 12/99-8/02.
Immunohistochemistry—

The immunohistochemistry procedures were conducted essentially as described (Conant, Penz, et al., 2011). Slide mounted 5 μm tissue sections cut from formalin-fixed, paraffin-embedded (FFPE) prostate carcinoma specimens were dewaxed by 3×5 mins washes in xylene followed by rehydration through graded ethanol washes (100%, 95%, 70% and 50%; 2×3 mins in each). After rinses in Milli-Q ultra-pure water (EMD Millipore, Billerica, Mass.), heat induced epitope retrieval (HIER) was performed by immersing the slides in Target Retrieval solution pH 6.0 (Dako North America Inc., Carpenteria, Calif.) and heating at 100° C. for 15 mins in a Decloaking Chamber™ Pro pressure cooker (Biocare Medical, Concord, Calif.). Slides were then allowed to cool in the pressure cooker unit for another 20 minutes. After 3×5 minute rinses in TBST (25 mM Tris, 0.15M NaCl, 0.05% Tween 20), slides were immersed in 3% $H_2O_2$/TBST for 15 mins as to inactivate any endogenous peroxidase in the tissues. After 3×5 min washes in TBST slides were immersed in protein block, serum-free ((Dako North America Inc., Carpenteria, Calif.) for 15 minutes to block non-specific protein binding sites in the tissues. Primary antibody (anti-TARS, mouse monoclonal clone 1A9, Abnova, Walnut, Calif.) at a 1:200 dilution was then applied for 30 min at room temperature. As a negative control test, IHC was also performed substituting primary antibody with a mouse monoclonal (mAb) IgG1 antibody to *Aspergillus niger* glucose oxidase (Dako North America Inc., Carpenteria, Calif.). After TBST washes, secondary detection was performed by incubating the slides for 30 mins RT with EnVison+ Dual Link polymer HRP (horseradish peroxidase) reagent (Dako North America Inc., Carpenteria, Calif.). Following a further series of TBTS washes, slides were incubated for ~6 minutes with DAB+chromogen substrate (Dako North America Inc., Carpenteria, Calif.) and then rinsed with tap water. Tissues were then counterstained with hematoxylin for ~7 minutes, rinsed with TBST and water and the dehydrated through 50%, 70%, 95% and 100% ethanol. Finally, slides were cover-slipped with Cytoseal mountant (ThermoFisher Scientific, Waltham, Mass.) for viewing by bright-field microscopy.
Imaging Details—

Images of IHC were captured at the Micrscopy Imaging Center at the UVM College of Medicine using an Olympus BX50 light microscope, QImaging Retiga 2000R camera, and QCapture Pro Software. The final images used for standards in grading are seen in FIG. 13A.
Immunohistochemistry Scoring—

The stained slides were initially scored by a primary pathologist, and then a secondary review was provided two other expert pathologists. In the scoring procedure, the pathological grade and the intensity of TARS immunochemical staining were evaluated independently. In the pathological grading, each slide was evaluated by assigning different region of the slide to benign (non-tumor) and tumor. The total tumor area was further subdivided into Gleason primary pattern 3, 4, or 5, and a % of tumor region estimated for each. (There are no Gleason scores below 2, because such patients were never subjected to prostatectomies.) The AJCC criteria were used to make these pathological assessments. The pathological assessment also included the recording and grading of HGPIN (a precursor lesion to PCa) and several benign controls, including BPH and atrophy (characterized by small, hyperchromatic nuclei with no prominent nucleoli). The experimental analysis noted tissue staining pattern (diffuse, focal, or scattered), and any additional notes (such as tertiary Gleason grade, lymph node metastasis, or extraprostatic extension (EPE). In cases where there were uncertainties and/or ambiguities, the original H&E stained slides corresponding to each case were referenced. The TARS IHC staining intensity was graded independently, using a semiqualitative scale from 0-3 (0=negative, 1=mild, 2=moderate, and 3=strong). A set of reference slides that served to calibrate the scoring procedure is shown in FIG. 13A. The regions of each slide corresponding to the various Gleason scores were each independently scored for TARS, as was the "benign" region.
Statistical Analysis.

Univariate statistics were used to determine the significance between TARS staining and tumor type. Secondary t-tests were done to correlate TARS intensity with progression from Gleason 3 to 4 and to correlate TARS intensity with PSA and biochemical failure.
ELISA Assays.

TARS ELISA was perform on neat serum samples, according the manufacturer's (CUSABIO Biotech, Wuhan, P.R. China) instructions. The serum samples from four age matched male non-cancer subjects was used as the control group.

Results for Example 3

Immunohistochemical Analysis of TARS Expression in Prostatectomy Sections.

To assess the relationship between TARS expression and prostate cancer progression, patient tumor samples were analyzed by immunohistochemistry and scored by intensity as shown in FIG. 13A. Statistical analysis of the data concluded that TARS protein levels are increased in tumors with Gleason score of 3 and above (FIG. 13B). In addition, a post-analysis of the TARS intensity found a significant increase in expression during progression from Gleason score 3-4 with a mean difference of 0.304, and a p-value of 0.0001.

TARS expression was also compared with 10-year outcome. When TARS staining of the various anatomical grades was examined, there was a strong relationship between Gleason 5 staining and elevated PSA at 10-years. Specifically, a one unit increase in TARS staining on the Gleason 5 portion of the slide increases the odds by a factor of 2.211 that subject will experience biochemical failure. Taken together these results suggest that TARS expression correlates with diagnosis of prostate cancer, progression of disease and likelihood of biochemical failure.

Analysis of Circulating TARS Levels in Prostate Cancer Patients.

The essential features of a useful human biomarker are that it be present in medium that can be readily obtainable in a non-invasive fashion (e.g. serum or urine), that it be readily quantifiable using a robust and repeatable assay, and that it provide useful information that reflects on subject disease state. As part of the very initial process of TARS biomarker discovery, serum samples were collected from 10 consenting subjects of the Fletcher Allan Urology Clinic. This small set included patients at various points along the prostate cancer diagnosis/treatment continuum, including immediately after diagnosis prior to treatment; under active surveillance; and under androgen deprivation therapy following prior radiation or prostatectomy surgery. Serum samples from four age and gender matched control subjects were also analyzed. All samples were measured in duplicate, and the values reported in FIG. 13C are mean values.

The mean value of the control samples was 105±19.5 pg/mL. Two patients (TARS 0012 and TARS 0013) had values higher than the controls, and the other eight patients all exhibited values lower than the controls. In three cases (TARS 0014, TARS 0016, and TARS0018) the levels of circulating TARS were undetectable, and significantly decreased levels were seen in three others (TARS0011, TARS0014, and TARS 0017). In three of the six cases where TARS levels were significantly decreased or not detectable, the patients were on androgen deprivation therapy. In one patient under androgen deprivation therapy, TARS levels were increased 50% relative to the controls. Notably, the two patients with TARS levels closest to the controls had either received no treatment or were under active surveillance. These data allow several important conclusions regarding the potential utility of TARS as a prostate cancer biomarker to be drawn. First, the TARS enzyme can be readily detectable in human serum samples by a conventional and commercially ELISA kit without any extensive modification or adaptation. Secondly, the variation in levels among different subjects is within the dynamic detection range of the kit. Thirdly, the values seen in untreated or active surveillance patients were closer to the values seen in the controls than samples derived from patients who had undergone past surgery/radiation treatments and were currently under androgen deprivation therapy. This provides initial support for the hypothesis that circulating TARS levels change in prostate cancer patients in response to treatment. It is noteworthy that the significant drop in TARS levels seen with patients under androgen deprivation suggests that TARS expression is at least partially under the control by the androgen receptor.

Example 4

TARS Interacts with VHL and its Inhibition Interferes with the Ovarian Cancer Cell Response to Hypoxia.

Materials and Methods for Example 4

Co-Immunoprecipitation—

Plasmids expressing biotinylatable TARS (pTARS) and myc-tagged VHL (pVHL) were transfected into HEK293 cells, and then extracts were prepared. Biotin-TARS was precipitated using streptavidin-coupled beads. Myc-VHL was precipitated using anti-myc antibodies. Precipitates were separated by SDS-PAGE, transferred and blots probed with anti-TARS antibody or anti-myc (VHL) antibody.

Western Blot—

After treatments, cells were harvested into sample buffer containing: 0.2 M Tris-HCL, 4% SDS, 4% β-mercaptoethanol, 40% glycerol, 4 µM pyronin Y. Extracts were sheared through a 24-gauge syringe. Samples were separated by 10% SDS-PAGE and transferred to nitrocellulose membrane and probed with rabbit polyclonal anti-TARS (1:500; Santa Cruz Biotechnology, Dallas, Tex.) or monoclonal anti-HIF-1α (BD Transduction Laboratories, [BD Biosciences, San Jose, Calif.]) (Lounsbury, Beddow et al., 1994). Secondary antibodies were HRP-goat-anti-mouse and HRP-goat-anti-rabbit (1:5,000; Jackson Laboratories, Bar Harbor, Me.).

Mass Spectrometry.

Culture dishes were seeded with $2 \times 10^6$ human embryonic kidney cells (HEK293) and maintained in DMEM (Mediatech, Manassas, Va.) supplemented with 10% fetal bovine serum (Gibco, Carlsbad, Calif.), penicillin/streptomycin (Gibco), and L-glutamine (Gibco) at 37° C. and 5% $CO_2$ in a humidified incubator. Cells were transfected by polyethylenimine with plasmids encoding a TARS construct with C-terminal HA tag and BirA biotinylation site, BirA, and C-terminally myc-tagged VHL. Control experiments substituted an empty vector plasmid for the TARS construct. Following a 48 hour incubation, cells were lysed with 1% Triton X, 0.5% NP-40, 140 mM NaCl, 25 mM Tris-HCl pH 7.6, and 1 Complete Mini protease inhibitor tablet (Roche) per 10 ml. TARS was then "pulled-down" with streptavidin immobilized on magnetic beads (Invitrogen, Dynabeads MyOne Streptavidin) and unbound proteins were washed away with three exchanges of lysis buffer. The bound proteins were eluted from the beads through boiling and resolved on a reducing, SDS-PAGE gel. Major bands and their empty vector counterparts were detected using Silver-SNAP Stain Kit II (Pierce) and excised. Fragments were typically digested using the in gel procedure for ProteaseMAX Surfactant (Promega, Madison, Wis.) according to the manufacturers specifications. Briefly, free cysteines were alkylated by incubation with 55 mM iodoacetamide:50 mM $NH_4HCO_3$ followed by trypsin digestion (2 ng/µl) in 0.01% ProteaseMAX surfactant:50 mM $NH_4HCO_3$. Peptides were analyzed by electospray ionization (ESI) liquid chromatography mass spectrometry (LC-MS). Samples were resolved over a fused-silica microcapillary MagicC18 LC column (12 cm×100 µm i.d.) using a 5-50% acetonitrile gradient in 0.1% formic acid. Spectra were obtained using collision-induced dissociation with an LTQ linear quadrupole ion trap-Orbitrap mass spectrometer (Thermo Electro, San Jose, Calif.) and analyzed using SEQUEST (Bioworks software package, version 3.3.1; Thermo Electron, San Jose, Calif.). Acquired TARS data were compared to empty vector equivalents in order to identify non-specific interactions.

Results for Example 4

Figure 14:
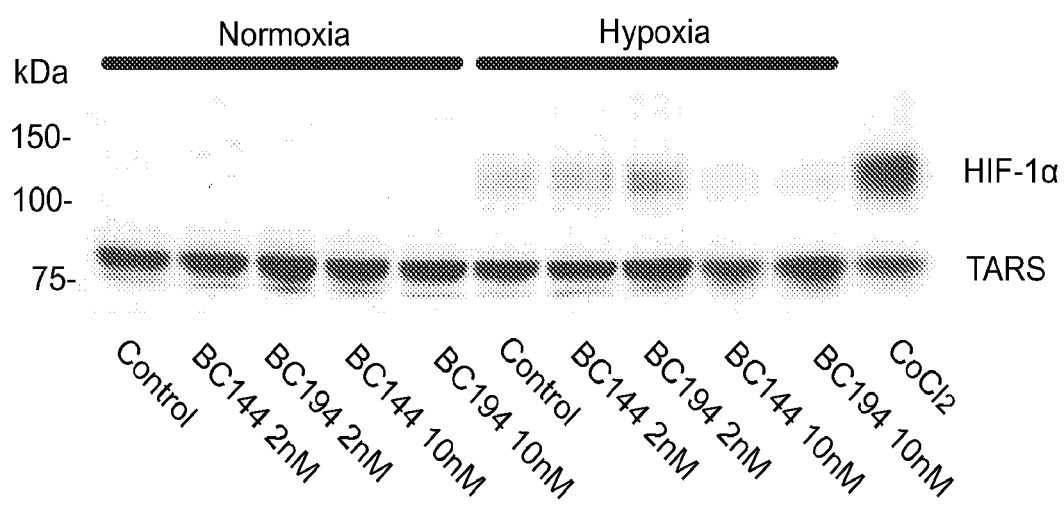
FIG. 14 shows a Western blot demonstrating that TARS inhibitors reduce HIF-1α stabilization in hypoxia. SKOV-3 cells were exposed to hypoxia (2% 02) for 6 h in the presence of the indicated concentrations of the TARS inhibitors: borrelidin (BC144) or BC194. $CoCl_2$ was used as a positive control for HIF-1α stabilization. HIF-1α and TARS proteins were detected by Western blot.

An interaction between TARS and VHL may affect hypoxia signaling. VHL is the E3 ubiquitin ligase for Hypoxia inducible factor-1α (HIF-1α), thus if TARS interferes with VHL activity, it may influence the induction of HIF-1α by hypoxia. Shown in FIG. 14, the TARS inhibitors BC144 and BC194 diminished the levels of HIF-1α protein stabilization in SKOV3 ovarian cancer cells responding to hypoxia. The effect was through stabilization as there was no change in HIF-1α transcription. Accordingly, it was hypothesized that the lowering of HIF-1α levels by BC194 occurs as a consequence of a TARS' interaction with VHL.

Figure 15A:
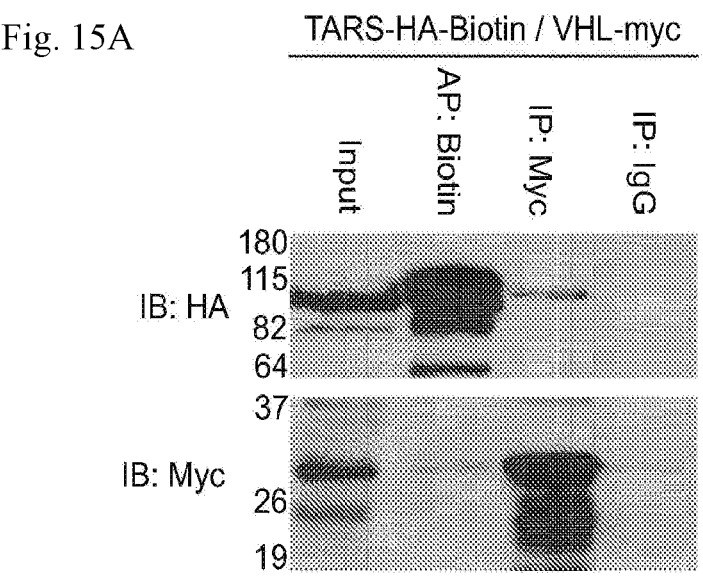
FIG. 15A-B provides evidence for an interaction between TARS and the von Hippel Lindau protein (VHL). Plasmids expressing biotinylatable TARS (TARS-HA-Biotin) and myc-tagged VHL (VHL-myc) were transfected into HEK293 cells, and then extracts were prepared. Biotin-TARS was precipitated using streptavidin-coupled beads. Myc-VHL was precipitated using anti-myc antibodies. Shown in FIG. 15A is an interaction between full-length TARS and VHL by co-immunoprecipitation. Top panels are blots probed with antibody against HA (anti-TARS), bottom panels are blots probed with antibody against myc (VHL) antibody. The various lanes indicate input lysates (Input), streptavidin affinity purified (AP:Biotin), anti-Myc immunoprecipitates (IP:Myc), naïve IgG immunoprecipitates IIP: IgG). Shown in FIG. 15B is the same experiment as FIG. 15A, only the N1 domain of TARS is used in place of the full length enzyme. See FIG. 16 for structural details.
Figure 15B:
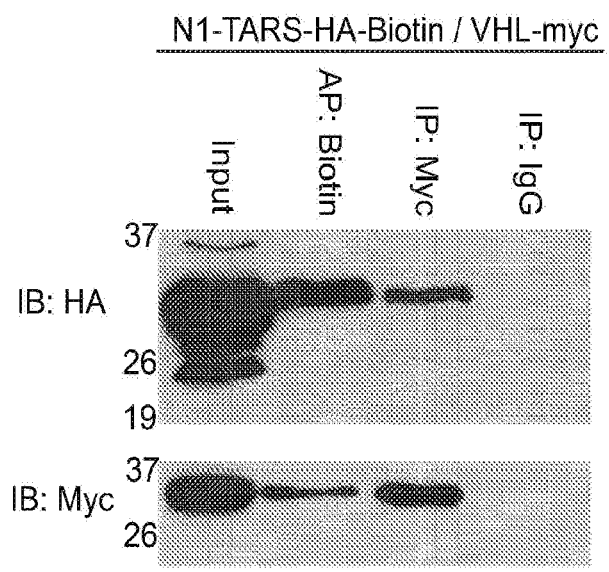

A large-scale study examining protein-protein interactions in human cells featured the immunoprecipitation of flag tagged bait proteins, followed by the LC-ESI/MS analysis of interacting proteins. Using the Von Hippel Lindau tumor suppressor as bait, TARS was identified as a potential binding partner. This result was confirmed in two independent approaches. In the first of these experiments, HEK cells were transfected with expression plasmids for TARS-[hemagglutinin tag]—[biotinylation recognition] and VHL-[myc-tag]. The TARS construct possessed an appended peptide tail that served as recognition site for the *E. coli* biotin ligase, whose gene was also transfected into cells. As shown in FIG. 15A, when biotinylated TARS is precipitated incubation of the extracts with streptavidin beads, the VHL protein is co-precipitated. Conversely, immunoprecipated VHL will also co-precipitate full-length TARS. The region of TARS that interacts with VHL was explored by a comparison of the structure of the VHL-ElonginB-ElonginC complex to TARS. ElonginB which is a component of the complex, can be readily superimposed with the N-terminal domain of TARS (106 residues aligned; 2.71 r.m.s.d.; p value=0.0019). To confirm the significance of this structural relationship, HEK cells were transfected with plasmids expressing the N-terminal domain of TARS –[hemagglutinin tag]-[biotinylation recognition] and VHL-[myc-tag], and then TARS N1 domain was precipitated with streptavidin beads. This analysis showed that the N1 domain precipitated VHL more efficiently than the full length TARS (FIG. 15B). Hence, the N1 domain is likely to be one of the major interaction domains with VHL.

In order to provide additional validation of the proposed VHL-TARS interaction, and perform the converse experiment of the original Ewing et al experiment (Ewing, Chu, et al. 2007), the proteins that associate with TARS in vivo were identified by precipitating biotinylated TARS, resolving all proteins by SDS polyacrylamide gel electrophoresis, and then subjecting isolated bands to mass spectrometry analysis. The resulting TARS binding partners that were identified are shown in FIG. 16. As a control, a parallel lane was run with proteins precipitated from HEK cells transfected with an "empty" plasmid that does not over produce TARS, or any other protein that can be biotinylated. All peptides that were common to both the TARS plus and control were subtracted from the final results. The "TARS plus" experiments were performed in the presence and absence of plasmids expressing VHL. These experiments identified a number of partners for TARS, including VHL, the glutamyl-prolyl tRNA synthetase (EPRS), poly[ADP-ribose] polymerase 1 (PARP), and elongation factor 1 alpha 1 (eEF1A1). Several other proteins were also detected as single peptides.

Example 5

Angiogenesis Related Secondary Functions of Human Threonyl-tRNA Synthetase

Materials and Methods for Example 5

TARS Preparation and Nucleotide Assays.

Figure 17A:
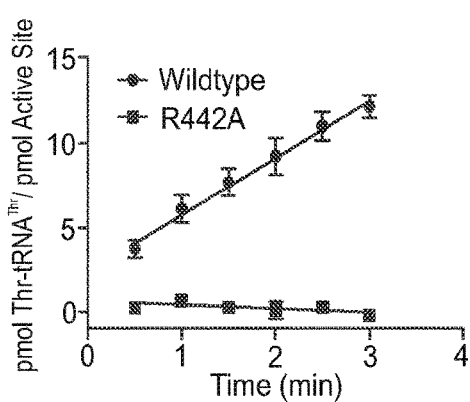
FIG. 17A-F provides graphs and histogram showing that human TARS does not require aminoacylation activity to stimulate angiogenesis activity, and is capable of catalyzing nucleotidase and nucleotide synthesis reactions distinct from aminoacylation. Wild type and R442A mutant TARS were produced as described in Materials and Methods, in Examples section. The R442A mutant substitution exchanges an essential catalytic arginine in the TARS active site for an alanine. The CAM assays were performed as described in Material and Methods in Examples section.
Figure 17B:
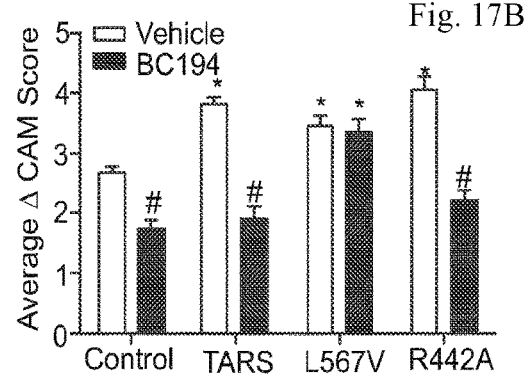
Figure 17C:
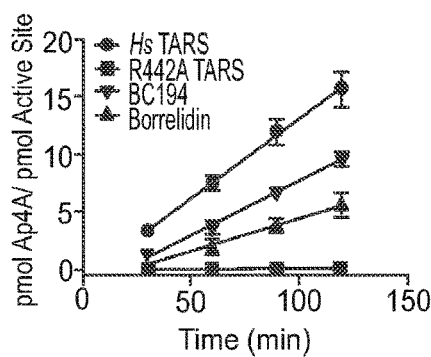

TARS purification and active site determination were performed as previously described (Williams, Mirando et al., 2013). TARS non-canonical catalytic activities were characterized using modifications from published methods (Guo, Chong et al. 2009). For Ap4A reactions 5 µM of wildtype TARS or R442A TARS were incubated for 10 minutes on ice with 2 mM threonine, and 10 µM BC194 or borrelidin as indicated in FIG. 17C. Reactions were initiated using 2 mM ATP with trace amounts of [α-$^{32}$P]-ATP as label. At specific time points aliquots were quenched in 3 volumes of 0.1% SDS, 400 mM sodium acetate and resolved on polyethyleneimine-cellulose plates by thin-layer chromatography (TLC) in 3 M NH$_4$ (SO$_4$)$_2$ and 2% EDTA. Radioactive counts were identified by phosphorimaging and products quantified as fractions of total ATP added. The quantitation of product was normalized to take into account the fact that each Ap4A molecule has two equivalents of radioactive phosphorus.

Figure 17D:
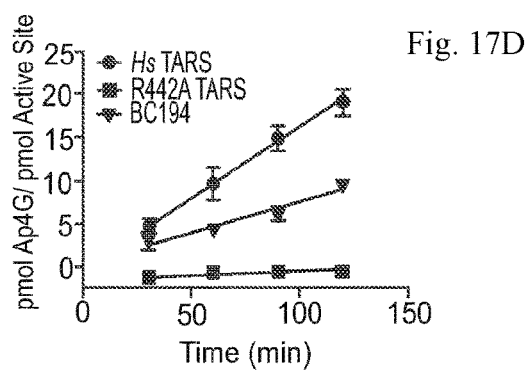

Ap4G and GTPase assays were performed as above with the following exceptions: Ap4G reactions always included 2 mM ATP and 2 mM threonine and 10 µM BC194 where indicated in FIG. 17D. For GTPase assays, ATP and threonine were not present in all reactions but were included in combination with, 10 µM tRNA$^{Thr}$, 10 µM BC194, and 10 µM borrelidin according to FIG. 17F. Adenylation conditions consisted of ATP and threonine and aminoacylation conditions further included tRNA$^{Thr}$. Reactions were initiated using 2 mM GTP with trace amounts of [α-$^{32}$P]-GTP. The components were resolved by TLC using the mobile phases 750 mM KH$_2$PO$_4$, pH 3.5 for GTPase data and 3 M NH$_4$ (SO$_4$)$_2$ and 2% EDTA for Ap4G. Unlike with Ap4A, Ap4G involves only the incorporation of one labeled nucleotide and does not require the 0.5 correction factor.

CAM assays.

Fertilized chicken embryos were cultured ex-ova and, starting at developmental day 10, agents were applied daily to gelfoam sponges on the CAM. Images were recorded daily over 72 h and scored blindly according to a modified version Intensity Scoring as previously described (Ribatti, Nico, 2006). Additional details regarding methods are provided in the Methods and Materials section of Example 1.

Results for Example 5

An important scientific question is the extent to which the pro-angiogenic functions of TARS are directly linked to aminoacylation function. Alternatively, stimulation of angiogenesis might be linked to alternate catalytic functions, employing substrates and products that are distinct from those aminoacylation. To directly test whether aminoacylation is required for stimulation of angiogenesis, a mutant version of hTARS was produced in which an essential arginine in the active site (Arg442) was substituted with alanine. As shown in FIG. 17A, the resulting mutant protein displayed essentially no aminoacylation activity. Next, the chorioallantoic membrane (CAM) assay was used to investigate whether loss of aminoacylation was associated with loss of angiogenesis stimulating activity. As shown in FIG. 17B, R442A TARS demonstrated angiogenesis stimulating abilities that were virtually indistinguishable from wild type. Notably, the uninhibited version of R442A TARS had an average CAM score that was equal to that of wild type, and R442A displayed a similar level of inhibition of angiogenesis stimulus in the presence of BC194. On the basis of these experiments, it was concluded that aminoacylation function is not required for the stimulation of angiogenesis.

In light of the previous observation that aminoacylation activity is not required to stimulate angiogenesis, the possibility that an alternative catalytic function might be involved was explored. One such alternative is the production of diadenosine tetraphosphate (Ap4A), which is produced by human lysyl-tRNA synthetase in immune cells that become activated by antigen. The Ap4A produced by LysRS binds to Hint, liberating the associated microphthalmia transcription factor (MITF) to execute a complicated program of gene expression (Lee, Nechushtan et al, 2004; Ofir-Birin, Fang et al. 2013). This confirms the role of Ap4A as an intracellular signaling molecule. There is also data to suggest that Ap4A can function as an extracellular signaling molecule (McLennan 2000; Delicado, Miras-Portugal et al., 2006). Significantly, Ap4A is released extracellularly from platelets, and is capable interacting with the P2Y and P2X receptors. These interactions have the potential of modulating angiogenesis in endothelial cells (Chang, Yanachkov et al. 2010; Roedersheimer, Nijmeh et al., 2011).

As shown in FIG. 17C, significant production of Ap4A was observed for wildtype TARS (0.1391 Ap4A/active site/min) and $E.\ coli$ ThrRS (0.5612 Ap4A/active site/min; data not shown). In contrast, no appreciable activity was observed for the aminoacylation-deficient, R442A TARS or in absence of threonine, suggesting that the adenylate intermediate is essential for dinucleotide formation. Treatment with BC194 and borrelidin resulted in a 31.0% and 59.4% decrease in activity respectively. This reduction in activity is not unsurprising as previous reports indicate that borrelidin compounds inhibit aminoacylation at the level of adenylate formation (Ruan, Bovee et al., 2005). However, the 10 µM concentration used for both compounds is in great excess of the calculated $K_i$ values (4.1 nM for BC194; see Williams, Mirando et al. 2013) and 4.6 nM for borrelidin, data not shown) suggesting that maximum inhibition still allows for reduced formation of the adenylate intermediate. A possible explanation for this modest drop in activity compared to the nearly complete inhibition of aminoacylation at similar concentrations is that borrelidin compounds block tRNA$^{Thr}$ binding as well; encouraging the small amount of adenylate that does form to be used in the synthesis of dinucleotide compounds. Similar results were observed (FIG. 17D) in studies of Ap4G: rates for wildtype TARS and $E.\ coli$ ThrRS (data not shown) were comparable to Ap4A data (0.1639 and 0.5612 Ap4G/active site/min respectively). The reaction was not catalyzed by R442A TARS and required the presence of both ATP and threonine, suggesting that adenylate formation was still a requirement. Since threonine alone was not sufficient to form a significant dinucleotide product, Gp4G formation is unlikely. Once again, treatment with BC194 reduced the reaction rate by 57%. Given the similarities between the two processes, it is likely that Ap4A and Ap4G formation occurs at the same site in the enzyme; however, the exact residues involved remains to be determined.

Figure 17E:
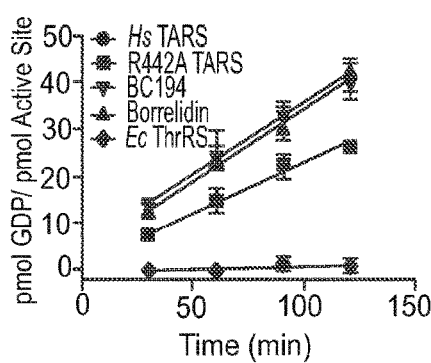
Figure 17F:
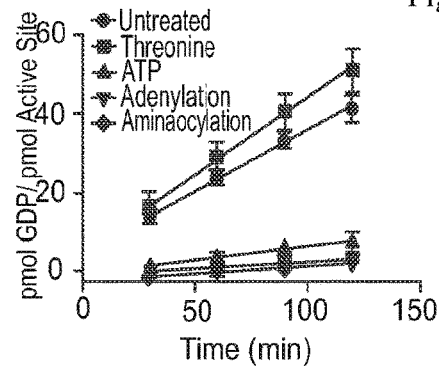
Figure 18A:
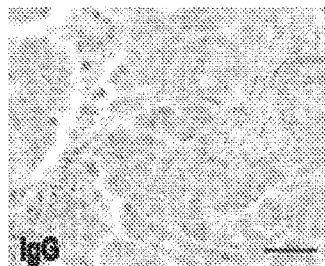
FIG. 18A-F provides photomicrograph images and graphs showing TARS expression by immunohistochemistry (IHC) is increased in human serous papilloma ovarian cancer and colocalizes with VEGF. Patient tumor samples were sectioned, and stained using anti-TARS (FIG. 18B) or anti-VEGF (FIG. 18C) antibodies. Control (FIG. 18A) for staining had no primary antibody (No Ab). Slides were lightly stained with hematoxylin and eosin for visualizing cell structures. Statistical analysis shows expression of TARS is significantly increased in ovarian cancer (FIG. 18D), and regression analysis correlates TARS in tumor tissue with levels of VEGF (FIG. 18E) and serum levels of TARS (FIG. 18F) as measured by ELISA.
Figure 18B:
Figure 18C:
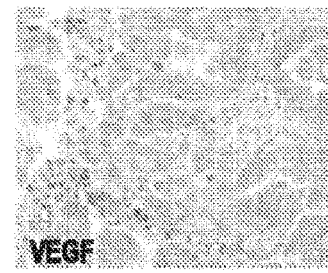
Figure 18D:
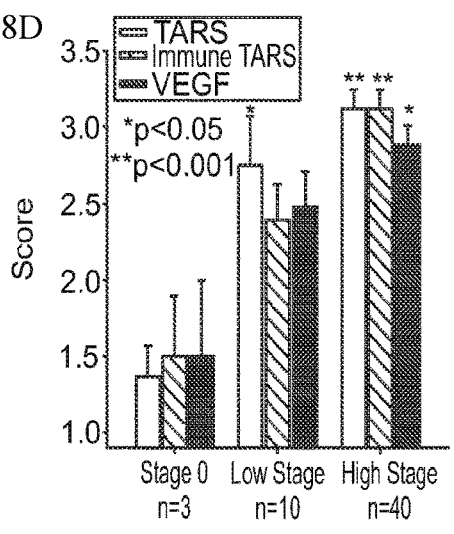
Figure 18E:
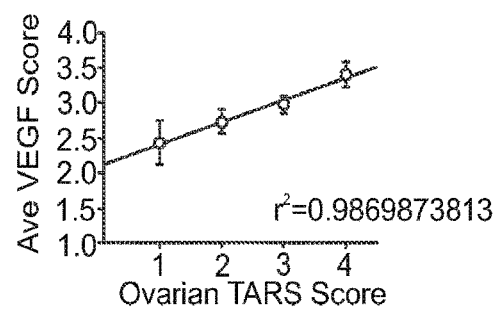
Figure 18F:
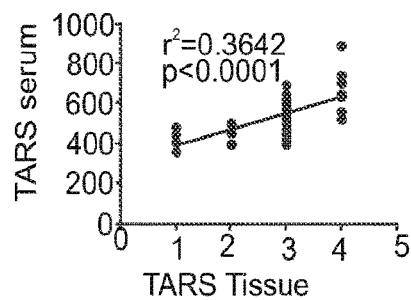

Another reaction in which aminoacyl-tRNA synthetases can potentially modulate signaling is GTP hydrolysis. Recent published work that indicates that LeuRS may contribute amino acid sensing properties to the Mammalian Target of Rapamycin complex (mTOR) by virtue of interactions with the Rag GTPase a mediator of amino acid signaling to mTORC1 (Bonfils, Jaquenoud et al., 2012; Han, Jeong et al., 2012). In contrast to the dinucleotide synthesis, TARS GTPase activity differs greatly in response to similar treatments. As shown in FIGS. 17E and 17F, a direct stimulation of GTP hydrolysis by TARS was observed in both the wildtype and R442A TARS (0.3033 and 0.2137 GDP/active site/min respectively) but not in $E.\ coli$ ThrRS. Furthermore, there was no observable change upon treatment with either BC194 or borrelidin. Taken together, these data would suggest that TARS GTPase activity is specific to the human enzyme (relative to $E.\ coli$) and does not require the same catalytic residues as aminoacylation. Despite this apparent disconnect to aminoacylation, GTPase activity is responsive to the availability of canonical substrates. While threonine appears slightly stimulating (26% increase in activity) ATP, adenylation, and aminoacylation conditions decrease activity by 77%, 90%, and 89% respectively. Given that all of these conditions require ATP, it may be that the two nucleotides compete for the same site. However, there is not enough information to rule out an allosteric form of inhibition as well. Interestingly, the formation of Ap4G requires ATP to be present but maintains the same activity of Ap4A, suggesting that the use of GTP in the synthesis of dinucleotides is not similarly regulated.

Example 6

TARS is Overexpressed in Ovarian Cancer

Materials and Methods for Example 6

Ovarian Cancer Study Group—

The ovarian cancer studies were approved by the University of Vermont's institutional review board (CHRMS 01-026 and M12-004). The study group consisted of 58 patients diagnosed with epithelial ovarian cancer at Fletcher Allen Health Care/University of Vermont between 1999 and 2001. The control group consisted of 16 women who underwent oophorectomies for gynecologic reasons (other than ovarian cancer) and the final pathology demonstrated normal ovarian tissue. Serum and paraffin embedded samples from both the study and control group were obtained after adequate portions of the samples were evaluated for pathologic diagnosis. Histological subtype was based according to the WHO criteria and grading of tumors. Formalin-fixed, paraffin embedded tissue samples from each patient were retrieved. Three serial sections (6 µm) from each specimen were cut and transferred to slides, then analyzed using immunohistochemistry to measure the expression of VEGF and TARS as previously described (Wong, Wellman et al., 2003). After deparaffinization and rehydration, slides were incubated at 97° C. for 15 min with DAKO target retrieval solution, containing 100 mM Tris base, pH 10.5 and 0.1% Triton X-100. Immunoperoxidase staining was performed using the mouse ImmunoCruz staining system (Santa Cruz Biotechnology, Santa Cruz, Calif.) according to the manufacturer's protocol. Antibodies were mouse monoclonal anti-VEGF (1:100, Santa Cruz Biotechnology) and mouse monoclonal anti-TARS (1:100, Clone 1A9 Abnova, Taipei City, Taiwan). Normal mouse IgG was used as a negative control. After immunoperoxidase staining, cells were lightly stained with Mayers' hematoxylin and eosin. Slides were dehydrated through xylenes then mounted with coverslips using Cytoseal 60 (Richard-Allan Scientific, Kalamazoo, Mich.). Images were obtained using an Olympus BX50 light microscope coupled to a CCD camera and Metamorph image capture software. Slides were scored for the expression of VEGF and TARS on a scale of 1-4 where 1=no staining and 4=intense staining. TARS ELISA was performed on undiluted serum following the manufacturer's instructions (Cusabio Biotech; Wuhan, P.R. China). Statistical significance was determined using Kruskal-Wallis test. Correlation between TARS and VEGF expression was evaluated using multiple regression correlation coefficient.

Results for Example 6

It has previously been shown that VEGF is overexpressed in ovarian cancer and correlates with progression of disease (Wong, C. et al. (2003) *Gynecol Oncol* 91 (3), 513-517). To determine whether TARS is dysregulated in human ovarian cancer, immunohistochemical staining for TARS was performed on patient tumor sections and correlated with staining of VEGF and serum levels of TARS. In the samples analyzed, TARS staining colocalized with VEGF and was selectively overexpressed in the tumor cells (FIG. 18). In addition, TARS serum levels significantly correlated with TARS tissue levels, supporting further analysis of TARS as an indicator of ovarian cancer (FIG. 18). Scoring and statistical analyses of data from all of the patients is ongoing and additional patients will be recruited to determine if TARS levels correlate with stage of disease as well as patient outcome leading to Example 7.

Example 7

Identifying a Clinical Relationship Between Cancer and TARS Protein Level and Activity in Tissue and Serum Studies are performed establishing a clinical connection by correlating existing measurements of overexpressed HIF-1α and VEGF in human ovarian cancer (Wong, Wellman et al., 2003) with levels of TARS protein in tissue and serum. For these experiments immunohistochemistry is used in ovarian tissue sections and ELISA of blood samples from ovarian cancer patients to correlate TARS levels with angiogenesis and outcome in human ovarian cancer. TARS levels are elevated in ovarian cancer patients in a similar pattern as VEGF expression and TARS is expected to be detected at higher levels in the serum of patients with TARS-positive ovarian cancer.

Results of these experiments better define the newly discovered pathway whereby cells regulate angiogenesis through unconventional signaling by an aminoacyl tRNA synthetase. These experiments also determine the anti-angiogenic activity of TARS inhibitors, which suggest their development for and use as a therapeutic in ovarian and other angiogenesis-dependent cancers. Furthermore, these experiments determine if TARS secretion can be used as a means of detecting angiogenic ovarian cancer to assist in earlier diagnosis and improved treatment regimens for ovarian cancer patients.

Studies are performed that include measuring TARS expression in tumors and serum obtained from cancer patients, including but not limited to ovarian cancer patients, prostate cancer patients, etc. In the studies, angiogenesis markers such as PECAM are compared with control levels and the cancer's status, stage, and progression and the subject's prognosis is determined. Additional types of cancers tested are metastatic carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, and/or mesothelioma.

Experiments are performed and TARS activity and/or expression is measured in samples from one or more subjects that have or are suspected of being at risk of having additional diseases and conditions such as angiogenesis-associated disorder in which the level of TARS is increased as compared to a normal control level. A TARS level is determined to assess a cancer, a tumor, a hemangioma, a vascular overgrowth, a venous malformation, an arterial malformation, overweight, macular degeneration, an inflammatory disease, psoriasis, diabetes, or rheumatoid arthritis.

Additional studies are performed and TARS activity and/ or expression is determined in samples from one or more subjects that have or are suspected of being at risk of having additional diseases and conditions such as angiogenesis-associated disorder in which the level of TARS is decreased as compared to a normal control level. A TARS level is determined for a tissue implant, an organ implant, ischemia, cardiac infarction, tissue trauma, cartilage to bone transformation, stroke, surgery, pregnancy, macular degeneration, and/or vascular occlusion.

The stage and prognosis for one or more of the diseases and conditions listed above elsewhere herein are assessed by determining the level of TARS in a sample and comparing the level to a level in a control sample.

REFERENCES

Additional references are cited in Specification and Examples.

Ahmed, S. A., R. M. Gogal, Jr., et al. (1994). "A new rapid and simple non-radioactive assay to monitor and determine the proliferation of lymphocytes: an alternative to [3H]thymidine incorporation assay." *J Immunol Methods* 170(2): 211-24.

Altundag, K., O. Altundag, et al. (2005). "CA125 Nadir values as a prognostic factor in epithelial ovarian cancer." *J Clin Oncol* 23(10): 2435-6; author reply 2436.

Arnaoutova, I. and H. K. Kleinman (2010). "In vitro angiogenesis: endothelial cell tube formation on gelled basement membrane extract." *Nat Protoc* 5(4): 628-35.

Bonfils, G., M. Jaquenoud, et al. (2012). "Leucyl-tRNA synthetase controls TORC1 via the EGO complex." *Mol Cell* 46(1): 105-10.

Cassavaugh, J. M., S. A. Hale, et al. (2011). "Negative regulation of HIF-1alpha by an FBW7-mediated degradation pathway during hypoxia." *J Cell Biochem* 112(12): 3882-90.

Chang, H., I. B. Yanachkov, et al. (2010). "Agonist and antagonist effects of diadenosine tetraphosphate, a platelet dense granule constituent, on platelet P2Y1, P2Y12 and P2X1 receptors." *Thromb Res* 125(2): 159-65.

Conant, J L, Penz, Z, Evans M F, Naud S, Cooper K (2011) Sarcomatoid renal cell carcinoma is an examples of epithelial-mesenchymal transition. *J. Clin. Path.* 64(12); 1088-1092.

Delicado, E. G., M. T. Miras-Portugal, et al. (2006). "Dinucleoside polyphosphates and their interaction with other nucleotide signaling pathways." *Pflugers Arch* 452 (5): 563-72.

Ewing, R. M., P. Chu, et al. (2007). "Large-scale mapping of human protein-protein interactions by mass spectrometry." *Mol Syst Biol* 3: 89.

Francklyn, C. S., E. A. First, et al. (2008). "Methods for kinetic and thermodynamic analysis of aminoacyl-tRNA synthetases." *Methods* 44(2): 100-18.

Greenberg, Y., M. King, et al. (2008). "The novel fragment of tyrosyl tRNA synthetase, mini-TyrRS, is secreted to induce an angiogenic response in endothelial cells." *FASEB J* 22(5): 1597-605.

Guo, R. T., Y. E. Chong, et al. (2009). "Crystal structures and biochemical analyses suggest a unique mechanism and role for human glycyl-tRNA synthetase in Ap4A homeostasis." *J Biol Chem* 284(42): 28968-76.

Han, J. M., S. J. Jeong, et al. (2012). "Leucyl-tRNA synthetase is an intracellular leucine sensor for the mTORC1-signaling pathway." *Cell* 149(2): 410-24.

Lee, Y. N., H. Nechushtan, et al. (2004). "The function of lysyl-tRNA synthetase and Ap4A as signaling regulators of MITF activity in FcepsilonRI-activated mast cells." *Immunity* 20(2): 145-51.

Longair, M. H., D. A. Baker, et al. (2011). "Simple Neurite Tracer: open source software for reconstruction, visualization and analysis of neuronal processes." *Bioinformatics* 27(17): 2453-4.

Lounsbury, K. M., A. L. Beddow, et al. (1994). "A family of proteins that stabilize the Ran/TC4 GTPase in its GTP-bound conformation." *J Biol Chem* 269(15): 11285-90.

McLennan, A. G. (2000). "Dinucleoside polyphosphates-friend or foe?" *Pharmacol Ther* 87(2-3): 73-89.

Mor, G., I. Visintin, et al. (2005). "Serum protein markers for early detection of ovarian cancer." *Proc Natl Acad Sci USA* 102(21): 7677-82.

Ofir-Birin, Y., P. Fang, et al. (2013). "Structural Switch of Lysyl-tRNA Synthetase between Translation and Transcription." *Mol Cell* 49(1): 30-42.

Ribatti, D., B. Nico, et al. (2006). "The gelatin sponge-chorioallantoic membrane assay." *Nat Protoc* 1(1): 85-91.

Roedersheimer, M., H. Nijmeh, et al. (2011). "Complementary effects of extracellular nucleotides and platelet-derived extracts on angiogenesis of vasa vasorum endothelial cells in vitro and subcutaneous Matrigel plugs in vivo." *Vasc Cell* 3(1): 4.

Ruan, B., M. L. Bovee, et al. (2005). "A unique hydrophobic cluster near the active site contributes to differences in borrelidin inhibition among threonyl-tRNA synthetases." *J Biol Chem* 280(1): 571-7.

Strausberg, R. L. (2001). "The Cancer Genome Anatomy Project: new resources for reading the molecular signatures of cancer." *J Pathol* 195(1): 31-40.

Svensson, K. J., P. Kucharzewska, et al. (2011). "Hypoxia triggers a proangiogenic pathway involving cancer cell microvesicles and PAR-2-mediated heparin-binding EGF signaling in endothelial cells." *Proc Natl Acad Sci USA* 108(32): 13147-52.

Tomlins, S. A., R. Mehra, et al. (2007). "Integrative molecular concept modeling of prostate cancer progression." *Nat Genet* 39(1): 41-51.

Uhlen, M., P. Oksvold, et al. (2010). "Towards a knowledge-based Human Protein Atlas." *Nat Biotechnol* 28(12): 1248-50.

Wakasugi, K. and P. Schimmel (1999). "Two distinct cytokines released from a human aminoacyl-tRNA synthetase." *Science* 284(5411): 147-51.

Williams, T. F., A. C. Mirando, et al. (2013). "Secreted Threonyl-tRNA synthetase stimulates endothelial cell migration and angiogenesis." *Scientific Reports* 3. 1317; DOI: 10.1038/srep01317.

Wilkinson, B., M. A. Gregory, et al. (2006). "Separation of anti-angiogenic and cytotoxic activities of borrelidin by modification at the C17 side chain." *Bioorg Med Chem Lett* 16(22): 5814-7.

Wong, C., T. L. Wellman, et al. (2003). "VEGF and HIF-1alpha expression are increased in advanced stages of epithelial ovarian cancer." *Gynecol Oncol* 91(3): 513-7.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method of diagnosing a subject as having, or at increased risk of developing, a cancer or proliferative disease or condition associated with increased threonyl- tRNA synthetase (TARS) activity, the method comprising
   (a) obtaining a biological sample from a subject;
   (b) measuring the amount of a TARS molecule in the biological sample; and
   (c) comparing the level of the TARS molecule in the biological sample to a control level of the TARS molecule, wherein the control level is a normal control level or a disease control level,
   (d) identifying the status in the subject of the cancer or proliferative disease or condition associated with increased TARS activity based at least in part on the comparing, wherein if:
       (i) the subject's biological sample is compared to a normal control, an increase in the level of the TARS molecule in the subject's biological sample compared to the normal control level identifies the status of the cancer or proliferative disease or condition associated with increased TARS activity in the subject as present or at increased risk of being present and a decrease in the level of the TARS molecule in the biological sample compared to the normal control level does not identify the status of the cancer or proliferative disease or condition associated with increased TARS activity in the subject as present or at increased risk of being present; or
       (ii) the subject has been previously determined to have the cancer or proliferative disease or condition associated with increased TARS activity and the control is a disease control, wherein an increase in the level of the TARS molecule in the subject's biological sample compared to the disease control level identifies the status of the cancer or proliferative disease or condition associated with increased TARS activity in the subject as progressing and a decrease in the level of the TARS molecule in the subject's biological sample compared to the disease control level identifies the status of the cancer or proliferative disease or condition associated with increased TARS activity in the subject as regressing;
   (e) selecting a therapeutic regimen for the subject based at least in part on the subject's identified status, wherein
       (i) if the identified status in the subject is present or progressing, the therapeutic regimen comprises beginning or increasing administration to the subject of one or more of a surgery, radiation, and chemotherapy to treat the cancer or proliferative disease or condition associated with increased TARS activity compared to the regimen before testing;
       (ii) if the identified status in the subject is not present or regressing the therapeutic regimen comprises stopping administering to the subject one or more of a surgery, radiation, and chemotherapy to treat the cancer or proliferative disease or condition associated with increased TARS activity; and
   (f) administering the selected therapeutic regimen to the subject.

2. The method of claim 1 wherein the level of the TARS molecule is measured by measuring a secreted TARS molecule.

3. The method of claim 1, wherein the level of the TARS molecule is measured by measuring a non-secreted TARS molecule.

4. The method of claim 1, wherein the level of the TARS molecule is measured by measuring the activity of the TARS molecule.

5. The method of claim 1, wherein the cancer or proliferative disease or condition associated with increased TARS activity is an angiogenesis-associated disorder.

6. The method of claim 5, wherein the angiogenesis-associated disorder is a cancer, a tumor, a hemangioma, vascular overgrowth, venous malformation, arterial malformation, overweight, macular degeneration, inflammatory disease, psoriasis, diabetes, or rheumatoid arthritis.

7. The method of claim 6, wherein angiogenesis-associated disorder is a cancer.

8. The method of claim 7, wherein the cancer is a metastatic cancer.

9. The method of claim 1, wherein the biological sample is a sample of blood, tissue, serum, urine, stool, sputum, cerebrospinal fluid, or supernatant from cell lysate.

10. The method of claim 1, wherein the biological sample comprises a cell or tissue.

11. The method of claim 1, wherein the TARS molecule comprises a TARS polypeptide.

12. The method of claim 1, wherein the TARS molecule comprises a TARS polypeptide-encoding nucleic acid.

13. The method of claim 1, wherein a means of the measuring comprises an immunological assay, nucleic acid determination, mass spectrometry, TARS aminoacylation assay, TARS active site determination assay, or a TARS binding assay comprising a TARS-binding reporter molecule.

14. The method of claim 13, wherein the immunological assay comprises an ELISA assay.

15. The method of claim 1, wherein the method also includes measuring the amount of one more additional biomarker molecules in the biological sample; and
    comparing the level of the one or more measured biomarker molecules to control levels of each of the one or more biomarker molecules, wherein a change in the level of one or more of the biomarker molecules in the subject biological sample compared to the control level is an indication that the subject has or is at increased risk of developing the cancer or proliferative disease or condition associated with increased TARS activity compared to those subjects not having an increase in the biomarkers.

16. The method of claim 1, wherein the disease control of step (d)(ii) comprises one or more biological samples previously obtained from the subject.

* * * * *